(12) United States Patent
Grillot et al.

(10) Patent No.: US 6,632,809 B2
(45) Date of Patent: Oct. 14, 2003

(54) GYRASE INHIBITORS AND USES THEREOF

(75) Inventors: Anne-Laure Grillot, Cambridge, MA (US); Paul Charifson, Framingham, MA (US); Dean Stamos, Framingham, MA (US); Yusheng Liao, Lexington, MA (US); Michael Badia, Bedford, MA (US); Martin Trudeau, Tewksbury, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 75 days.

(21) Appl. No.: 10/015,332

(22) Filed: Dec. 12, 2001

(65) Prior Publication Data

US 2003/0119868 A1 Jun. 26, 2003

Related U.S. Application Data

(60) Provisional application No. 60/256,094, filed on Dec. 15, 2000, and provisional application No. 60/275,292, filed on Mar. 13, 2001.

(51) Int. Cl.⁷ .................. C07D 403/04; C07D 413/04; C07D 235/30; A61K 31/55
(52) U.S. Cl. ............... 514/215; 514/234.5; 514/252.14; 514/252.19; 514/256; 514/269; 514/275; 514/293; 514/303; 514/314; 514/318; 514/322; 514/338; 514/364; 514/375; 514/395; 548/143; 548/222; 548/304.7; 548/305.1; 548/306.1; 548/308.1; 546/82; 546/118; 546/167; 546/193; 546/199; 546/271.7; 546/273.1; 546/273.4; 544/122; 544/124; 544/324; 544/330; 544/331; 544/333; 540/578
(58) Field of Search .................. 540/578; 544/122, 544/124, 324, 330, 331, 333; 546/82, 118, 167, 193, 199, 271.7, 273.1, 273.4; 548/143, 222, 304.7, 305.1, 306.1, 308.1; 514/215, 234.5, 252.14, 252.19, 256, 269, 275, 293, 303, 314, 318, 322, 338, 364, 375, 395

(56) References Cited

U.S. PATENT DOCUMENTS

| | | | |
|---|---|---|---|
| 4,174,400 A | 11/1979 | Mrozik | 424/273 B |
| 4,512,998 A | 4/1985 | Nafissi-Varchei | 514/367 |
| 5,529,998 A | 6/1996 | Häbich et al. | 514/233.8 |

FOREIGN PATENT DOCUMENTS

| | | |
|---|---|---|
| EP | 0 738 726 A1 | 10/1996 |
| EP | 1 055 668 A1 | 11/2000 |
| WO | WO 99/35155 | 7/1999 |
| WO | WO 00/49015 | 8/2000 |
| WO | WO 00/71522 | 11/2000 |

OTHER PUBLICATIONS

Singh, S.K., et al., "Studies in antiparasitic agents: Part 13—Synthesis of 4–aryl–2–substitutedamino–thiazoles as potential anthelmintics," *Indian J. Chem.*, 28B(9):786–789 (1989).
Beers, M. H., and Berkow, R., "The Merck Manual of Diagnosis and Therapy", 7th Edition, Chapter 156—Bacteremia and Septic Shock, *Merck Research Laboratories, Whitehouse Station, NJ*, pp. 1143–1147 (1999).
Nicolaus B. J. R., "Symbolic Approach to Drug Design," Decision Making in Drug Research, pp. 173–186 (1983).
Kus, C., et al., "Synthesis and antimicrobial activities of 5–fluoro–1, 2, 6–trisubstituted benzimidazole carboxamide and acetamide derivatives," Arch. Pharm. Pharm. Med. Chem. 334(11):361–365 (2001).

*Primary Examiner*—Deepak Rao
(74) *Attorney, Agent, or Firm*—Andrea L. C. Robidoux; Vertex Pharmaceuticals Incorporated

(57) ABSTRACT

The present invention relates to compounds of the formula I:

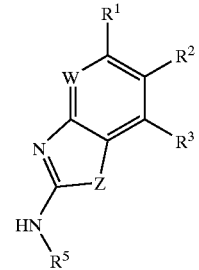

or a pharmaceutically acceptable derivative or prodrug thereof. The compounds are useful as inhibitors of bacterial gyrase activity. The present invention also relates to methods for treating bacterial infections in mammala. The present invention also relates to methods for decreasing bacterial quantity in a biological sample.

26 Claims, No Drawings

GYRASE INHIBITORS AND USES THEREOF

CROSS REFERENCE TO RELATED APPLICATIONS

This application claims priority to U.S. Provisional Patent Application No. 60/256,094 filed Dec. 15, 2000 and U.S. Provisional Patent Application No. 60/275,292 filed Mar. 13, 2001, the contents of which are incorporated herein by reference.

FIELD OF THE INVENTION

This invention is in the field of medicinal chemistry and relates to compounds, and pharmaceutical compositions thereof, that inhibit bacterial gyrases. The compounds are useful as inhibitors of bacterial gyrase activity. The present invention also relates to methods for treating bacterial infections in mammals. The present invention also relates to methods for decreasing bacterial quantity in a biological sample.

BACKGROUND OF THE INVENTION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as *Streptococcus pneumoniae* (SP), *Mycobacterium tuberculosis*, and Enterococcus. The appearance of vancomycin resistant enterococcus was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as *Staphylococcus aureus*, where methicillin resistance is already prevalent (De Clerq, et al., *Current Opinion in Anti-infective Investigational Drugs*, 1999, 1, 1; Levy, "The Challenge of Antibiotic Resistance", *Scientific American*, March, 1998).

Another concern is how quickly antibiotic resistance can spread. For example, until the 1960's SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in *The Medical Reporter*, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", *FDA Consumer* magazine, September 1995).

As a result of the need to combat drug-resistant bacteria and the increasing failure of the available drugs, there has been a resurgent interest in discovering new antibiotics. One attractive strategy for developing new antibiotics is to inhibit DNA gyrase, a bacterial enzyme necessary for DNA replication, and therefore, necessary for bacterial cell growth and division. Gyrase activity is also associated with events in DNA transcription, repair and recombination.

Gyrase is one of the topoisomerases, a group of enzymes which catalyze the interconversion of topological isomers of DNA (see generally, Kornberg and Baker, *DNA Replication*, 2d Ed., Chapter 12, 1992, W. H. Freeman and Co.; Drlica, *Molecular Microbiology*, 1992, 6, 425; Drlica and Zhao, *Microbiology and Molecular Biology Reviews*, 1997, 61, 377). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain which has the ATPase activity, and a carboxy-terminal domain which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase would be selective for this enzyme and be relatively inactive against the eukaryotic type II topoisomerases.

The widely-used quinolone antibiotics inhibit bacterial DNA gyrase. Examples of the quinolones include the early compounds such as nalidixic acid and oxolinic acid, as well as the later, more potent fluoroquinolones such as norfloxacin, ciprofloxacin, and trovafloxacin. These compounds bind to GyrA and stabilize the cleaved complex, thus inhibiting overall gyrase function, leading to cell death. However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, *Trends in Microbiology*, 1997, 5, 102).

For coumarin-resistant bacteria, the most prevalent point mutation is at a surface arginine residue that binds to the carbonyl of the coumarin ring (Arg136 in E. coli GyrB). While enzymes with this mutation show lower supercoiling and ATPase activity, they are also less sensitive to inhibition by coumarin drugs (Maxwell, *Mol. Microbiol.*, 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, *Trends in Microbiology*, 1997, 5, 102). It would be desirable to have a new, effective GyrB inhibitor that overcomes these drawbacks and, preferably, does not rely on binding to Arg136 for activity. Such an inhibitor would be an attractive antibiotic candidate, without a history of resistance problems that plague other classes of antibiotics.

As bacterial resistance to antibiotics has become an important public health problem, there is a continuing need to develop newer and more potent antibiotics. More particularly, there is a need for antibiotics that represent a new class of compounds not previously used to treat bacterial infection. Such compounds would be particularly useful in treating nosocomial infections in hospitals where the formation and transmission of resistant bacteria are becoming increasingly prevalent.

DESCRIPTION OF THE INVENTION

It has now been found that compounds of this invention and pharmaceutical compositions thereof are useful in treating bacterial infections. One embodiment of this invention relates to a method of treating a bacterial infection in a mammal in need thereof, comprising the step of administering to said mammal a therapeutically effective amount of a compound of formula I:

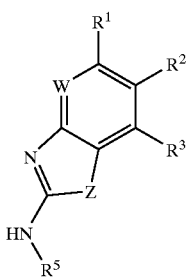

I or a pharmaceutically acceptable derivative or prodrug thereof, wherein:

Z is O or N—$R^4$;

W is nitrogen or $CR^a$;

$R^a$ is selected from hydrogen, halogen, —$CF_3$, $R^7$, —$OR^7$, or —$N(R^7)_2$;

$R^1$ is an aryl or heteroaryl ring, wherein said ring is optionally substituted by up to four $R^9$; wherein an $R^9$ substituent in the ortho-position of $R^1$ taken together with $R^2$ may form a fused, unsaturated or partially unsaturated, optionally substituted 5–8 membered ring having 0–2 ring heteroatoms selected from nitrogen, oxygen, or sulfur;

$R^2$ and $R^3$ are each independently selected from $R^6$, halogen, CN, $SR^6$, $OR^6$, $N(R^6)_2$, $NRCO_2R^6$, $NRCON(R^6)_2$, $CON(R^6)_2$, $NRCOR^6$, $NRN(R^6)_2$, $COR^6$, $CO_2R^6$, $COCOR^6$, $SO_2R^6$, $SO_2N(R^6)_2$, or $NRSO_2R^6$;

or $R^2$ and $R^3$ are taken together to form a fused, unsaturated or partially unsaturated, optionally substituted 5–8 membered ring containing 0–2 ring heteroatoms selected from nitrogen, oxygen, or sulfur;

$R^4$ is selected from $R^6$, $CON(R^6)$, $COR^6$, $CO_2R^6$, $COCOR^6$, $SO_2R^6$, $SO_2N(R^6)_2$, or $(CH_2)_yR^2$;

y is 1–6;

$R^5$ is selected from $R^7$, Ar, COAr, $CON(R^7)$Ar, $(CH_2)_yCO_2R$, $(CH_2)_yN(R^7)_2$, $C(=NR^{10})$—$N(R^7)_2$, $C(=NR^{10})$—NRCOR, $C(=S)$—$N(R^7)_2$, $CON(R^7)_2$, COR, $SO_2R$, or $SO_2N(R^7)_2$;

Ar is a five membered heteroaryl, heterocyclyl, or carbocyclyl ring, wherein said ring is optionally substituted by up to three substituents selected from oxo, halogen, CN, $NO_2$, $R^8$, $OR^8$, $NHR^8$, $NHCOR^8$, $NHCONHR^8$, $COR^8$, $CONHR^8$, $SO_2R^8$, $NHSO_2NHR^8$ or $SO_2NHR^8$;

each $R^6$ is independently selected from $R^7$ or an optionally substituted group selected from alkoxy, hydroxyalkyl, heterocyclyl, heterocyclcylalkyl, aryl, aralkyl, aralkoxy, aryloxyalkyl, heteroaryl, heteroaralkyl, heteroaralkoxy, or heteroarayloxyalkyl;

each $R^7$ is independently selected from hydrogen or an optionally substituted aliphatic group having one to six carbons, or two $R^7$ on the same nitrogen taken together with the nitrogen optionally form a four to six member, saturated or unsaturated heterocyclic ring having one to three heteroatoms;

$R^8$ is a $C_1$–$C_4$ aliphatic group, wherein two $R^8$ on adjacent positions of Ar, or an aryl or heteroaryl ring, may be taken together with their intervening atoms to form a three to six membered fused ring;

each $R^9$ is independently selected from oxo, halogen, CN, $NO_2$, $T_n$(haloalkyl), $R^6$, $SR^6$, $OR^6$, $OR^8$, $N(R^6)_2$, $CON(R^6)_2$, $CON(R)COR^6$, $COR^6$, $CO_2R^6$, $CO_2N(R^6)_2$, $COCOR^6$, $SO_2R^6$, $SO_2N(R^6)_2$, $N(R)T_nCO_2R^6$, $N(R)T_nCON(R^6)_2$, $N(R)T_nN(R^6)_2$, $N(R)T_nNRCO_2R^6$, $N(R)T_nNRCON(R^6)_2$, $N(R)T_nCOR^6$, $N(R)T_nNRCOR^6$, $N(R)T_nSO_2N(R^6)_2$, $N(R)T_nSO_2R^6$, $T_nPO(OR^7)_2$, $T_nOPO(OR^7)_2$, $T_nSP(OR^7)_2$, $T_nPO(OR^7)_2$, or $T_nNPO(OR^7)_2$;

each Q is an independently selected $C_1$–$C_3$ branched or straight alkyl;

T is selected from —Q— or —$Q_m$—$CH(Q_m$—$R^2)$—;

each m and n are independently selected from zero or one;

and $R^{10}$ is selected from $R^7$ or Ar.

As used herein, the following definitions shall apply unless otherwise indicated. In addition, unless otherwise indicated, functional group radicals are independently selected.

The term "aliphatic" as used herein means straight-chain, branched or cyclic $C_1$–$C_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl) alkyl or (cycloalkyl)alkenyl. The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic $C_3$–$C_{12}$ hydrocarbons which are completely saturated or which contain one or more units of unsaturation, but which are not aromatic.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means N, O, or S and includes any oxidized form of nitrogen and sulfur, and the quaternized form of any basic nitrogen.

The term "carbocycle", "carbocyclyl", or "carbocyclic" as used herein means an aliphatic ring system having three to fourteen members. The term "carbocycle", "carbocyclyl", or "carbocyclic" whether saturated or partially unsaturated, also refers to rings that are optionally substituted. The terms "carbocyclyl"or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinoline, tetrahydroisoquinoline, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on the unsaturated carbon atom of an aryl, heteroaryl, aralkyl, or heteroaralkyl group include a halogen, —R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, —(CH$_2$)$_y$NHC(O)R°, —(CH$_2$)$_y$NHC(O)CH(V—R°)(R°); wherein R° is H, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph); y is 0–6; and V is a linker group. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of an aromatic or non-aromatic heterocyclic ring include —R+, —N(R+)$_2$, —C(O)R+, —CO$_2$R+, —C(O)C(O)R+, —C(O)CH$_2$C(O)R+, —SO$_2$R+, —SO$_2$N(R+)$_2$, —C(=S)N(R+)$_2$, —C(=NH)—N ($R^+$)$_2$, and —NR$^+$SO$_2$R$^+$; wherein R$^+$ is H, an aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

The term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200. Examples of linkers include a saturated or unsaturated C$_{1-6}$ alkylidene chain which is optionally substituted, and wherein one or two saturated carbons of the chain are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, or —NHSO$_2$—.

The term "alkylidene chain" refers to an optionally substituted, straight or branched carbon chain that may be fully saturated or have one or more units of unsaturation. The optional substituents are as described above for an aliphatic group.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

One preferred embodiment of this invention relates to a method of treating a bacterial infection in a mammal in need thereof, comprising the step of administering to said mammal a therapeutically effective amount of a compound having the formula Ia or Ib:

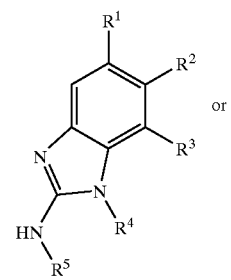

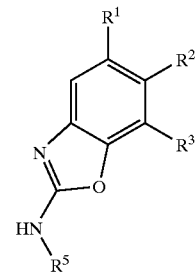

or a pharmaceutically acceptable derivative or prodrug thereof, wherein R$^1$, R$^2$, R$^3$, R$^4$, and R$^5$ are as described above.

Examples of preferred R$^1$ include optionally substituted phenyl, 2-pyridyl, 3-pyridyl, 4-pyridyl, thienyl, pyrimidyl, imidazol-1-yl, imidazol-2-yl, pyrazol-1-yl, aminopyrimidinyl, quinolinyl, aminobenzimidazole, and indolyl. Preferred R$^9$, if present, on the R$^1$ aryl or heteroaryl ring include halogen, CN, oxo, R$^6$, SR$^6$, OR$^6$, N(R$^6$)$_2$, CON(R$^6$)$_2$, CO$_2$R$^6$, CON(R)COR$^6$, N(R)T$_n$CO$_2$R$^6$, N(R)T$_n$NRCO$_2$R$^6$, N(R)T$_n$N(R$^6$)$_2$, NO$_2$, T$_n$(haloalkyl), CO$_2$N(R$^6$)$_2$, COR$^6$, SO$_2$R$^6$, or SO$_2$N(R$^6$)$_2$. Examples of such R$^9$ groups include, but are not limited to, pyrrol-2,5-dione, NR$_2$, OR, CO$_2$H, NO$_2$, OH, NHCOR, NHCO$_2$R, NHCH$_2$CO$_2$R, NH(CH$_2$)$_2$NHCO$_2$R, CH$_2$CO$_2$R, CF$_3$, SO$_2$R, NHCH(CH$_2$OH)CO$_2$H, N—SO$_2$Me-piperidinyl, SMe, NH(CH$_2$)$_2$NH$_2$, and piperidinyl.

Preferred R$^2$ and R$^3$ groups include halogen, CN, CO$_2$R$^6$, OR$^6$, and R$^6$. Examples of preferred R$^3$ groups include Br, F, Cl, COOH, CN, OMe, methyl, ethyl, t-butyl, CF$_3$, OH, and OBn.

Examples of preferred R$^5$ include CO$_2$(aliphatic), C(=NH)—NH$_2$, and CON(R$^7$)$_2$ such as CO(piperidin-1-yl), CONHEt, CONHMe, CONH(cyclopropyl), CONH(isopropyl), CONH(propyl), CONH(pyrrolidinyl), CO$_2$Et, and CO$_2$Me.

Preferred compounds of formula Ia and Ib include those having one or more, or most preferably all, of the features selected from the group consisting of:
  (a) R$^1$ is an optionally substituted aryl or heteroaryl ring;
  (b) R$^2$ and R$^3$ are each independently selected from halogen, CN, CO$_2$R$^6$, OR$^6$, or R$^6$;
  (c) R$^5$ is CO$_2$R, COAr, COR, CON(R$^7$)$_2$, Ar, (CH$_2$)$_y$CO$_2$R, or (CH$_2$)$_y$N(R$^7$)$_2$; and
  (d) R$^9$ is halogen, CN, oxo, R$^6$, SR$^6$, OR$^6$, N(R$^6$)$_2$, CON(R$^6$)$_2$, CO$_2$R$^6$, CON(R)COR$^6$, N(R)T$_n$CO$_2$R$^6$, N(R)T$_n$NRCO$_2$R$^6$, N(R)T$_n$N(R$^6$)$_2$, NO$_2$, T$_n$(haloalkyl), CO$_2$N(R$^6$)$_2$, COR$^6$, SO$_2$R$^6$, or SO$_2$N(R$^6$)$_2$.

More preferred compounds of formula Ia and Ib include those having one or more, or most preferably all, of the features selected from the group consisting of:

(a) $R^1$ is an optionally substituted ring selected from phenyl, 2-pyridyl, 3-pyridyl, 4-pyridyl, thienyl, pyrimidyl, imidazol-1-yl, imidazol-2-yl, pyrazol-1-yl, amino-pyrimidinyl, quinolinyl, aminobenzimidazole, or indolyl;
(b) $R^2$ is hydrogen, alkoxy, aminoalkyl, or halogen;
(c) $R^3$ is hydrogen, alkoxy, aralkoxy, or halogen;
(d) $R^4$ is hydrogen or $(CH_2)_y R^2$;
(e) $R^5$ is $CON(R^7)_2$, Ar, $(CH_2)_y CO_2 R$, or $(CH_2)_y N(R^7)_2$; and
(f) $R^9$ is halogen, CN, oxo, $R^6$, $SR^6$, $OR^6$, $N(R^6)_2$, $CON(R^6)_2$, $CO_2 R^6$, $CON(R)COR^6$, or $N(R)T_n CO_2 R^6$.

Selected compounds of formula Ia are set forth in Table 1 below.

TABLE 1

| No. Ia- | Structure |
|---|---|
| 1 | 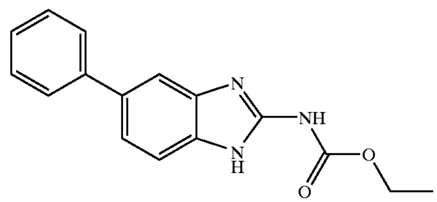 |
| 2 | 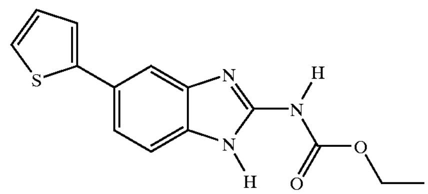 |
| 3 | 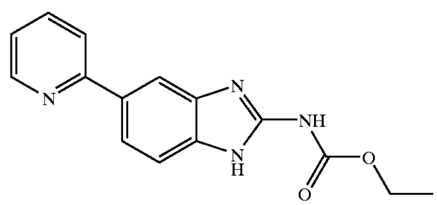 |
| 4 | 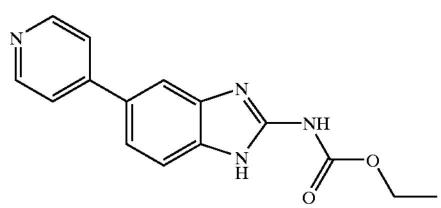 |
| 5 | 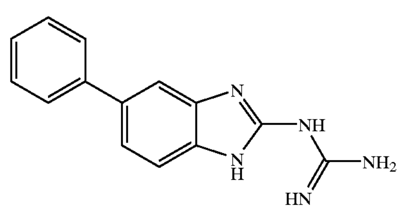 |
| 6 | 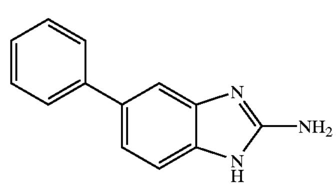 |

TABLE 1-continued
| No. Ia- | Structure |
|---|---|
| 7 | 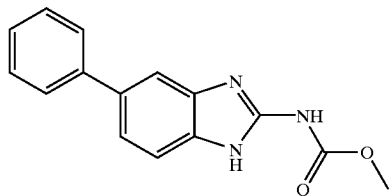 |
| 8 | 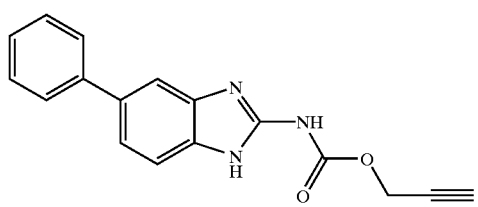 |
| 9 | 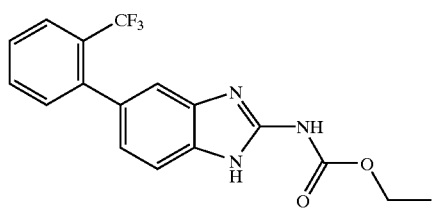 |
| 10 | 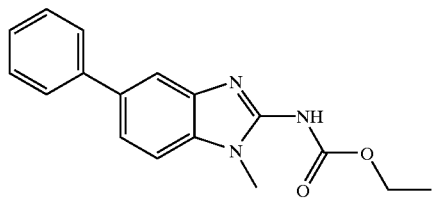 |
| 11 | 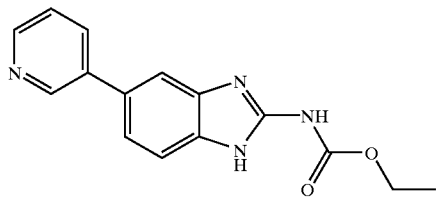 |
| 12 | 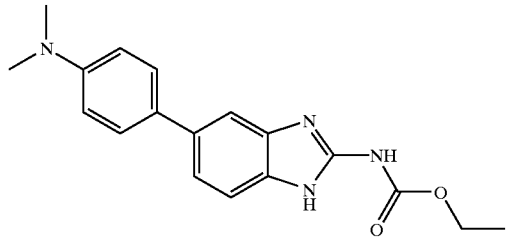 |

TABLE 1-continued
| No. Ia- | Structure |
|---|---|
| 13 | 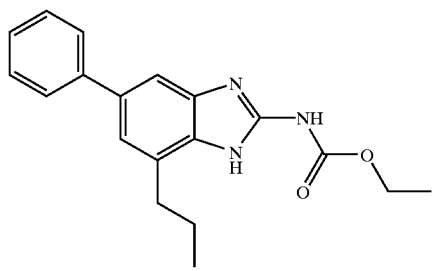 |
| 14 | 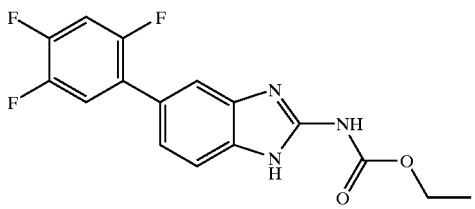 |
| 15 | 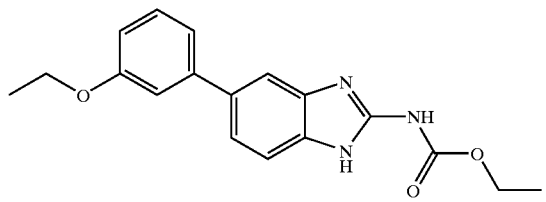 |
| 16 | 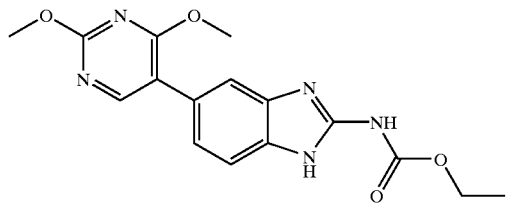 |
| 17 | 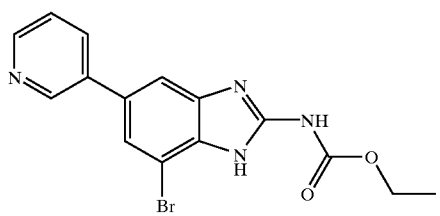 |
| 18 | 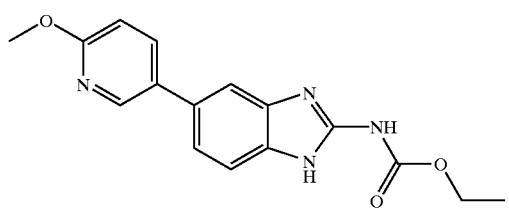 |
| 19 | 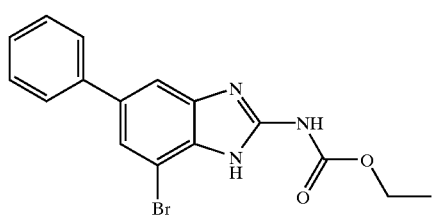 |

TABLE 1-continued
| No. Ia- | Structure |
|---|---|
| 20 | 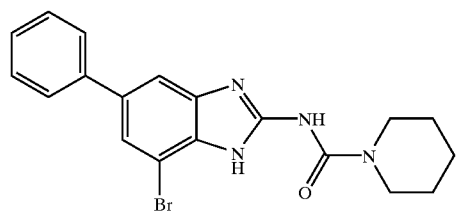 |
| 21 | 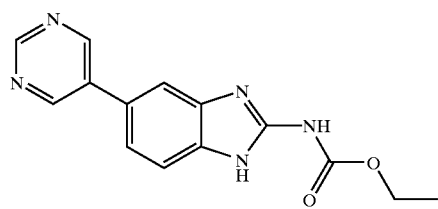 |
| 22 | 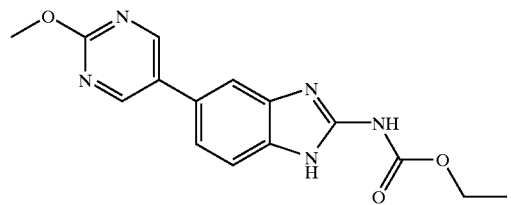 |
| 23 | 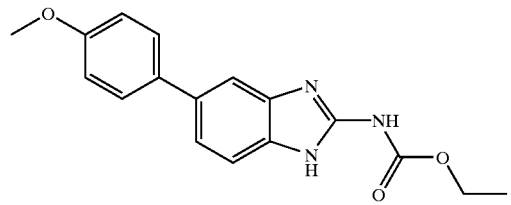 |
| 24 | 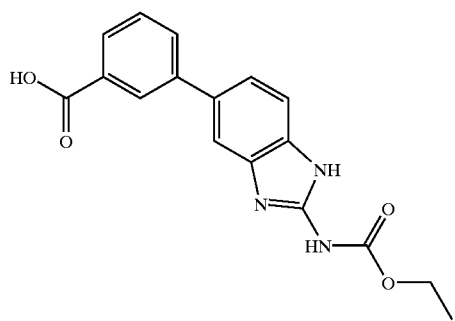 |
| 25 | 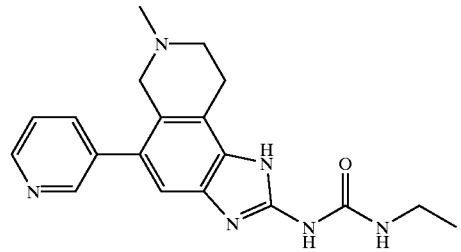 |

TABLE 1-continued
| No. Ia- | Structure |
|---|---|
| 26 | 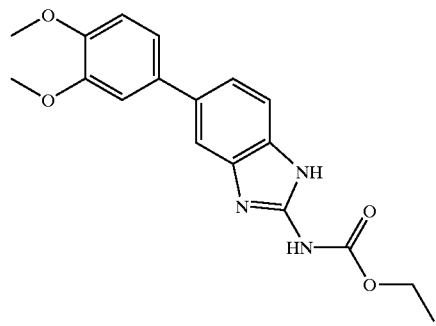 |
| 27 | 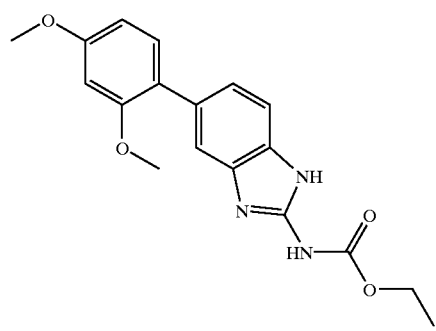 |
| 28 | 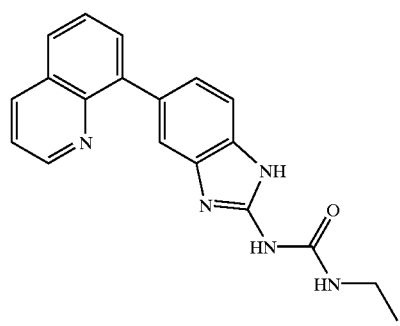 |
| 29 | 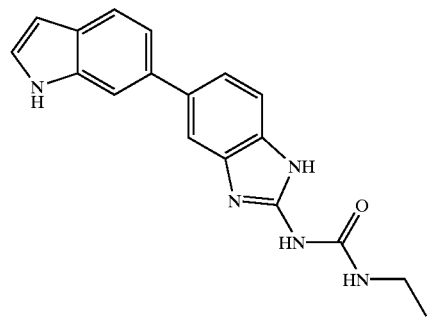 |

TABLE 1-continued
| No. Ia- | Structure |
|---|---|
| 30 | 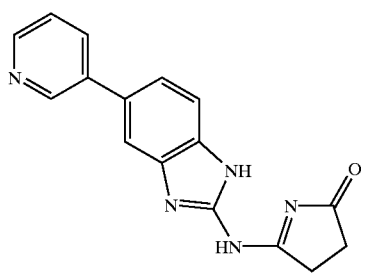 |
| 31 | 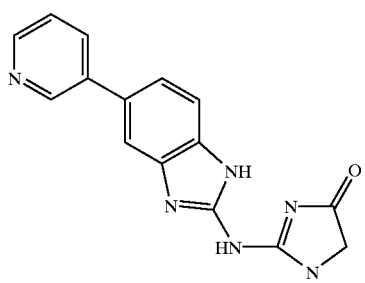 |
| 32 | 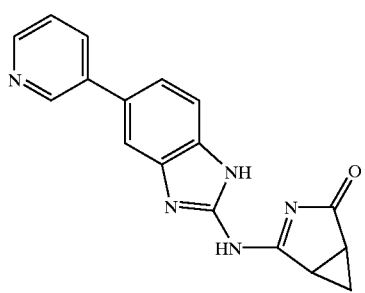 |
| 33 | 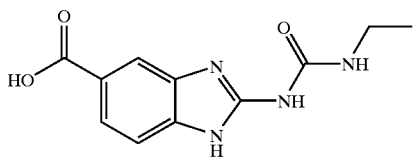 |
| 34 | 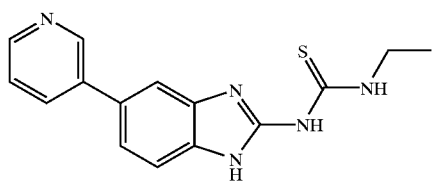 |
| 35 | 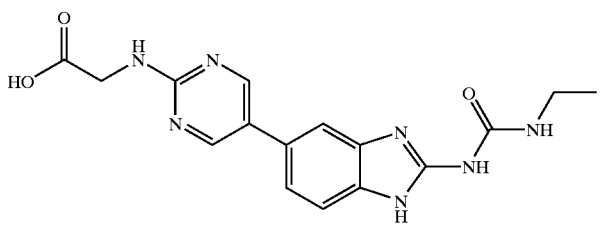 |

TABLE 1-continued

| No. Ia- | Structure |
|---|---|
| 36 | [chemical structure: 5-phenyl-benzimidazol-2-yl N-ethyl thiourea] |
| 37 | [chemical structure: tert-butyl ester glycine-pyrimidinyl-benzimidazol-2-yl N-ethyl thiourea] |
| 38 | [chemical structure: 5-(pyridin-3-yl)-benzimidazol-2-yl N-cyclopropyl urea] |
| 39 | [chemical structure: carboxymethylamino-pyrimidinyl-benzimidazol-2-yl N-ethyl thiourea] |
| 40 | [chemical structure: tert-butyl ester O-tert-butyl serine-pyrimidinyl-benzimidazol-2-yl N-ethyl urea] |
| 41 | [chemical structure: tert-butyl ester O-tert-butyl serine-pyrimidinyl-benzimidazol-2-yl cyanamide] |
| 42 | [chemical structure: 5-(pyridin-3-yl)-6-methoxy-benzimidazol-2-yl N-ethyl urea] |

TABLE 1-continued

| No. Ia- | Structure |
|---|---|
| 43 | 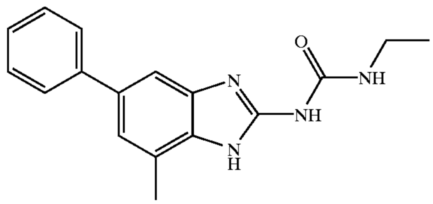 |
| 44 | 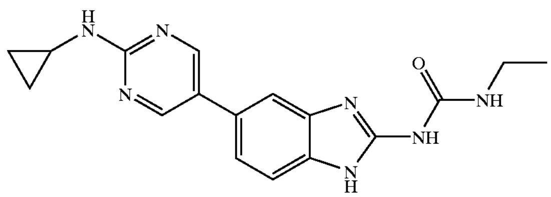 |
| 45 | 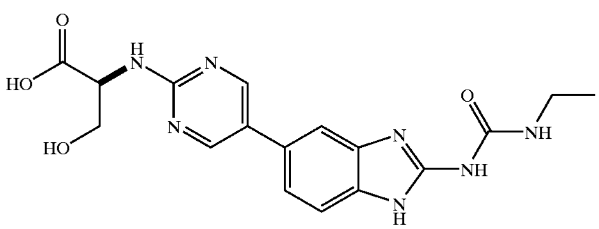 |
| 46 | 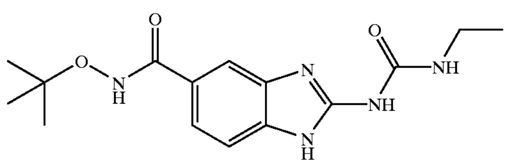 |
| 47 | 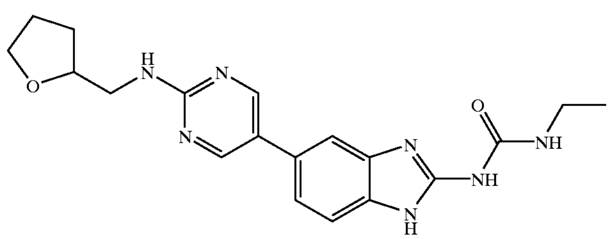 |
| 48 | 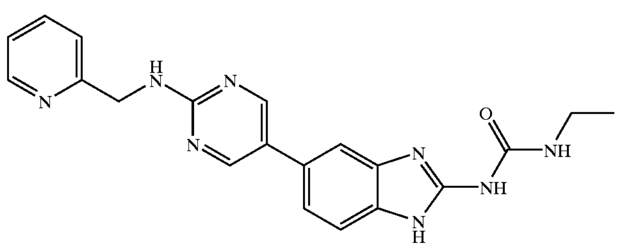 |
| 49 | 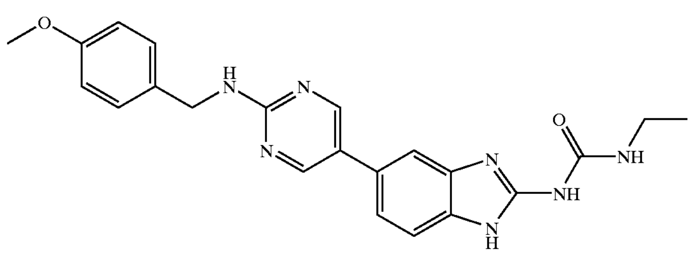 |

TABLE 1-continued
| No. Ia- | Structure |
|---|---|
| 50 | 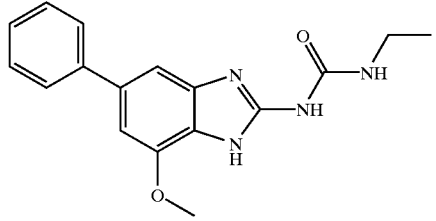 |
| 51 | 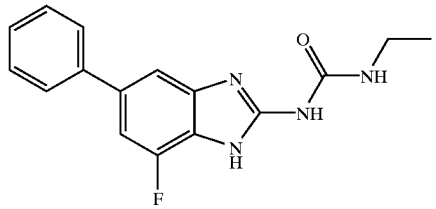 |
| 52 | 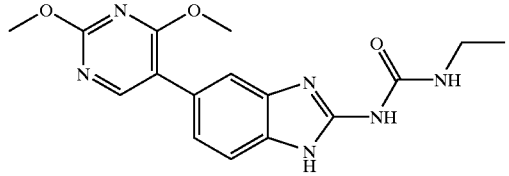 |
| 53 | 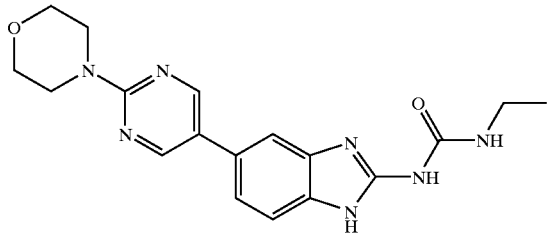 |
| 54 | 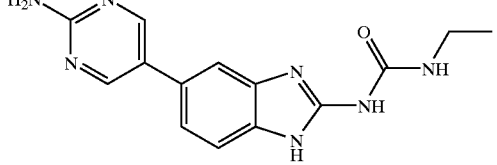 |
| 55 | 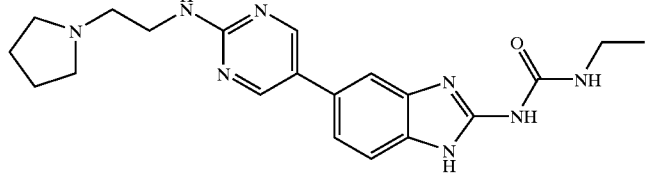 |
| 56 | 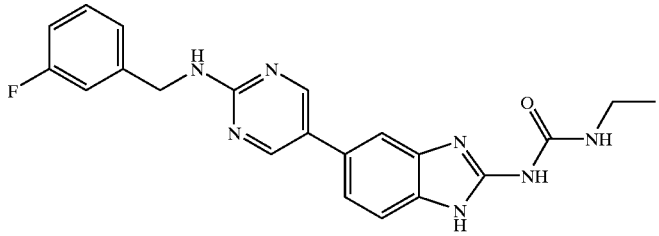 |

TABLE 1-continued
| No. Ia- | Structure |
|---|---|
| 57 | 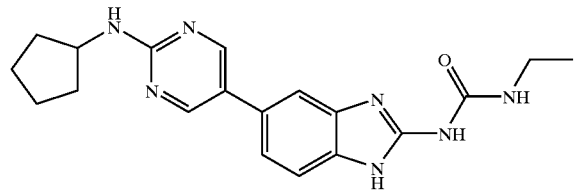 |
| 58 | 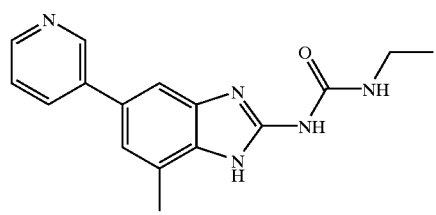 |
| 59 | 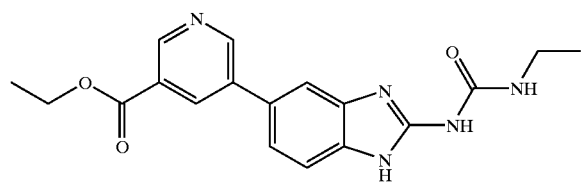 |
| 60 | 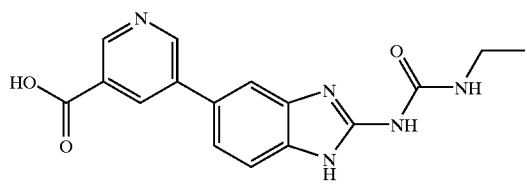 |
| 61 | 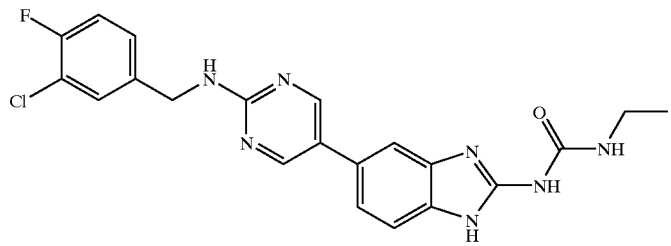 |
| 62 | 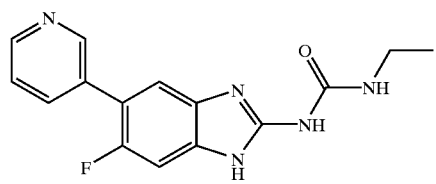 |
| 63 | 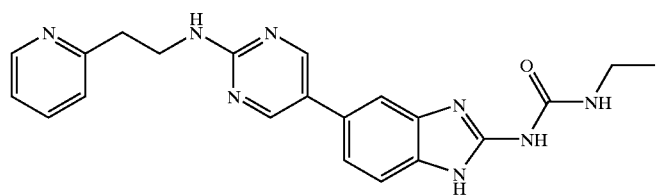 |

TABLE 1-continued
| No. Ia- | Structure |
|---|---|
| 64 | 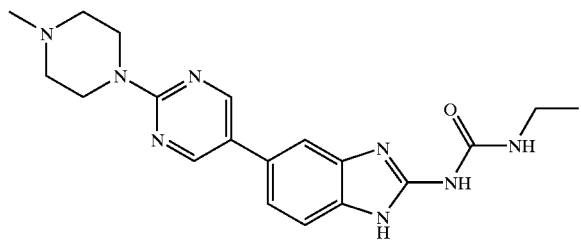 |
| 65 | 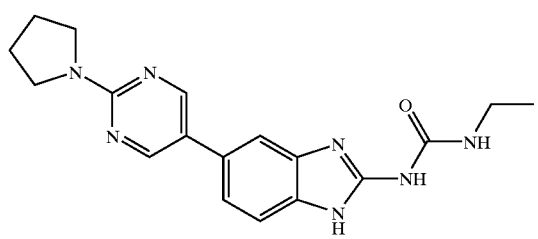 |
| 66 | 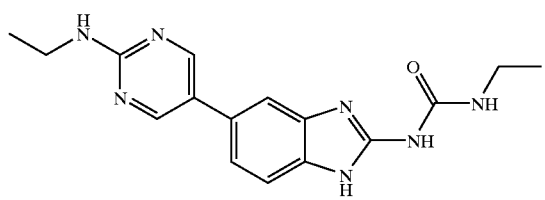 |
| 67 | 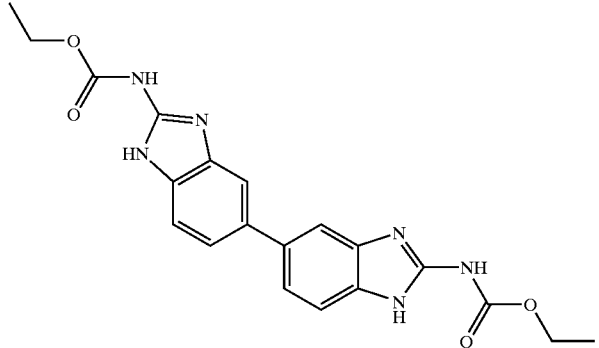 |
| 68 | 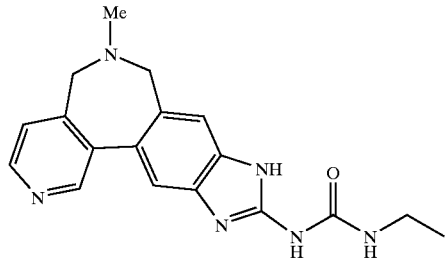 |

TABLE 1-continued
| No. Ia- | Structure |
|---|---|
| 69 | 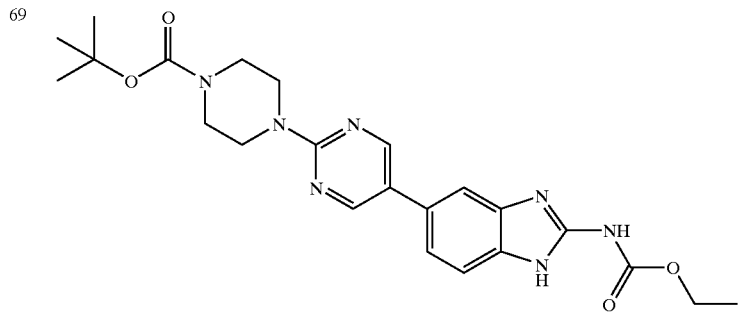 |
| 70 | 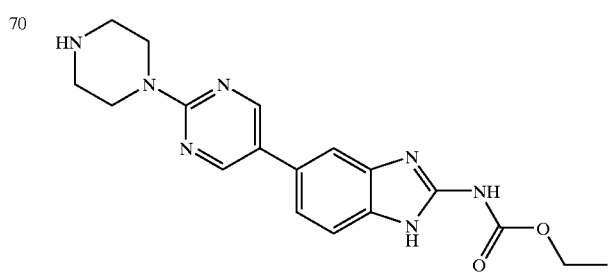 |
| 71 | 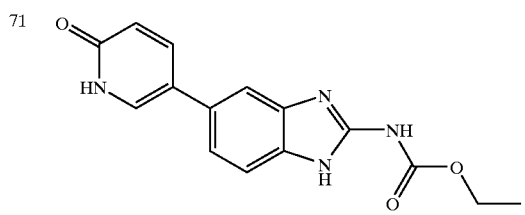 |
| 72 | 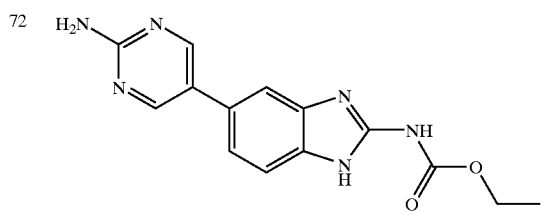 |
| 73 | 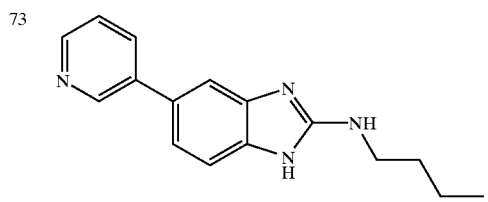 |
| 74 | 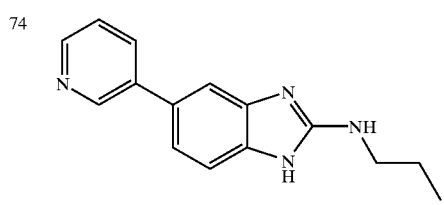 |

TABLE 1-continued
| No. Ia- | Structure |
| --- | --- |
| 75 | 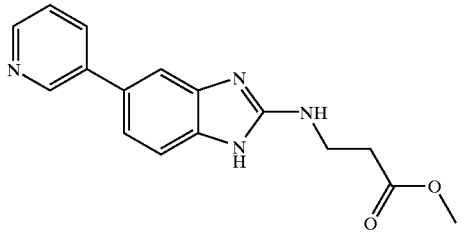 |
| 76 | 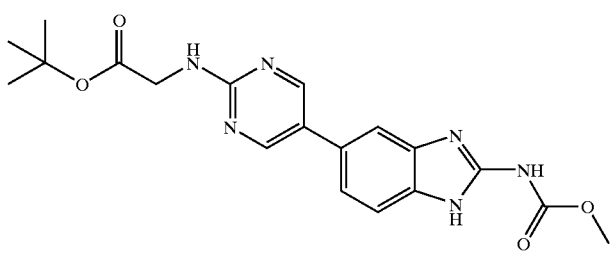 |
| 77 | 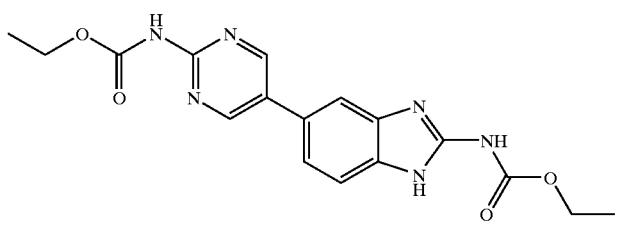 |
| 78 | 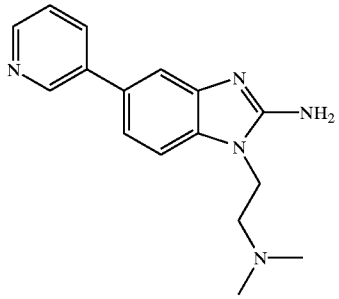 |
| 79 | 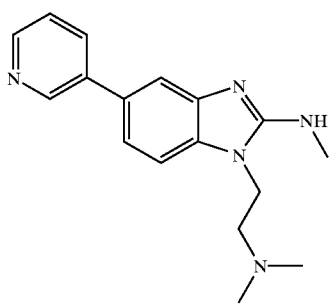 |

TABLE 1-continued
| No. Ia- | Structure |
|---|---|
| 80 | 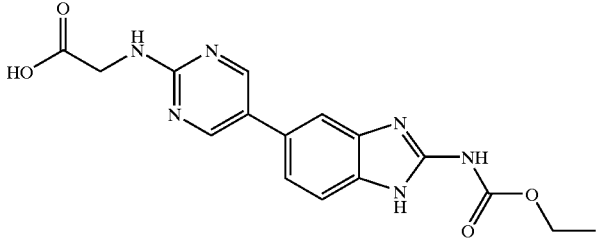 |
| 81 | 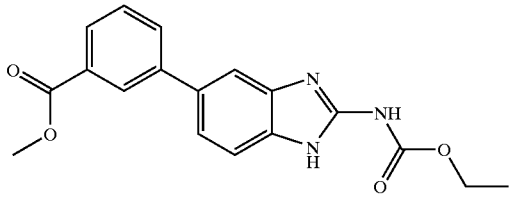 |
| 82 | 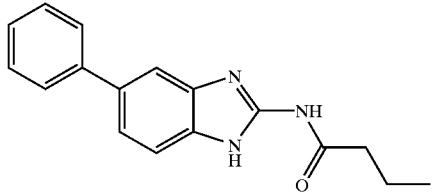 |
| 83 | 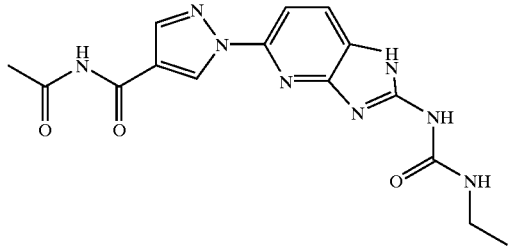 |
| 84 | 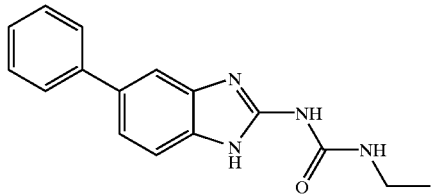 |
| 85 | 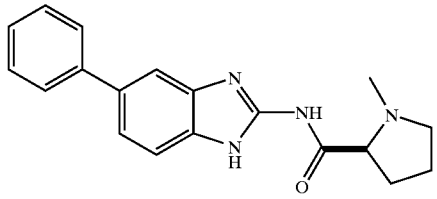 |

TABLE 1-continued
| No. Ia- | Structure |
|---|---|
| 86 | 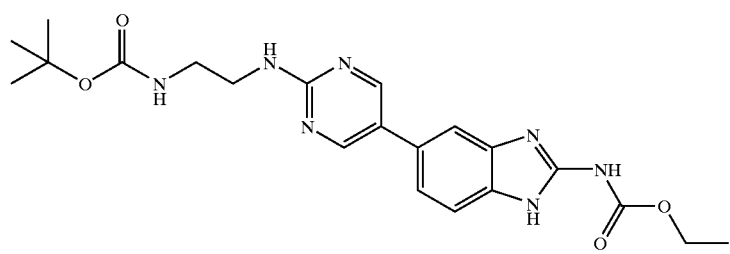 |
| 87 | 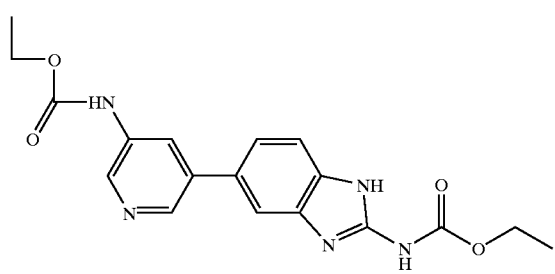 |
| 88 | 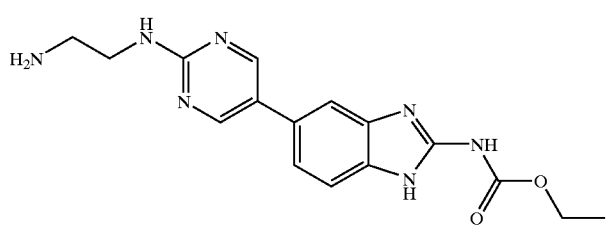 |
| 89 | 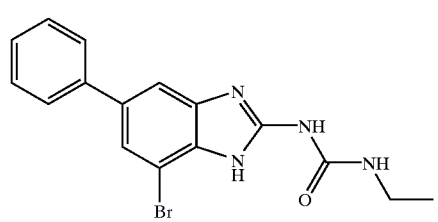 |
| 90 | 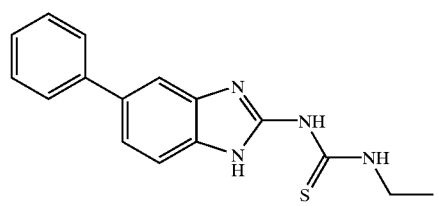 |
| 91 | 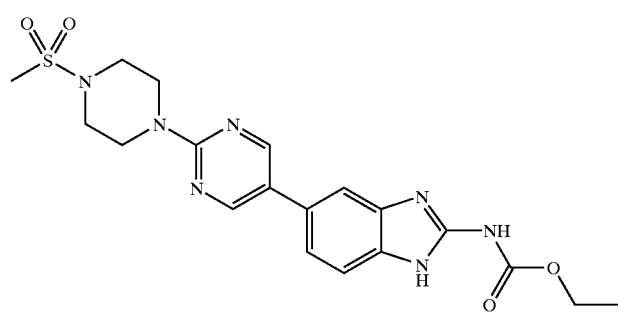 |

TABLE 1-continued
| No. Ia- | Structure |
|---|---|
| 92 | 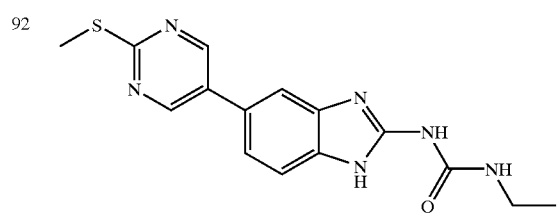 |
| 93 | 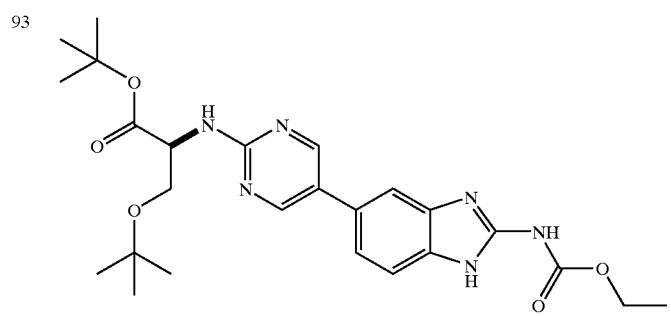 |
| 94 | 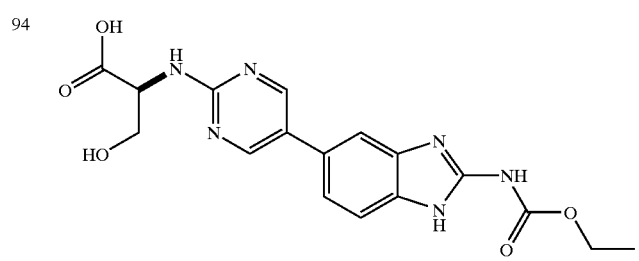 |
| 95 | 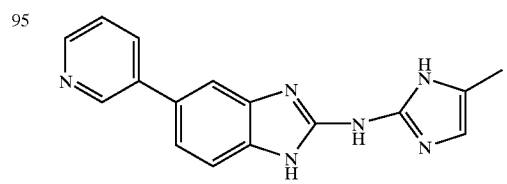 |
| 96 | 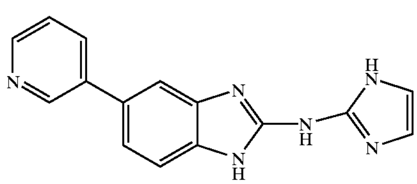 |
| 97 | 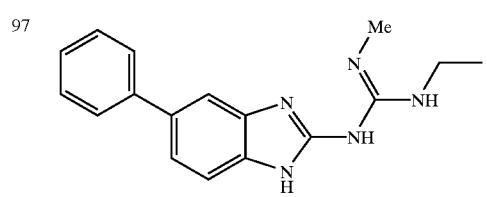 |

TABLE 1-continued
| No. Ia- | Structure |
|---|---|
| 98 | 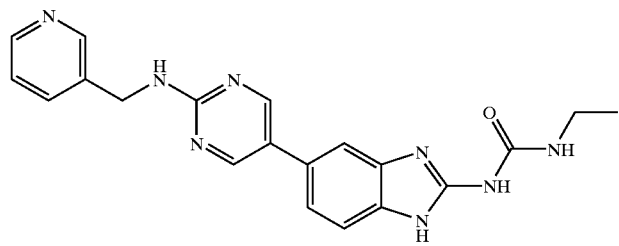 |
| 99 | 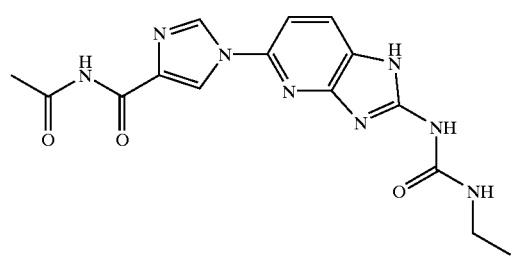 |
| 100 | 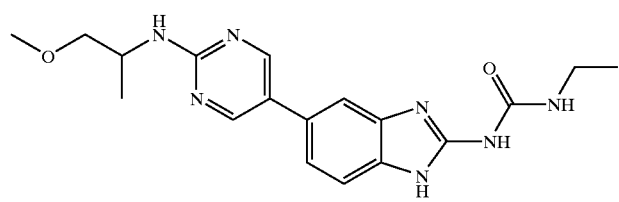 |
| 101 | 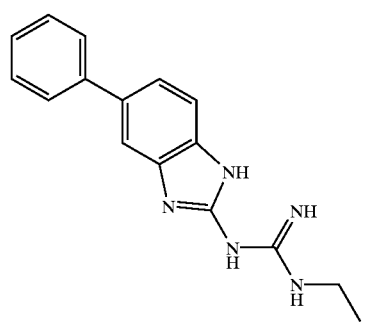 |
| 102 | 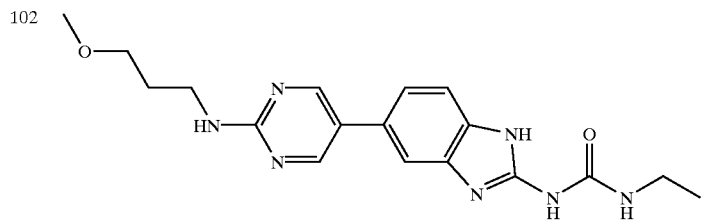 |

TABLE 1-continued
| No. Ia- | Structure |
| --- | --- |
| 103 | 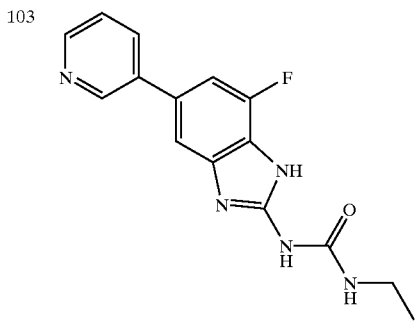 |
| 104 | 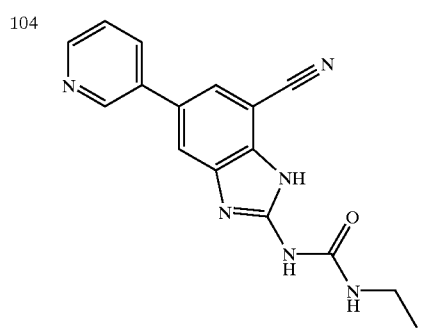 |
| 105 | 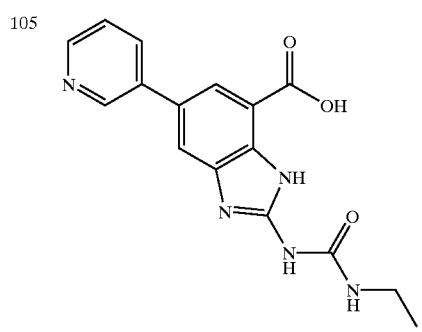 |
| 106 | 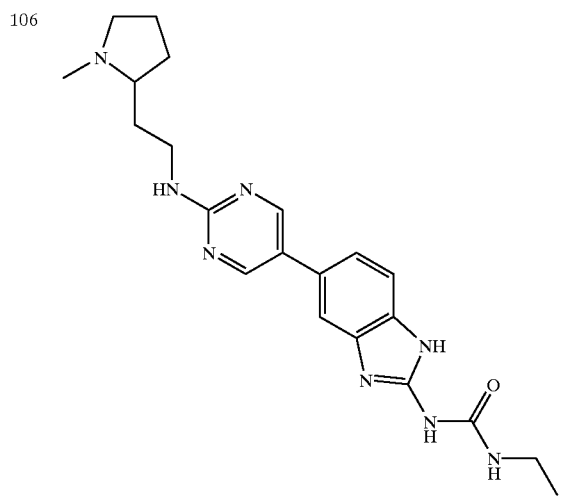 |

TABLE 1-continued
| No. Ia- | Structure |
|---|---|
| 107 | 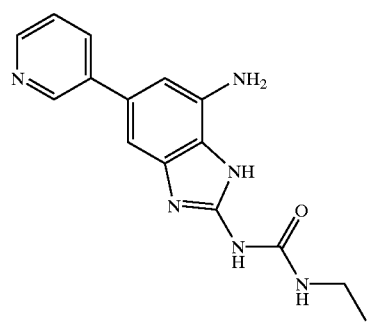 |
| 108 | 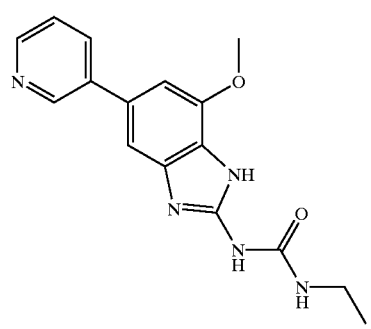 |
| 109 | 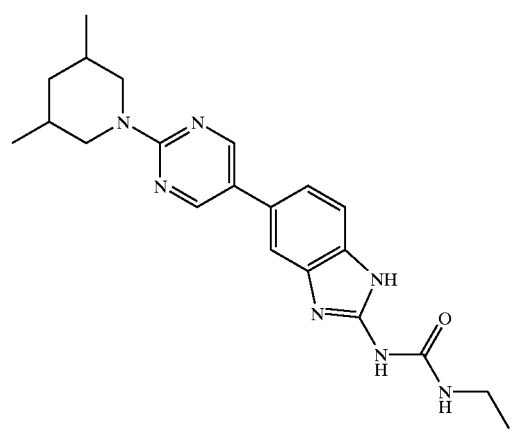 |
| 110 | 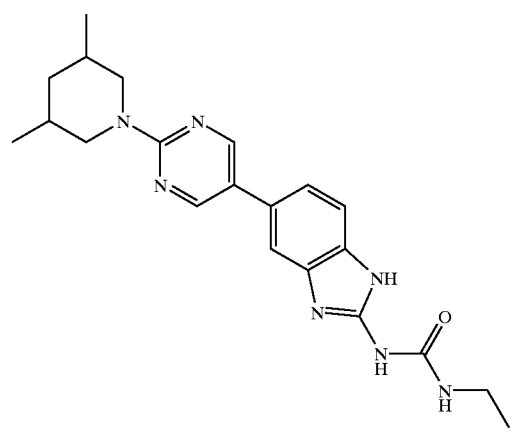 |

TABLE 1-continued
| No. Ia- | Structure |
|---|---|
| 111 | 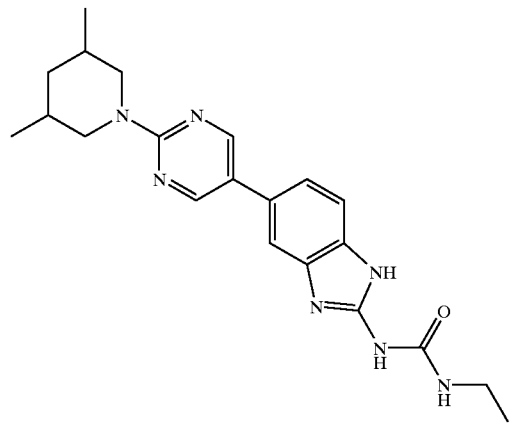 |
| 112 | 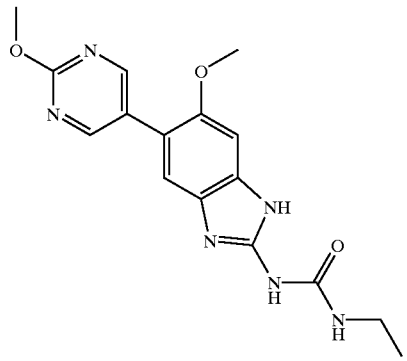 |
| 113 | 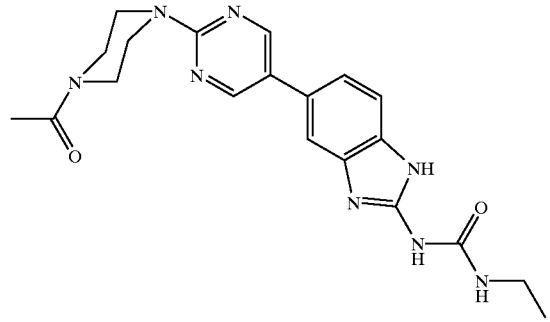 |
| 114 | 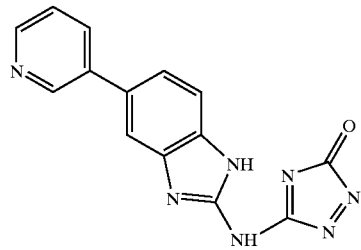 |
| 115 | 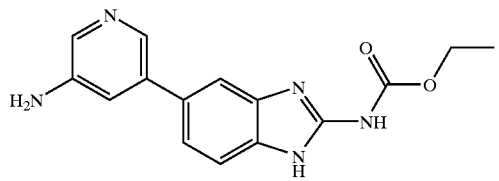 |

TABLE 1-continued
| No. Ia- | Structure |
|---|---|
| 116 | 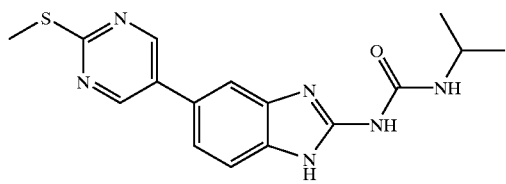 |
| 117 | 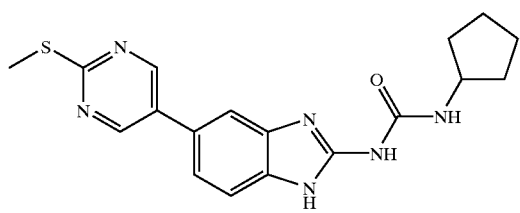 |
| 118 | 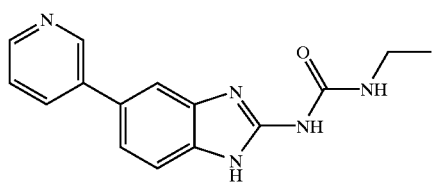 |
| 119 | 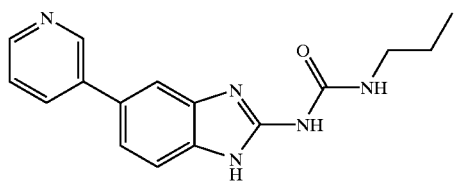 |
| 120 | 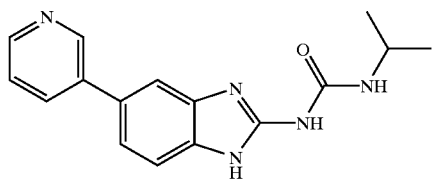 |
| 121 | 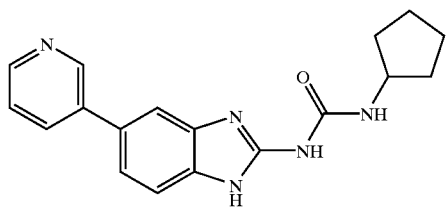 |
| 122 | 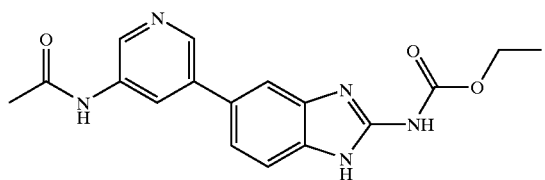 |

TABLE 1-continued
| No. Ia- | Structure |
| --- | --- |
| 123 | 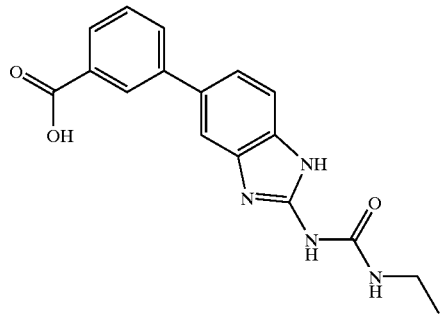 |
| 124 | 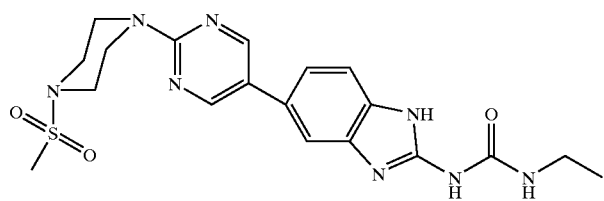 |
| 125 | 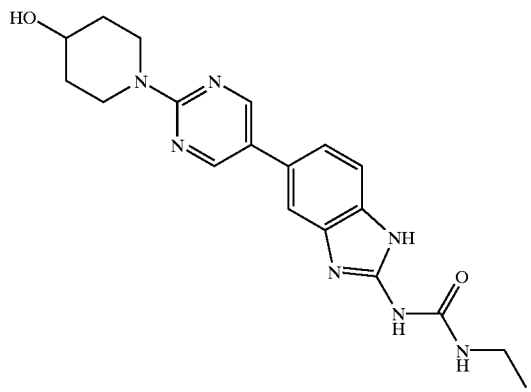 |
| 126 | 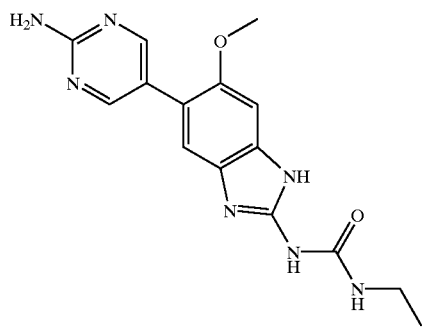 |

TABLE 1-continued
| No. Ia- | Structure |
|---|---|
| 127 | 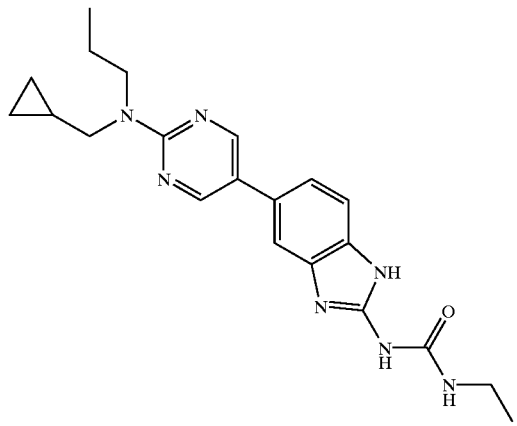 |
| 128 | 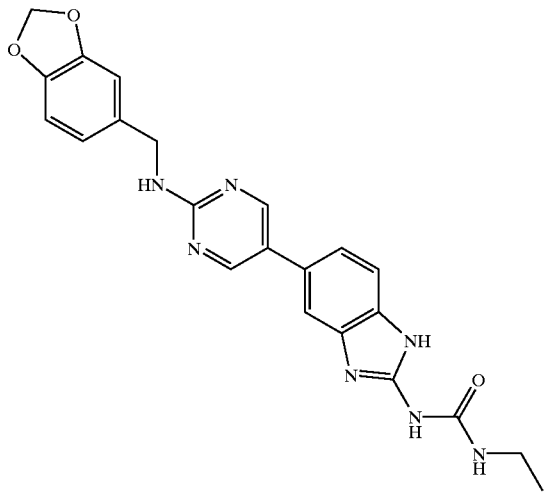 |
| 129 | 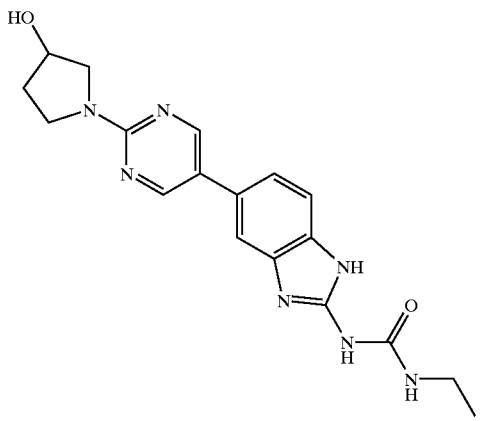 |

TABLE 1-continued
| No. Ia- | Structure |
|---|---|
| 130 | 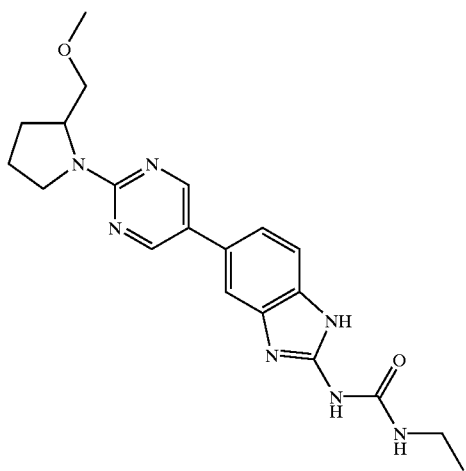 |
| 131 | 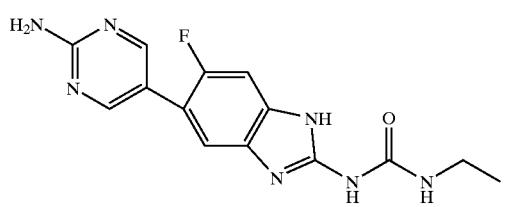 |
| 132 | 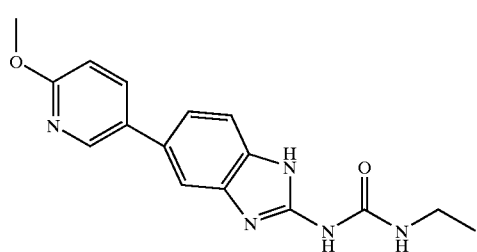 |
| 133 | 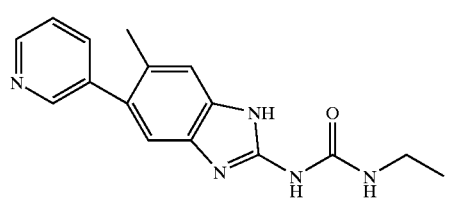 |
| 134 | 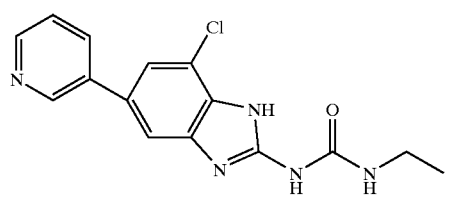 |

TABLE 1-continued
| No. Ia- | Structure |
|---|---|
| 135 | 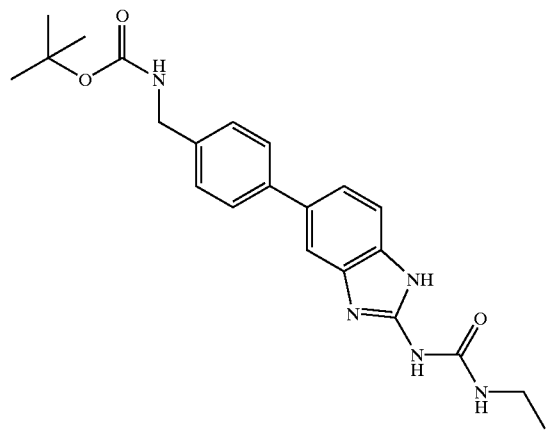 |
| 136 | 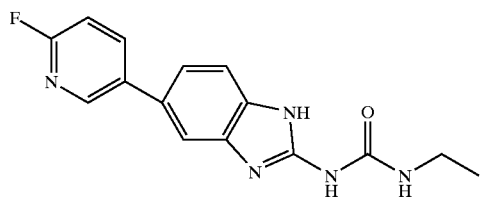 |
| 137 | 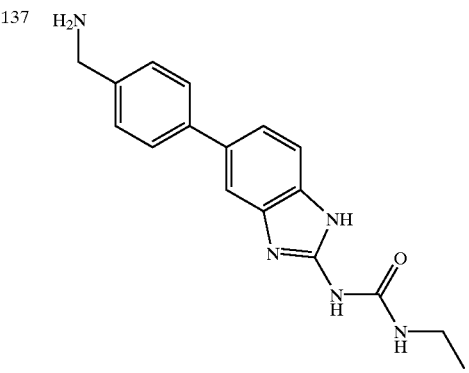 |
| 138 | 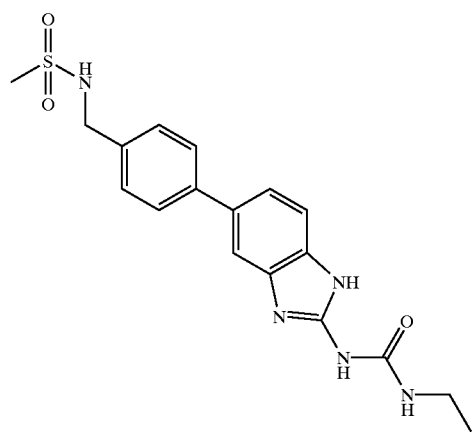 |

TABLE 1-continued
| No. Ia- | Structure |
|---|---|
| 139 | 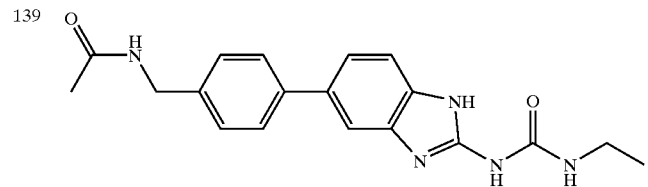 |
| 140 | 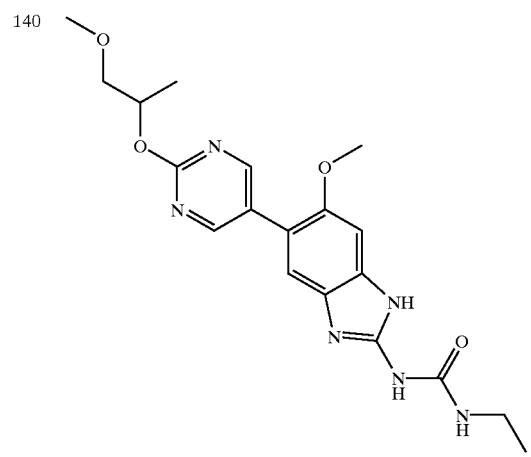 |
| 141 | 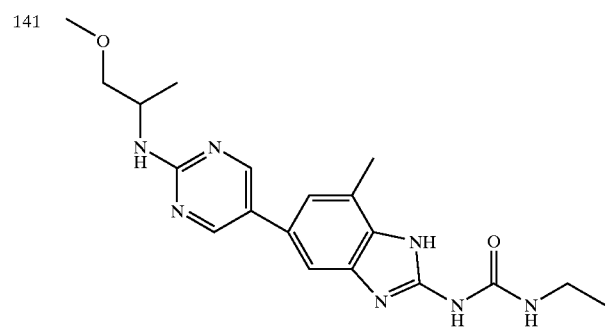 |
| 142 | 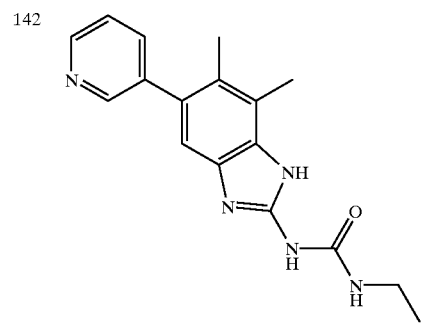 |
| 143 | 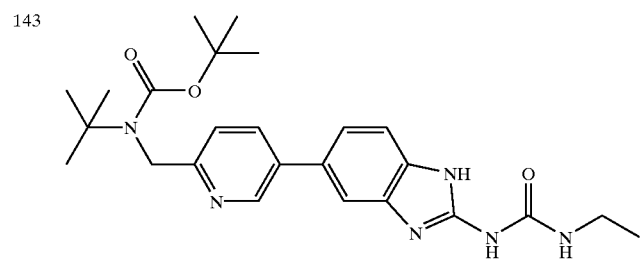 |

TABLE 1-continued
| No. Ia- | Structure |
|---|---|
| 144 | 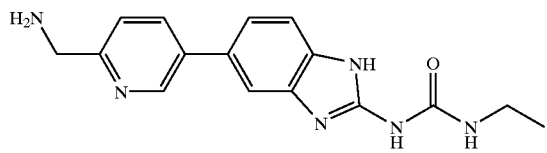 |
| 145 | 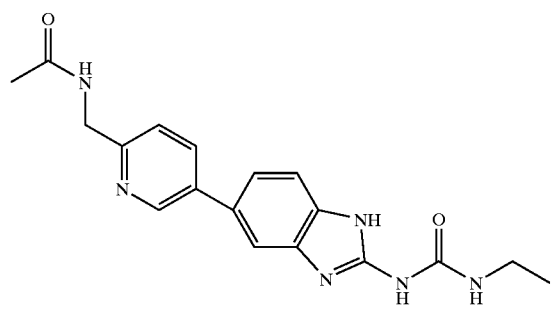 |
| 146 | 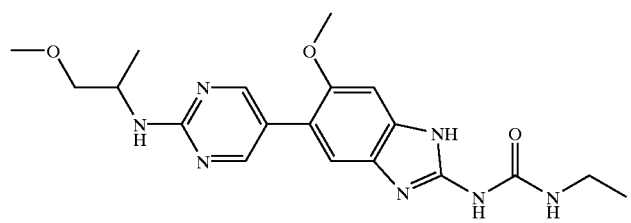 |
| 147 | 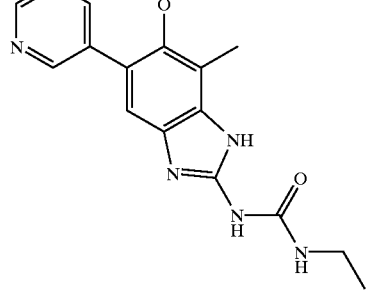 |
| 148 | 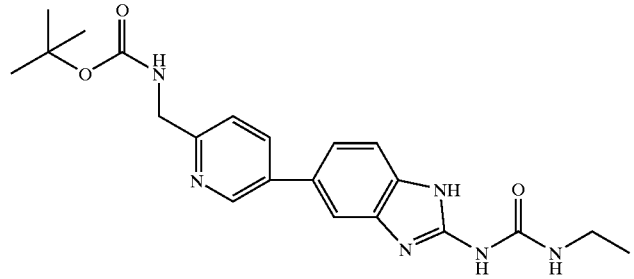 |

TABLE 1-continued
| No. Ia- | Structure |
|---|---|
| 149 | 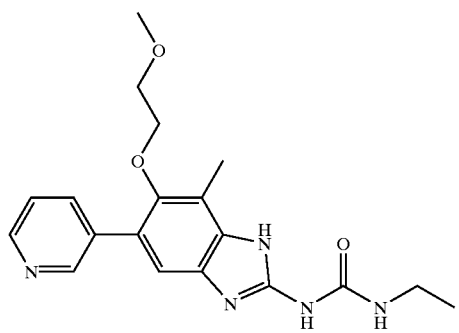 |
| 150 | 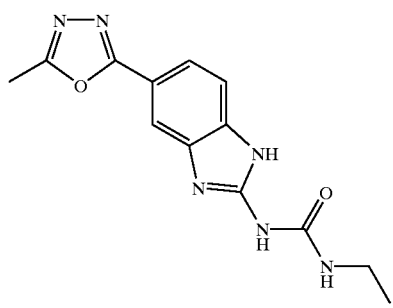 |
| 151 | 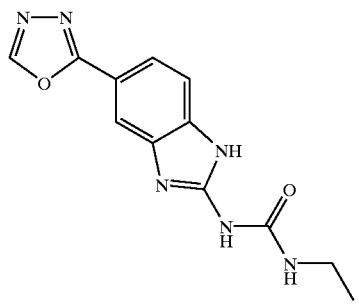 |
| 152 | 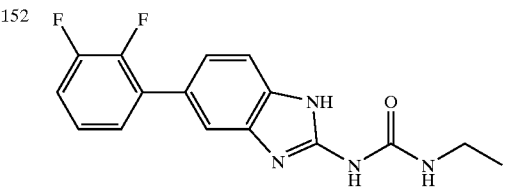 |
| 153 | 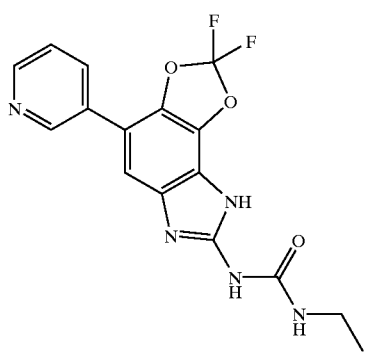 |

TABLE 1-continued
No. Ia- Structure
154 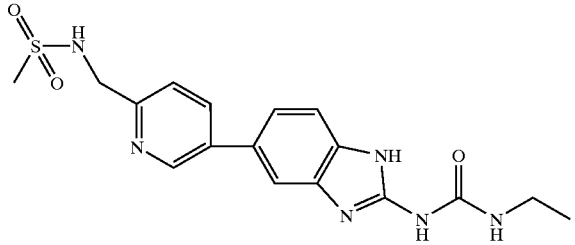
155 
156 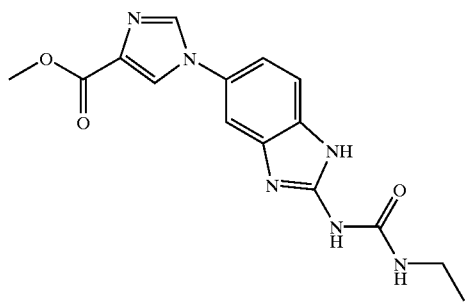
157 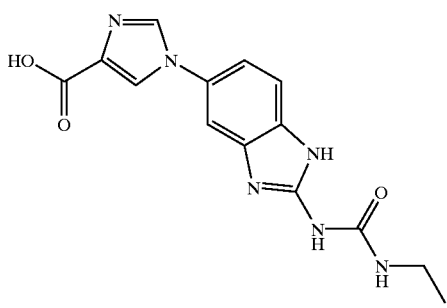
158 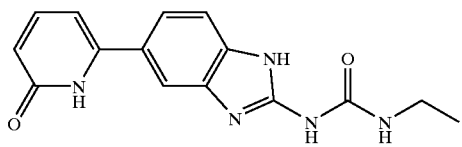
159 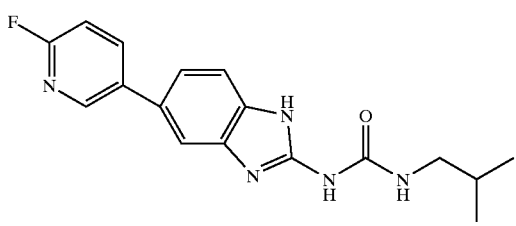

TABLE 1-continued
| No. Ia- | Structure |
|---|---|
| 160 | 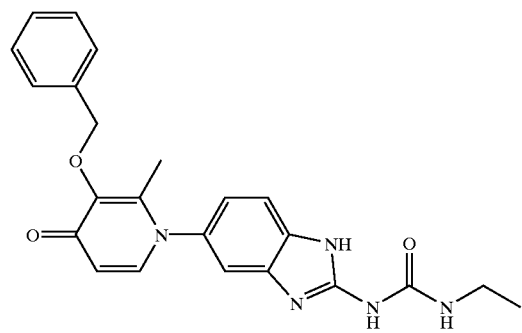 |
| 161 | 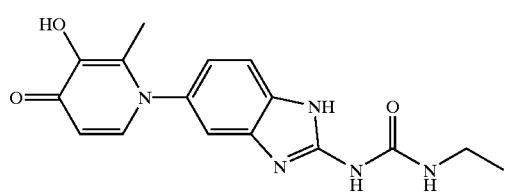 |
| 162 | 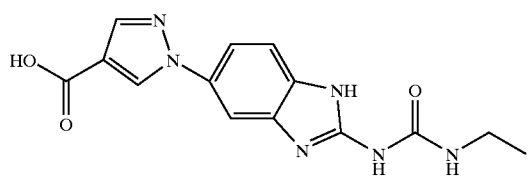 |
| 163 | 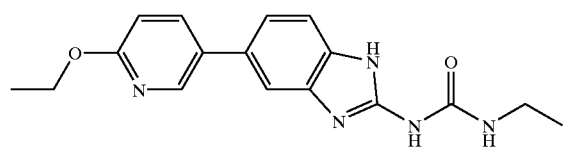 |
| 164 | 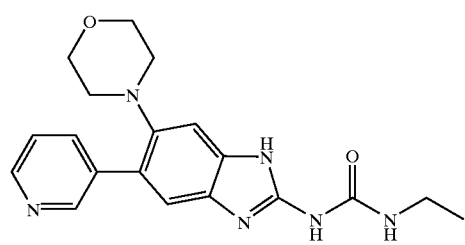 |
| 165 | 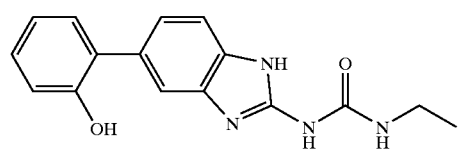 |
| 166 | 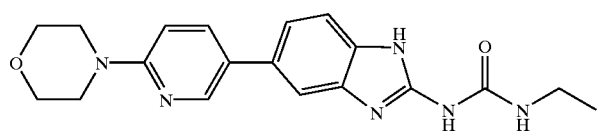 |

TABLE 1-continued
| No. Ia- | Structure |
|---|---|
| 167 | 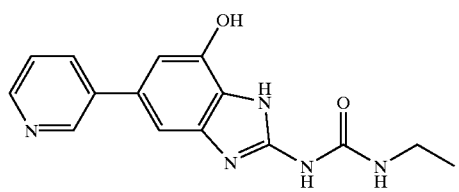 |
| 168 | 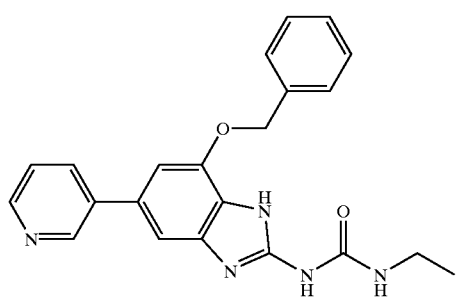 |
| 169 | 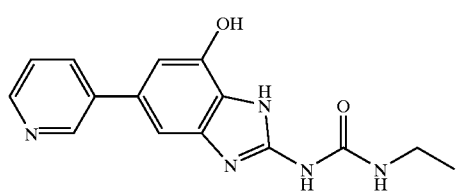 |
| 170 | 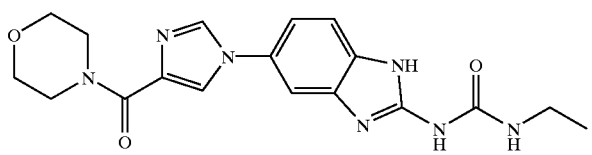 |
| 171 | 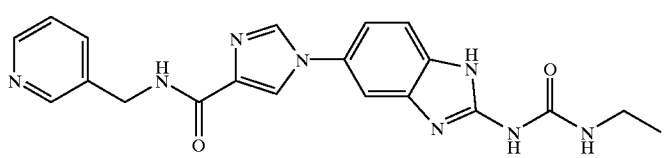 |
| 172 | 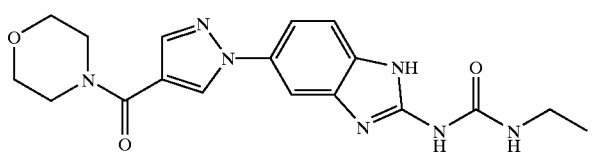 |
| 173 | 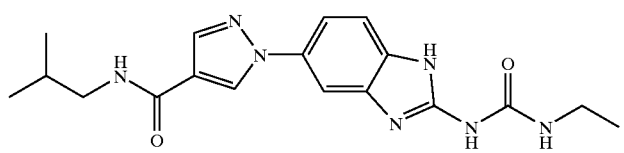 |
| 174 | 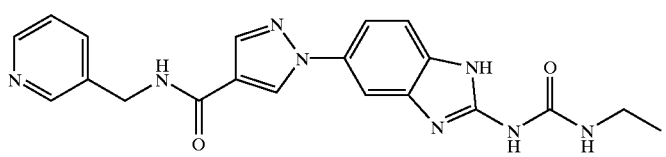 |

TABLE 1-continued
| No. Ia- | Structure |
|---|---|
| 175 | 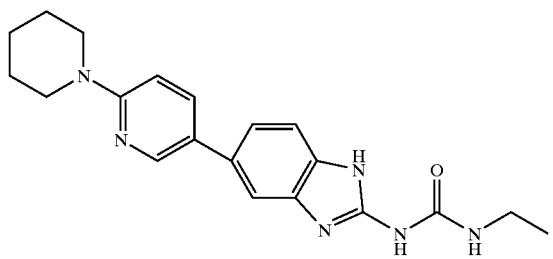 |
| 176 | 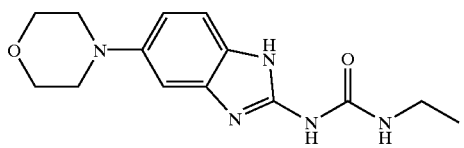 |
| 177 | 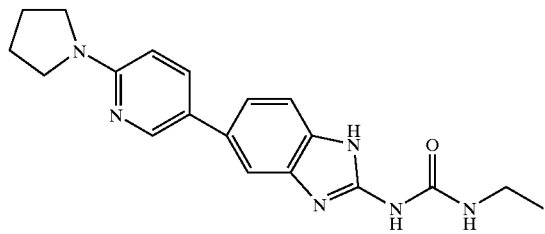 |
| 178 | 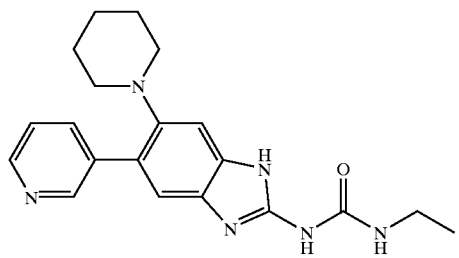 |
| 179 | 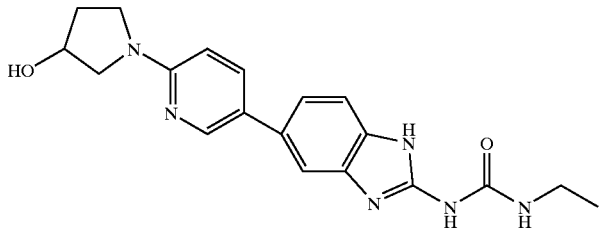 |
| 180 | 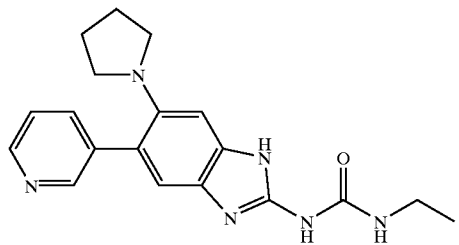 |
| 181 | 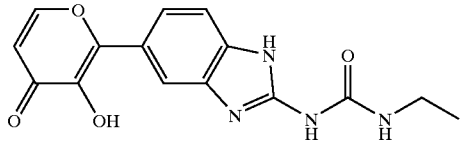 |

TABLE 1-continued
No. Ia- Structure
182 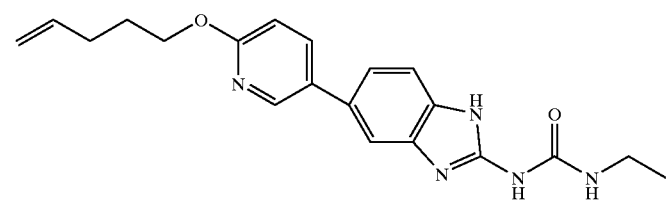
183 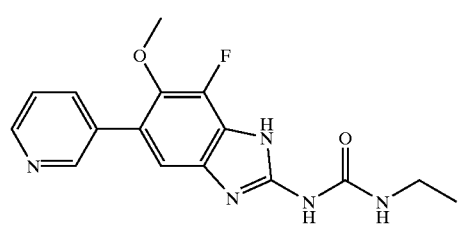
184 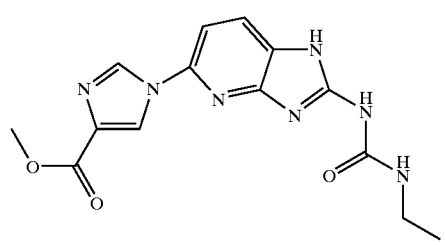
185 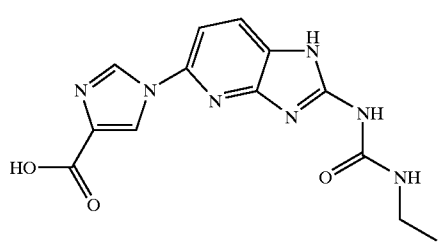
186 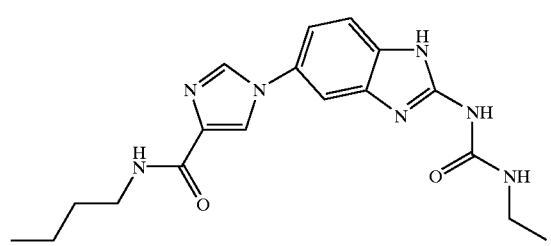
187 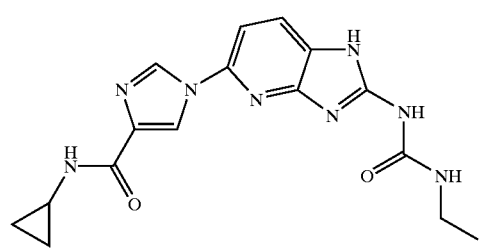

TABLE 1-continued
| No. Ia- | Structure |
|---|---|
| 188 | 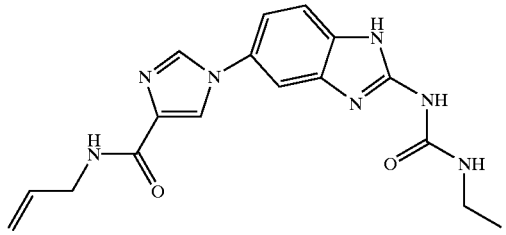 |
| 189 | 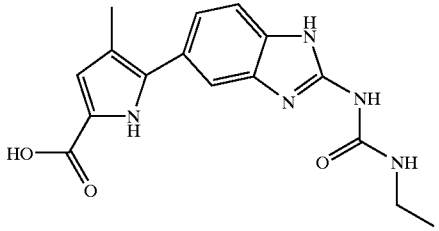 |
| 190 | 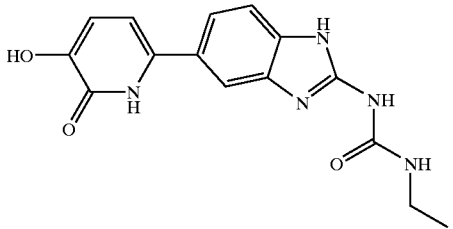 |
| 191 | 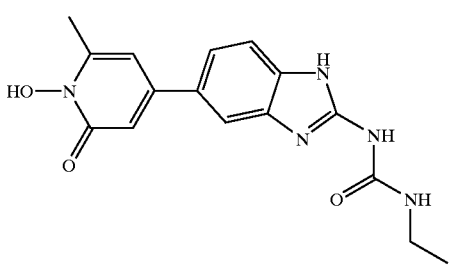 |
| 192 | 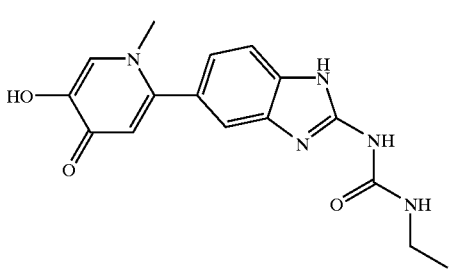 |
| 193 | 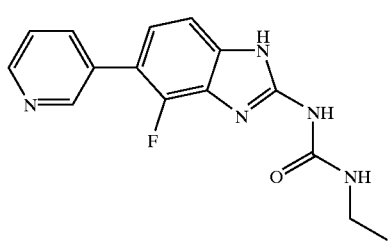 |

TABLE 1-continued
| No. Ia- | Structure |
|---|---|
| 194 | 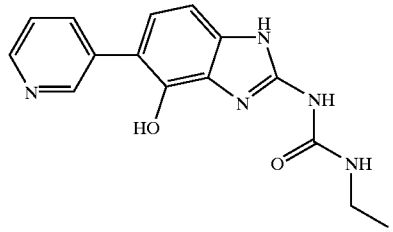 |
| 195 | 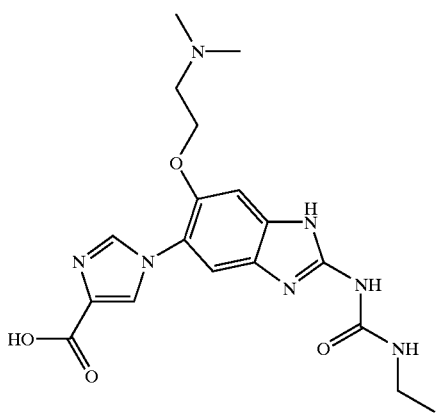 |
| 196 | 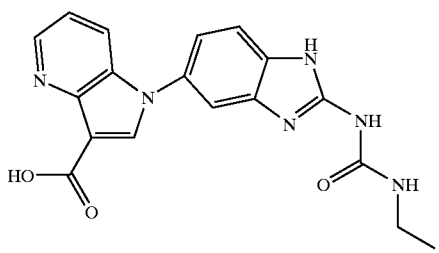 |
| 197 | 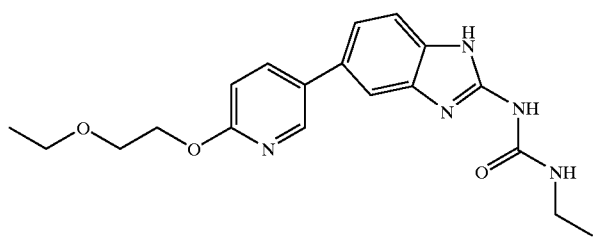 |
| 198 | 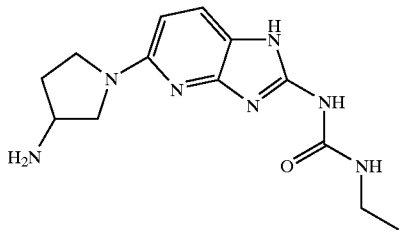 |

TABLE 1-continued
| No. Ia- | Structure |
|---|---|
| 199 | 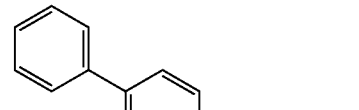 |
| 200 | 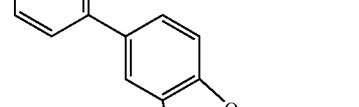 |
Selected compounds of formula Ib are shown in Table 2 below.
TABLE 2
| No. Ib- | Structure |
|---|---|
| 1 | 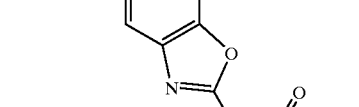 |
| 2 | 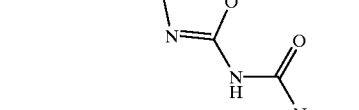 |
| 3 | 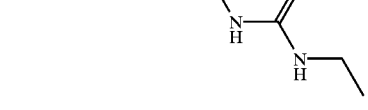 |
| 4 | |

TABLE 2-continued

| No. Ib- | Structure |
|---|---|
| 5 | (3-pyridyl)-7-bromo-benzoxazol-2-yl N-ethylurea |
| 6 | (5-pyrimidinyl)-7-bromo-benzoxazol-2-yl N-ethylurea |
| 7 | (3-pyridyl)-7-bromo-benzoxazol-2-yl N-cyclopentylurea |
| 8 | (2-amino-5-pyrimidinyl)-7-methyl-benzoxazol-2-yl N-ethylurea |
| 9 | (2-cyclopropylamino-5-pyrimidinyl)-7-methyl-benzoxazol-2-yl N-ethylurea |
| 10 | (2-benzylamino-5-pyrimidinyl)-benzoxazol-2-yl N-ethylurea |
| 11 | (1-imidazolyl)-7-methyl-benzoxazol-2-yl N-ethylurea |
| 12 | (1-pyrazolyl)-7-methyl-benzoxazol-2-yl N-ethylurea |

TABLE 2-continued

| No. Ib- | Structure |
|---|---|
| 13 | 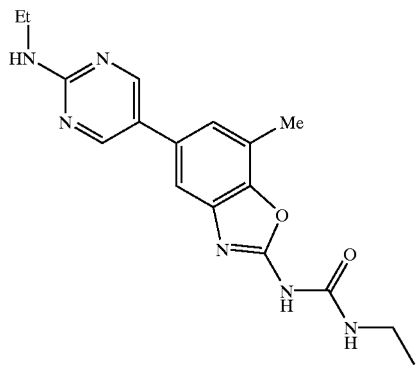 |
| 14 | 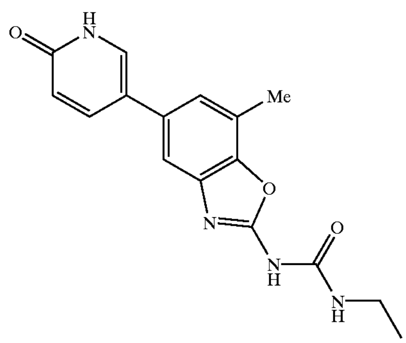 |
| 15 | 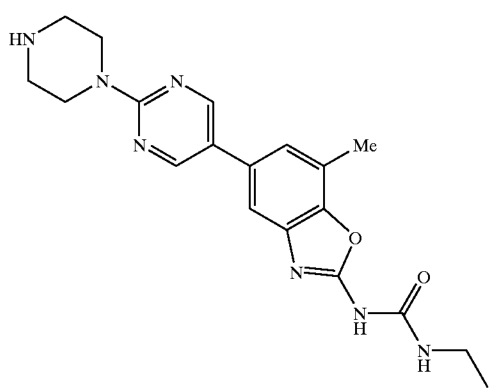 |
| 16 | 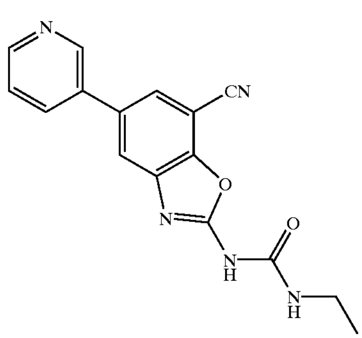 |
| 17 | |
| 18 | |
| 19 | |
| 20 | |

TABLE 2-continued

| No. Ib- | Structure |
|---|---|
| 21 | (pyridin-3-yl, CN-benzoxazole, urea-isopropyl) |
| 22 | (pyridin-3-yl, Me, CN-benzoxazole, urea-ethyl) |
| 23 | (HO₂C-imidazole, Me-benzoxazole, urea-ethyl) |
| 24 | (6-fluoropyridin-3-yl, benzoxazole, urea-ethyl) |
| 25 | (2-hydroxyphenyl, CN-benzoxazole, urea-ethyl) |
| 26 | (6-morpholinopyridin-3-yl, benzoxazole, urea-ethyl) |
| 27 | (2-NHAc-phenyl, CN-benzoxazole, urea-ethyl) |
| 28 | (phenyl, OH-benzoxazole, urea-ethyl) |

Another embodiment of this invention relates to compounds of formula IIa or IIb

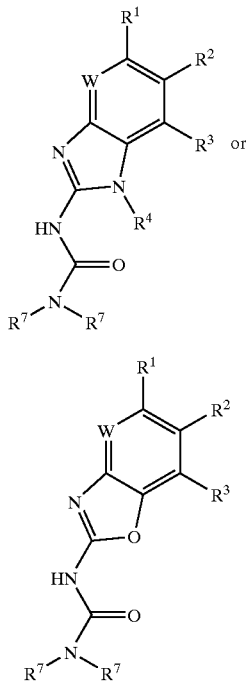

or a pharmaceutically acceptable derivative or prodrug thereof, wherein:

W is nitrogen or $CR^a$;

$R^a$ is selected from hydrogen, halogen, $-CF_3$, $R^7$, $-OR^7$, or $-N(R^7)_2$;

$R^1$ is an aryl or heteroaryl ring, wherein said ring is optionally substituted by up to four $R^9$; wherein an $R^9$ substituent in the ortho-position of $R^1$ taken together with $R^2$ may form a fused, unsaturated or partially unsaturated, optionally substituted 5–8 membered ring having 0–2 ring heteroatoms selected from nitrogen, oxygen, or sulfur;

$R^2$ and $R^3$ are each independently selected from $R^6$, halogen, CN, $SR^6$, $OR^6$, $N(R^6)_2$, $NRCO_2R^6$, $NRCON(R^6)_2$, $CON(R^6)_2$, $NRCOR^6$, $NRN(R^6)_2$, $COR^6$, $CO_2R^6$, $COCOR^6$, $SO_2R^6$, $SO_2N(R^6)_2$, or $NRSO_2R^6$; or $R^2$ and $R^3$ are taken together to form a fused, unsaturated or partially unsaturated, optionally substituted 5–8 membered ring containing 0–2 ring heteroatoms selected from nitrogen, oxygen, or sulfur;

$R^4$ is selected from $R^6$, $CON(R^6)$, $COR^6$, $CO_2R^6$, $COCOR^6$, $SO_2R^6$, $SO_2N(R^6)_2$, or $(CH_2)_yR^2$;

y is 1–6;

Ar is a five membered heteroaryl, heterocyclyl, or carbocyclyl ring, wherein said ring is optionally substituted by up to three substituents selected from oxo, halogen, CN, $NO_2$, $R^8$, $OR^8$, $NHR^8$, $NHCOR^8$, $NHCONHR^8$, $COR^8$, $CONHR^8$, $SO_2R^8$, $NHSO_2NHR^8$ or $SO_2NHR^8$;

each $R^6$ is independently selected from $R^7$ or an optionally substituted group selected from alkoxy, hydroxyalkyl, heterocyclyl, heterocyclylalkyl, aryl, aralkyl, aralkoxy, aryloxyalkyl, heteroaryl, heteroaralkyl, heteroaralkoxy, or heteroaryloxyalkyl;

each $R^7$ is independently selected from hydrogen or an optionally substituted aliphatic group having one to six carbons, or two $R^7$ on the same nitrogen taken together with the nitrogen optionally form a four to six member, saturated or unsaturated heterocyclic ring having one to three heteroatoms;

$R^8$ is a $C_1$–$C_4$ aliphatic group, wherein two $R^8$ on adjacent positions of Ar, or an aryl or heteroaryl ring, may be taken together with their intervening atoms to form a three to six membered fused ring;

each $R^9$ is independently selected from oxo, halogen, CN, $NO_2$, $T_n$(haloalkyl), $R^6$, $SR^6$, $OR^6$, $OR^8$, $N(R^6)_2$, $CON(R^6)_2$, $CON(R)COR^6$, $COR^6$, $CO_2R^6$, $CO_2N(R^6)_2$, $COCOR^6$, $SO_2R^6$, $SO_2N(R^6)_2$, $N(R)T_nCO_2R^6$, $N(R)T_nCON(R^6)_2$, $N(R)T_nN(R^6)_2$, $N(R)T_nNRCO_2R^6$, $N(R)T_nNRCON(R^6)_2$, $N(R)T_nCOR^6$, $N(R)T_nNRCOR^6$, $N(R)T_nSO_2N(R^6)_2$, $N(R)T_nSO_2R^6$, $T_nPO(OR^7)_2$, $T_nOPO(OR^7)_2$, $T_nSP(OR^7)_2$, $T_nPO(OR^7)_2$, or $T_nNPO(OR^7)_2$;

each Q is an independently selected $C_1$–$C_3$ branched or straight alkyl;

T is selected from $-Q-$ or $-Q_m-CH(Q_m-R^2)-$; and each m and n are independently selected from zero or one.

Examples of preferred $R^1$ include optionally substituted phenyl, 2-pyridyl, 3-pyridyl, 4-pyridyl, thienyl, pyrimidyl, imidazol-1-yl, imidazol-2-yl, pyrazol-1-yl, amino-pyrimidinyl, quinolinyl, aminobenzimidazole, and indolyl. Preferred $R^9$, if present, on the $R^1$ aryl or heteroaryl ring of formula IIa or IIb include halogen, CN, oxo, $R^6$, $SR^6$, $OR^6$, $N(R^6)_2$, $CON(R^6)_2$, $CO_2R^6$, $CON(R)COR^6$, and $N(R)T_nCO_2R^6$. Examples of such $R^9$ groups include, but are not limited to, pyrrol-2,5-dione, $NR_2$, OR, $CO_2H$, $NO_2$, OH, NHCOR, $NHCO_2R$, $NHCH_2CO_2R$, $NH(CH_2)_2NHCO_2R$, $CH_2CO_2R$, $CF_3$, $SO_2R$, $NHCH(CH_2OH)CO_2H$, $N-SO_2Me$-piperidinyl, SMe, $NH(CH_2)_2NH_2$, and piperidinyl.

Preferred $R^2$ and $R^3$ groups include halogen, CN, $CO_2R^6$, $OR^6$, and $R^6$. Examples of preferred $R^3$ groups include Br, F, Cl, COOH, CN, OMe, methyl, ethyl, t-butyl, $CF_3$, OH, and OBn.

Preferred compounds of formulae IIa and IIb include those having one or more, or most preferably all, of the features selected from the group consisting of:

(a) $R^1$ is an optionally substituted aryl or heteroaryl ring;

(b) $R^2$ and $R^3$ are each independently selected from halogen, CN, $CO_2R^6$, $OR^6$, or $R^6$;

(c) $R^9$ is halogen, CN, oxo, $R^6$, $SR^6$, $OR^6$, $N(R^6)_2$, $CON(R^6)_2$, $CO_2R^6$, $CON(R)COR^6$, $N(R)T_nCO_2R^6$, $N(R)T_nNRCO_2R^6$, $N(R)T_nN(R^6)_2$, $NO_2$, $T_n$(haloalkyl), $CO_2N(R^6)_2$, $COR^6$, $SO_2R^6$, or $SO_2N(R^6)_2$.

More preferred compounds of formula IIa and IIb include those having one or more, or most preferably all, of the features selected from the group consisting of:

(a) $R^1$ is an optionally substituted ring selected from phenyl, 2-pyridyl, 3-pyridyl, 4-pyridyl, thienyl, pyrimidyl, imidazol-1-yl, imidazol-2-yl, pyrazol-1-yl, amino-pyrimidinyl, quinolinyl, aminobenzimidazole, or indolyl;

(b) $R^2$ is hydrogen, alkoxy, aminoalkyl, or halogen;

(c) $R^3$ is hydrogen, alkoxy, aralkoxy, or halogen;

(d) $R^4$ is hydrogen or $(CH_2)_yR^2$; and (e) $R^9$ is halogen, CN, oxo, $R^6$, $SR^6$, $OR^6$, $N(R^6)_2$, $CON(R^6)_2$, $CO_2R^6$, $CON(R)COR^6$, or $N(R)T_nCO_2R^6$.

Another embodiment of this invention relates to compounds of formula IIIa or IIIb:

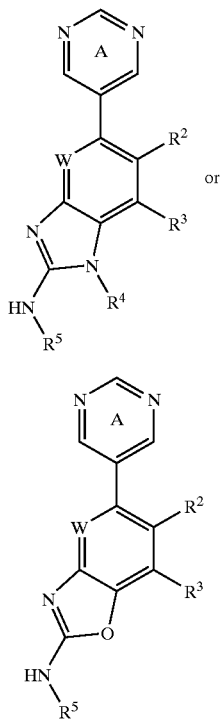

IIIa

IIIb or a pharmaceutically acceptable derivative or prodrug thereof, wherein:

W is nitrogen or $CR^a$;

$R^a$ is selected from hydrogen, halogen, $-CF_3$, $R^7$, $-OR^7$, or $-N(R^7)_2$;

Ring A is optionally substituted with up to three $R^9$; wherein when an $R^9$ substituent is in the ortho-position of Ring A, said $R^9$ substituent may be taken together with $R^2$ to form an optionally substituted 5–7 membered ring containing 0–2 ring heteroatoms selected from nitrogen, oxygen, or sulfur;

$R^2$ and $R^3$ are each independently selected from $R^6$, halogen, CN, $SR^6$, $OR^6$, $N(R^6)_2$, $NRCO_2R^6$, $NRCON(R^6)_2$, $CON(R^6)_2$, $NRCOR^6$, $NRN(R^6)_2$, $COR^6$, $CO_2R^6$, $COCOR^6$, $SO_2R^6$, $SO_2N(R^6)_2$, or $NRSO_2R^6$; or $R^2$ and $R^3$ are taken together to form a fused, unsaturated or partially unsaturated, optionally substituted 5–8 membered ring containing 0–2 ring heteroatoms selected from nitrogen, oxygen, or sulfur;

$R^4$ is selected from $R^6$, $CON(R^6)$, $COR^6$, $CO_2R^6$, $COCOR^6$, $SO_2R^6$, $SO_2N(R^6)_2$, or $(CH_2)_yR^2$;

y is 1–6;

$R^5$ is selected from $R^7$, Ar, COAr, $CON(R^7)Ar$, $(CH_2)_yCO_2R^6$, $(CH_2)_yN(R^7)_2$, $C(=NR^{10})-N(R^7)_2$, $C(=NR^{10})-NRCOR$, $C(=S)-N(R^7)_2$, $CON(R^7)_2$, COR, $SO_2R$, or $SO_2N(R^7)_2$;

Ar is a five membered heteroaryl, heterocyclyl, or carbocyclyl ring, wherein said ring is optionally substituted by up to three substituents selected from oxo, halogen, CN, $NO_2$, $R^8$, $OR^8$, $NHR^8$, $NHCOR^8$, $NHCONHR^8$, $COR^8$, $CONHR^8$, $SO_2R^8$, $NHSO_2NHR^8$ or $SO_2NHR^8$;

each $R^6$ is independently selected from $R^7$ or an optionally substituted group selected from alkoxy, hydroxyalkyl, heterocyclyl, heterocyclcylalkyl, aryl, aralkyl, aralkoxy, aryloxyalkyl, heteroaryl, heteroaralkyl, heteroaralkoxy, or heteroarayloxyalkyl;

each $R^7$ is independently selected from hydrogen or an optionally substituted aliphatic group having one to six carbons, or two $R^7$ on the same nitrogen taken together with the nitrogen optionally form a four to six member, saturated or unsaturated heterocyclic ring having one to three heteroatoms;

$R^8$ is a $C_1$-$C_4$ aliphatic group, wherein two $R^8$ on adjacent positions of Ar, or an aryl or heteroaryl ring, may be taken together with their intervening atoms to form a three to six membered fused ring;

each $R^9$ is independently selected from oxo, halogen, CN, $NO_2$, $T_n$(haloalkyl), $R^6$, $SR^6$, $OR^6$, $OR^8$, $N(R^6)_2$, $CON(R^6)_2$, $CON(R)COR^6$, $COR^6$, $CO_2R^6$, $CO_2N(R^6)_2$, $COCOR^6$, $SO_2R^6$, $SO_2N(R^6)_2$, $N(R)T_nCO_2R^6$, $N(R)T_nCON(R^6)_2$, $N(R)T_nN(R^6)_2$, $N(R)T_nNRCO_2R^6$, $N(R)T_nNRCON(R^6)_2$, $N(R)T_nCOR^6$, $N(R)T_nNRCOR^6$, $N(R)T_nSO_2N(R^6)_2$, $N(R)T_nSO_2R^6$, $T_nPO(OR^7)_2$, $T_nOPO(OR^7)_2$, $T_nSP(OR^7)_2$, $T_nPO(OR^7)_2$, or $T_nNPO(OR^7)_2$;

each Q is an independently selected $C_1$-$C_3$ branched or straight alkyl;

T is selected from $-Q-$ or $-Q_m-CH(Q_m-R^2)-$;

each m and n are independently selected from zero or one;

and $R^{10}$ is selected from $R^7$ or Ar.

Preferred $R^9$, if present, on Ring A of formulae IIIa and IIIb include halogen, CN, oxo, $R^6$, $SR^6$, $OR^6$, $N(R^6)_2$, $CON(R^6)_2$, $CO_2R^6$, $CON(R)COR^6$, and $N(R)T_nCO_2R^6$. Examples of such $R^9$ groups include, but are not limited to, pyrrol-2,5-dione, $NR_2$, OR, $CO_2H$, $NO_2$, OH, NHCOR, $NHCO_2R$, $NHCH_2CO_2R$, $NH(CH_2)_2NHCO_2R$, $CH_2CO_2R$, $CF_3$, $SO_2R$, $NHCH(CH_2OH)CO_2H$, $N-SO_2Me$-piperidinyl, SMe, $NH(CH_2)_2NH_2$, and piperidinyl.

Preferred $R^2$ and $R^3$ groups include halogen, CN, $CO_2R^6$, $OR^6$, and $R^6$. Examples of preferred $R^3$ groups include Br, F, Cl, COOH, CN, OMe, methyl, ethyl, t-butyl, $CF_3$, OH, and OBn.

Examples of preferred $R^5$ include $CO_2$(aliphatic), $C(=NH)-NH_2$, and $CON(R^7)_2$ such as CO(piperidin-1-yl), CONHEt, CONHMe, CONH(cyclopropyl), CONH(isopropyl), CONH(propyl), CONH(pyrrolidinyl), $CO_2Et$, and $CO_2Me$.

Preferred compounds of formulae IIIa and IIIb include those having one or more, or most preferably all, of the features selected from the group consisting of:

(a) $R^2$ and $R^3$ are each independently selected from halogen, CN, $CO_2R^6$, $OR^6$, or $R^6$;

(b) $R^5$ is $CO_2R$, COAr, COR, $CON(R^7)_2$, Ar, $(CH_2)_yCO_2R$, or $(CH_2)_yN(R^7)_2$; and (c) $R^9$ is halogen, CN, oxo, $R^6$, $SR^6$, $OR^6$, $N(R^6)_2$, $CON(R^6)_2$, $CO_2R^6$, $CON(R)COR^6$, $N(R)T_nCO_2R^6$, $N(R)T_nNRCO_2R^6$, $N(R)T_nN(R^6)_2$, $NO_2$, $T_n$(haloalkyl), $CO_2N(R^6)_2$, $COR^6$, $SO_2R^6$, or $SO_2N(R^6)_2$.

More preferred compounds of formula IIIa and IIIb include those having one or more, or most preferably all, of the features selected from the group consisting of:

(a) $R^2$ is hydrogen, alkoxy, aminoalkyl, or halogen;

(b) $R^3$ is hydrogen, alkoxy, aralkoxy, or halogen;

(c) $R^4$ is hydrogen or $(CH_2)_yR^2$;

(d) $R^5$ is $CON(R^7)_2$, Ar, $(CH_2)_yCO_2R$, or $(CH_2)_yN(R^7)_2$; and (e) $R^9$ is halogen, CN, oxo, $R^6$, $SR^6$, $OR^6$, $N(R^6)_2$, $CON(R^6)_2$, $CO_2R^6$, $CON(R)COR^6$, or $N(R)T_nCO_2R^6$.

The compounds of this invention may be prepared in general by methods known to those skilled in the art for analogous compounds, as illustrated by the general Schemes

Scheme I

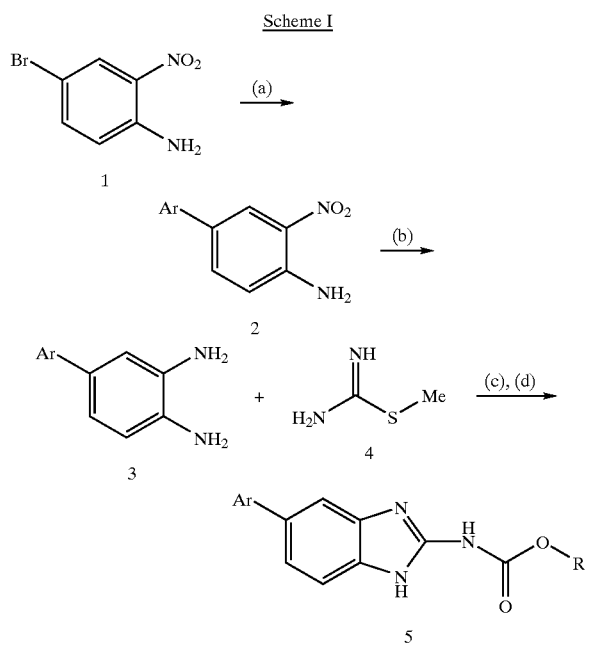

Reagents and conditions: (a) Ar-boronic acid, PdCl$_2$(dppf), K$_3$PO$_4$, DMF, 95° C., 18 hours; (b) 40 psi H$_2$, 10% Pd/C, EtOAc; (c) ROCOCl, NaOH, H$_2$O, 0° C.; (d) p-TsOH, ROH, reflux, 1 hour.

The compounds 2 are prepared by treating a solution of 4-bromo-2-nitroaniline (1) in DMF with an arylboronic acid (1.2 equivalents), potassium phosphate (1.3 equivalents), and dichloro-(diphenylphosphinoferrocene)palladium (0.1 equivalent). The resulting mixture is heated at 95° C. for 18 hours then cooled to room temperature and diluted with ethyl acetate. The crude product is isolated by aqueous work-up then concentrated in vacuo. The concentrate is purified by silica gel chromatography to afford 2. A wide variety of substitutions on the aryl ring are amenable to this reaction. Examples of suitable substituted and unsubstituted aryl groups include, but are not limited to, those set forth in Table 1 above.

Compound 3 is prepared by treating a solution of 2 in ethyl acetate with 10% palladium on carbon (0.1 g/mmol) and the resulting suspension hydrogenated at 40 psi while shaking at ambient temperature for 2 hours. The catalyst is removed by filtration and the filtrate concentrated in vacuo to afford 3.

Compounds of formula 5 are prepared by first preparing a solution of 2-methyl-2-thiopseudourea (4, 1 equivalent) and alkylchloroformate (2 equivalents) in water at 0° C. To this solution is added 25% aqueous sodium hydroxide in a dropwise fashion over 1 hour until the pH stabilized at 8. Acetic acid is then added to achieve pH 5 then sodium acetate trihydrate (1 eauivalent) and a solution of 3 (1 equivalent) in ROH are added. p-Toluenesulfonic acid (catalytic amount) is added and the resulting mixture heated at reflux for 1 hour. The reaction mixture is then cooled to ambient temperature and diluted with ethyl acetate. After aqueous work-up, the crude product is purified by preparative HPLC to afford 5.

Scheme II

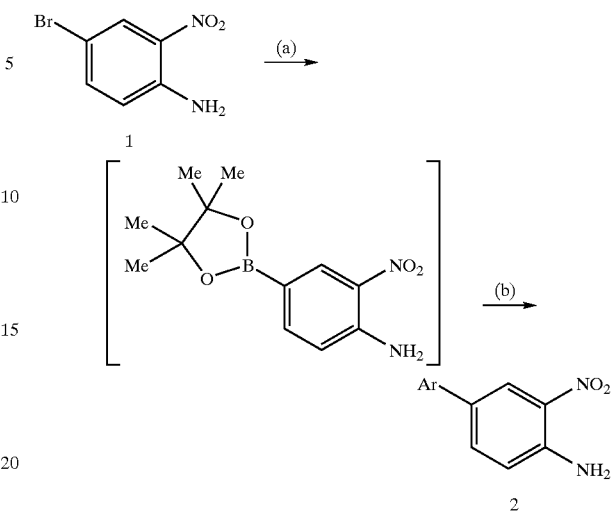

Reagents and conditions: (a) bis(pinacolato)diboron, KOAc, PdCl$_2$(dppf), DMSO, 80° C.; (b) ArBr, K$_3$PO$_4$, PdCl$_2$(dppf), DMSO, 95° C;

Scheme II above shows an alternative method for preparing compound 2. Starting material 1 (1 equivalent) is combined with bis(pinacolato)diboron (1.2 equivalents), PdCl$_2$(dppf) (0.1 equivalent), and KOAc (3 equivalents) in DMSO, and the resulting mixture is heated at 80° C. for 18 hours. The reaction mixture is cooled to ambient temperature then the aryl bromide (1.1 equivalents) is added followed by the further addition of K$_3$PO$_4$ (3 equivalents) and PdCl$_2$(dppf) (0.1 equivalent). The resulting mixture is heated at 95° C. for another 72 hours then allowed to cool to room temperature. Purification by chromatography affords compound 2.

Scheme III

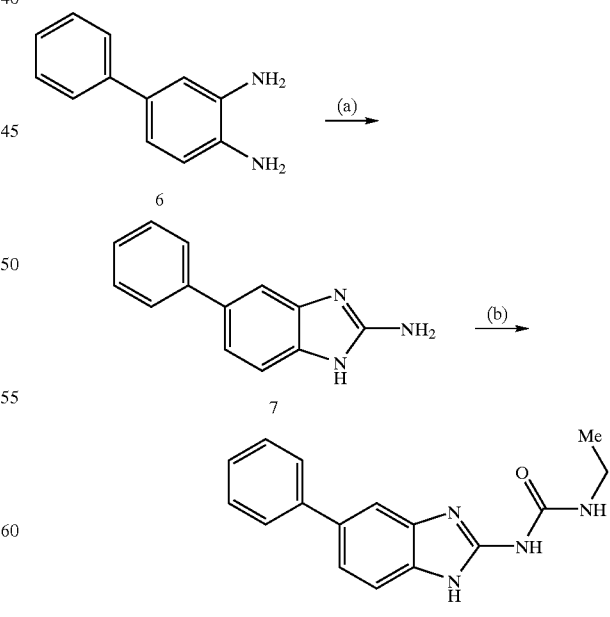

Reagents and conditions: (a) BrCN, THF, MeOH, water, room temperature; (b) EtNCO, THF, reflux.

Using the preparation of compound number Ia-84 to illustrate, Scheme III above shows the general method used for preparing compounds of formula IIa. Starting material 6 is prepared according to the method described in Scheme I at steps (a) and (b). Compound 7 is prepared by treating 6 with cyanogen bromide in acetonitrile at room temperature over night. Aqueous work-up affords 7. Compound Ia-84 is prepared from 7 by treating with ethyl isocyanate in THF at reflux over night. The crude product is purified by preparative chromatography to afford Ia-84.

Using the preparation of compound number Ia-86 to illustrate, Scheme IV above shows a general method that may be used for preparing compounds of formula IIIa. Compound 10 is prepared from 5-bromo-2-chloropyrimidine (8) and N-Boc-ethylenediamine (9) by heating a mixture of 8 and 9 in ethanol at 80° C. for 4 hours. Compound 12 is prepared from 10 and 11 according to the method described in Scheme II. Compound 12 is used to prepare Ia-86 via steps (c) and (d) according to steps (b) and (c) of Scheme I.

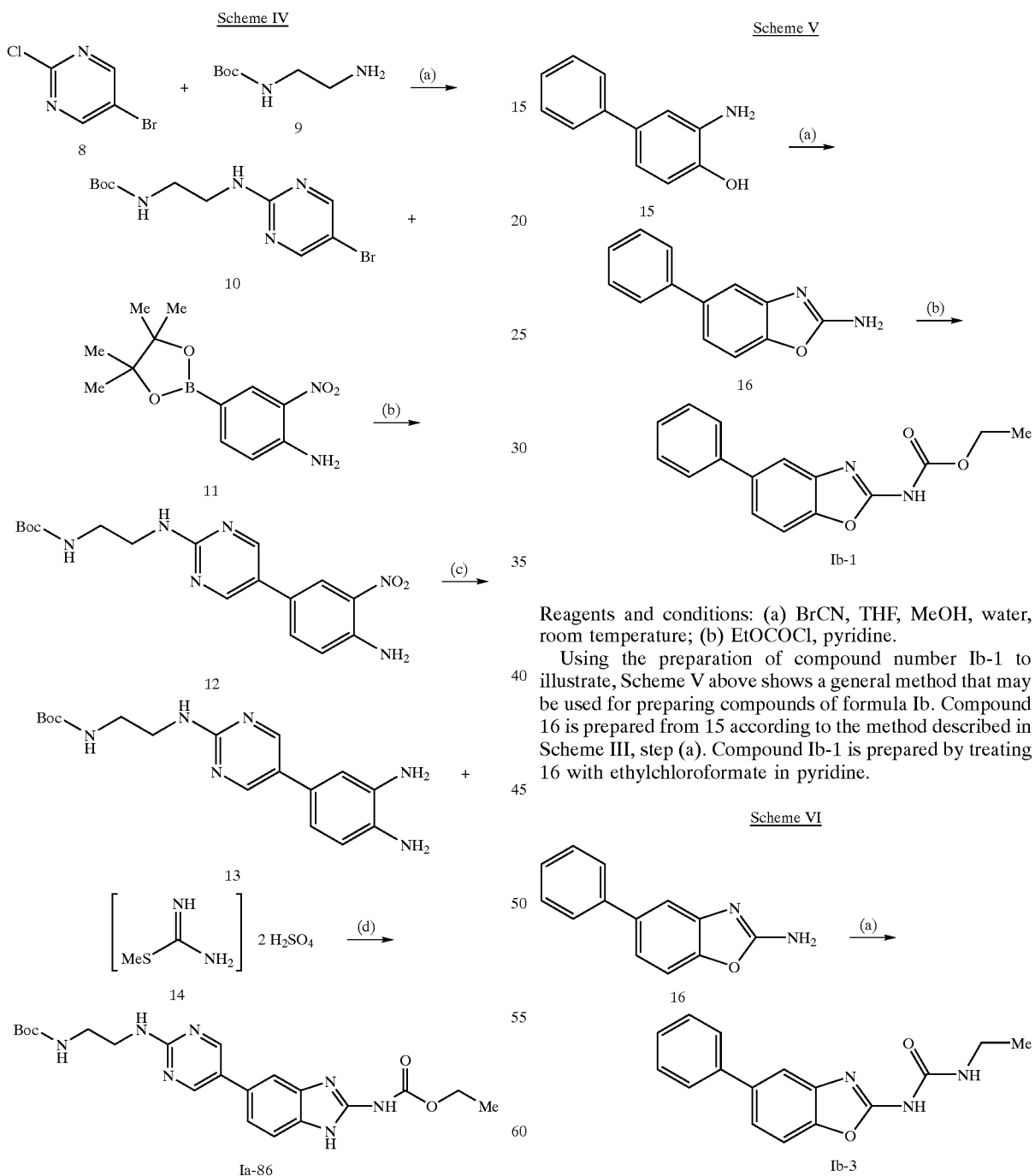

Reagents and conditions: (a) BrCN, THF, MeOH, water, room temperature; (b) EtOCOCl, pyridine.

Using the preparation of compound number Ib-1 to illustrate, Scheme V above shows a general method that may be used for preparing compounds of formula Ib. Compound 16 is prepared from 15 according to the method described in Scheme III, step (a). Compound Ib-1 is prepared by treating 16 with ethylchloroformate in pyridine.

Reagents and conditions: (a) EtOH, 80° C., 4 hours; (b) PdCl₂(dppf), K₃PO₄, 95° C., 48 hours; (c) Pd/C, H₂, 50 psi, 6 hours; (d) 2-methyl-2-thiopseudourea (14), EtOCOCl, 80° C., 18 hours.

Reagents and conditions: (a) (b) EtNCO, THF, reflux.

Using the preparation of compound number Ib-3 to illustrate, Scheme VI above shows a general method that may be used for preparing compounds of formula IIb.

Compound 16 is treated ethyl isocyanate in THF at reflux according to Scheme III step, (b) to afford Ib-3.

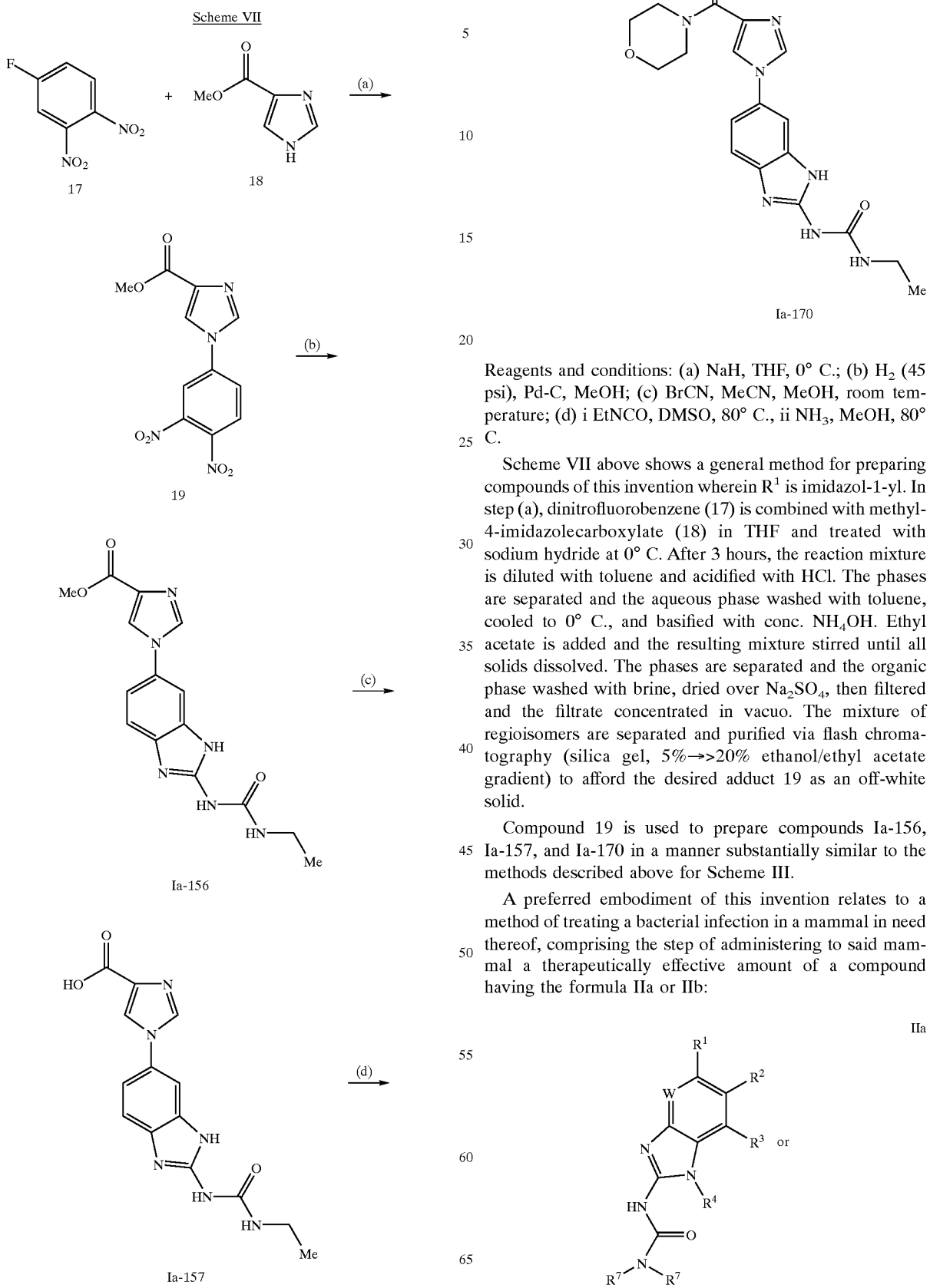

Reagents and conditions: (a) NaH, THF, 0° C.; (b) H$_2$ (45 psi), Pd-C, MeOH; (c) BrCN, MeCN, MeOH, room temperature; (d) i EtNCO, DMSO, 80° C., ii NH$_3$, MeOH, 80° C.

Scheme VII above shows a general method for preparing compounds of this invention wherein R$^1$ is imidazol-1-yl. In step (a), dinitrofluorobenzene (17) is combined with methyl-4-imidazolecarboxylate (18) in THF and treated with sodium hydride at 0° C. After 3 hours, the reaction mixture is diluted with toluene and acidified with HCl. The phases are separated and the aqueous phase washed with toluene, cooled to 0° C., and basified with conc. NH$_4$OH. Ethyl acetate is added and the resulting mixture stirred until all solids dissolved. The phases are separated and the organic phase washed with brine, dried over Na$_2$SO$_4$, then filtered and the filtrate concentrated in vacuo. The mixture of regioisomers are separated and purified via flash chromatography (silica gel, 5%→>20% ethanol/ethyl acetate gradient) to afford the desired adduct 19 as an off-white solid.

Compound 19 is used to prepare compounds Ia-156, Ia-157, and Ia-170 in a manner substantially similar to the methods described above for Scheme III.

A preferred embodiment of this invention relates to a method of treating a bacterial infection in a mammal in need thereof, comprising the step of administering to said mammal a therapeutically effective amount of a compound having the formula IIa or IIb:

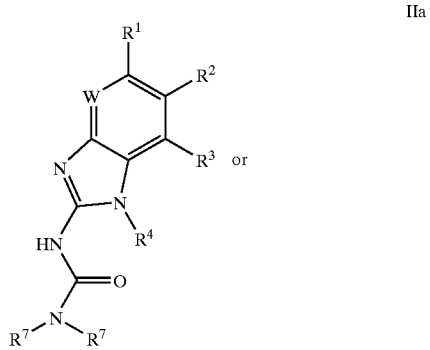

-continued

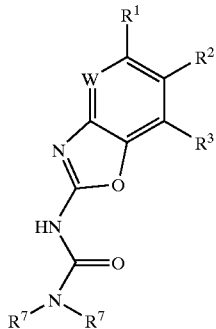

IIb or a pharmaceutically acceptable derivative or prodrug thereof, wherein:

W is nitrogen or $CR^a$;

$R^a$ is selected from hydrogen, halogen, —$CF_3$, $R^7$, —$OR^7$, or —$N(R^7)_2$;

$R^1$ is an aryl or heteroaryl ring, wherein said ring is optionally substituted by up to four $R^9$; wherein an $R^9$ substituent in the ortho-position of $R^1$ taken together with $R^2$ may form a fused, unsaturated or partially unsaturated, optionally substituted 5–8 membered ring having 0–2 ring heteroatoms selected from nitrogen, oxygen, or sulfur;

$R^2$ and $R^3$ are each independently selected from $R^6$, halogen, CN, $SR^6$, $OR^6$, $N(R^6)_2$, $NRCO_2R^6$, NRCON$(R^6)_2$, $CON(R^6)_2$ NRCOR$^6$, $NRN(R^6)_2$, $COR^6$, $CO_2R^6$, $COCOR^6$, $SO_2R^6$, $SO_2N(R^6)_2$ or $NRSO_2R^6$; or $R^2$ and $R^3$ are taken together to form a fused, unsaturated or partially unsaturated, optionally substituted 5–8 membered ring containing 0–2 ring heteroatoms selected from nitrogen, oxygen, or sulfur;

$R^4$ is selected from $R^6$, $CON(R^6)$, $COR^6$, $CO_2R^6$, $COCOR^6$, $SO_2R^6$, $SO_2N(R^6)_2$, or $(CH_2)_yR^2$;

y is 1–6;

Ar is a five membered heteroaryl, heterocyclyl, or carbocyclyl ring, wherein said ring is optionally substituted by up to three substituents selected from oxo, halogen, CN, $NO_2$, $R^8$, $OR^8$, $NHR^8$, $NHCOR^8$, $NHCONHR^8$, $COR^8$, $CONHR^8$, $SO_2R^8$, $NHSO_2NHR^8$ or $SO_2NHR^8$;

each $R^6$ is independently selected from $R^7$ or an optionally substituted group selected from alkoxy, hydroxyalkyl, heterocyclyl, heterocyclcylalkyl, aryl, aralkyl, aralkoxy, aryloxyalkyl, heteroaryl, heteroaralkyl, heteroaralkoxy, or heteroaryloxyalkyl;

each $R^7$ is independently selected from hydrogen or an optionally substituted aliphatic group having one to six carbons, or two $R^7$ on the same nitrogen taken together with the nitrogen optionally form a four to six member, saturated or unsaturated heterocyclic ring having one to three heteroatoms;

$R^8$ is a $C_1$–$C_4$ aliphatic group, wherein two $R^8$ on adjacent positions of Ar, or an aryl or heteroaryl ring, may be taken together with their intervening atoms to form a three to six membered fused ring;

each $R^9$ is independently selected from oxo, halogen, CN, $NO_2$, $T_n$(haloalkyl), $R^6$, $SR^6$, $OR^6$, $OR^8$, $N(R^6)_2$, CON$(R^6)_2$, $CON(R)COR^6$, $COR^6$, $CO_2R^6$, $CO_2N(R^6)_2$, $COCOR^6$, $SO_2R^6$, $SO_2N(R^6)_2$, $N(R)T_nCO_2R^6$, N(R) $T_nCON(R^6)_2$, $N(R)T_nN(R^6)_2$, $N(R)T_nNRCO_2R^6$, N(R) $T_nNRCON(R^6)_2$, $N(R)T_nCOR^6$, $N(R)T_nNRCOR^6$, $N(R)T_nSO_2N(R^6)_2$, $N(R)T_nSO_2R^6$, $T_nPO(OR^7)_2$, $T_nOPO(OR^7)_2$, $T_nSP(OR^7)_2$, $T_nPO(OR^7)_2$, or $T_nNPO(OR^7)_2$;

each Q is an independently selected $C_1$–$C_3$ branched or straight alkyl;

T is selected from —Q— or —$Q_m$—CH($Q_m$—$R^2$)—; and each m and n are independently selected from zero or one.

Another preferred embodiment of this invention relates to a method of treating a bacterial infection in a mammal in need thereof, comprising the step of administering to said mammal a therapeutically effective amount of a compound of formula IIIa or IIIb:

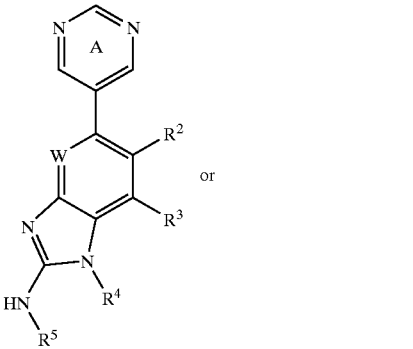

IIIa or

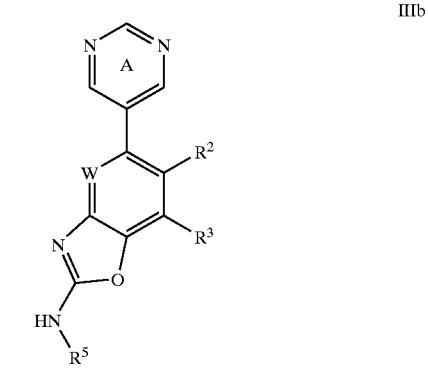

IIIb or a pharmaceutically acceptable derivative or prodrug thereof, wherein:

W is nitrogen or $CR^a$;

$R^a$ is selected from hydrogen, halogen, —$CF_3$, $R^7$, —$OR^7$, or —$N(R^7)_2$;

Ring A is optionally substituted with up to three $R^9$; wherein when an $R^9$ substituent is in the ortho-position of Ring A, said $R^9$ substituent may be taken together with $R^2$ to form an optionally substituted 5–7 membered ring containing 0–2 ring heteroatoms selected from nitrogen, oxygen, or sulfur;

$R^2$ and $R^3$ are each independently selected from $R^6$, halogen, CN, $SR^6$, $OR^6$, $N(R^6)_2$, $NRCO_2R^6$, NRCON $(R^6)_2$, $CON(R^6)_2$, $NRCOR^6$, $NRN(R^6)_2$, $COR^6$, $CO_2R^6$, $COCOR^6$, $SO_2R^6$, $SO_2N(R^6)_2$, or $NRSO_2R^6$; or $R^2$ and $R^3$ are taken together to form a fused, unsaturated or partially unsaturated, optionally substituted 5–8 membered ring containing 0–2 ring heteroatoms selected from nitrogen, oxygen, or sulfur;

$R^4$ is selected from $R^6$, $CON(R^6)$, $COR^6$, $CO_2R^6$, $COCOR^6$, $SO_2R^6$, $SO_2N(R^6)_2$, or $(CH_2)_yR^2$;

y is 1–6;

$R^5$ is selected from $R^7$, Ar, COAr, $CON(R^7)Ar$, $(CH_2)_yCO_2R$, $(CH_2)_yN(R^7)_2$, $C(=NR^{10})$—$N(R^7)_2$, C(=NR$^{10}$)—NRCOR, C(=S)—N(R$^7$)$_2$, CON(R$^7$)$_2$, COR, SO$_2$R, or SO$_2$N(R$^7$)$_2$;

Ar is a five membered heteroaryl, heterocyclyl, or carbocyclyl ring, wherein said ring is optionally substituted by up to three substituents selected from oxo, halogen, CN, NO$_2$, R$^8$, OR$^8$, NHR$^8$, NHCOR$^8$, NHCONHR$^8$, COR$^8$, CONHR$^8$, SO$_2$R$^8$, NHSO$_2$NHR$^8$ or SO$_2$NHR$^8$;

each R$^6$ is independently selected from R$^7$ or an optionally substituted group selected from alkoxy, hydroxyalkyl, heterocyclyl, heterocyclcylalkyl, aryl, aralkyl, aralkoxy, aryloxyalkyl, heteroaryl, heteroaralkyl, heteroaralkoxy, or heteroarayloxyalkyl;

each R$^7$ is independently selected from hydrogen or an optionally substituted aliphatic group having one to six carbons, or two R$^7$ on the same nitrogen taken together with the nitrogen optionally form a four to six member, saturated or unsaturated heterocyclic ring having one to three heteroatoms;

R$^8$ is a C$_1$–C$_4$ aliphatic group, wherein two R$^8$ on adjacent positions of Ar, or an aryl or heteroaryl ring, may be taken together with their intervening atoms to form a three to six membered fused ring;

each R$^9$ is independently selected from oxo, halogen, CN, NO$_2$, T$_n$(haloalkyl), R$^6$, SR$^6$, OR$^6$, OR$^8$, N(R$^6$)$_2$, CON(R$^6$)$_2$, CON(R)COR$^6$, COR$^6$, CO$_2$R$^6$, CO$_2$N(R$^6$)$_2$, COCOR$^6$, SO$_2$R$^6$, SO$_2$N(R$^6$)$_2$, N(R)T$_n$CO$_2$R$^6$, N(R)T$_n$CON(R$^6$)$_2$, N(R)T$_n$N(R$^6$)$_2$, N(R)T$_n$NRCO$_2$R$^6$, N(R)T$_n$NRCON(R$^6$)$_2$, N(R)T$_n$COR$^6$, N(R)T$_n$NRCOR$^6$, N(R)T$_n$SO$_2$N(R$^6$)$_2$, N(R)T$_n$SO$_2$R$^6$, T$_n$PO(OR$^7$)$_2$, T$_n$OPO(OR$^7$)$_2$, T$_n$SP(OR$^7$)$_2$, T$_n$PO(OR$^7$)$_2$, or T$_n$NPO(OR$^7$)$_2$;

each Q is an independently selected C$_1$–C$_3$ branched or straight alkyl;

T is selected from —Q— or —Q$_m$—CH(Q$_m$—R$^2$)—;

each m and n are independently selected from zero or one; and R$^{10}$ is selected from R$^7$ or Ar.

According to another embodiment, the invention provides a method of decreasing bacterial quantity in a biological sample. This method comprises the step of contacting said biological sample with a compound of formula I:

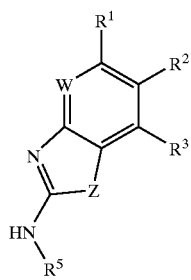

I or a pharmaceutically acceptable derivative or prodrug thereof, wherein:

Z is O or N—R$^4$;

W is nitrogen or CR$^a$;

R$^a$ is selected from hydrogen, halogen, —CF$_3$, R$^7$, —OR$^7$, or —N(R$^7$)$_2$;

R$^1$ is an aryl or heteroaryl ring, wherein said ring is optionally substituted by up to four R$^9$; wherein an R$^9$ substituent in the ortho-position of R$^1$ taken together with R$^2$ may form a fused, unsaturated or partially unsaturated, optionally substituted 5–8 membered ring having 0–2 ring heteroatoms selected from nitrogen, oxygen, or sulfur;

R$^2$ and R$^3$ are each independently selected from R$^6$, halogen, CN, SR$^6$, OR$^6$, N(R$^6$)$_2$, NRCO$_2$R$^6$, NRCON(R$^6$)$_2$, CON(R$^6$)$_2$, NRCOR$^6$, NRN(R$^6$)$_2$, COR$^6$, CO$_2$R$^6$, COCOR$^6$, SO$_2$R$^6$, SO$_2$N(R$^6$)$_2$, or NRSO$_2$R$^6$; or R$^2$ and R$^3$ are taken together to form a fused, unsaturated or partially unsaturated, optionally substituted 5–8 membered ring containing 0–2 ring heteroatoms selected from nitrogen, oxygen, or sulfur;

R$^4$ is selected from R$^6$, CON(R$^6$), COR$^6$, CO$_2$R$^6$, COCOR$^6$, SO$_2$R$^6$, SO$_2$N(R$^6$)$_2$, or (CH$_2$)$_y$R$^2$;

y is 1–6;

R$^5$ is selected from R$^7$, Ar, COAr, CON(R$^7$)Ar, (CH$_2$)$_y$CO$_2$R, (CH$_2$)$_y$N(R$^7$)$_2$, C(=NR$^{10}$)—N(R$^7$)$_2$, C(=NR$^{10}$)—NRCOR, C(=S)—N(R$^7$)$_2$, CON(R$^7$)$_2$, COR, SO$_2$R, or SO$_2$N(R$^7$)$_2$;

Ar is a five membered heteroaryl, heterocyclyl, or carbocyclyl ring, wherein said ring is optionally substituted by up to three substituents selected from oxo, halogen, CN, NO$_2$, R$^8$, OR$^8$, NHR$^8$, NHCOR$^8$, NHCONHR$^8$, COR$^8$, CONHR$^8$, SO$_2$R$^8$, NHSO$_2$NHR$^8$ or SO$_2$NHR$^8$;

each R$^6$ is independently selected from R$^7$ or an optionally substituted group selected from alkoxy, hydroxyalkyl, heterocyclyl, heterocyclcylalkyl, aryl, aralkyl, aralkoxy, aryloxyalkyl, heteroaryl, heteroaralkyl, heteroaralkoxy, or heteroarayloxyalkyl;

each R$^7$ is independently selected from hydrogen or an optionally substituted aliphatic group having one to six carbons, or two R$^7$ on the same nitrogen taken together with the nitrogen optionally form a four to six member, saturated or unsaturated heterocyclic ring having one to three heteroatoms;

R$^8$ is a C$_1$–C$_4$ aliphatic group, wherein two R$^8$ on adjacent positions of Ar, or an aryl or heteroaryl ring, may be taken together with their intervening atoms to form a three to six membered fused ring;

each R$^9$ is independently selected from oxo, halogen, CN, NO$_2$, T$_n$(haloalkyl), R$^6$, SR$^6$, OR$^6$, OR$^8$, N(R$^6$)$_2$, CON(R$^6$)$_2$, CON(R)COR$^6$, COR$^6$, CO$_2$R$^6$, CO$_2$N(R$^6$)$_2$, COCOR$^6$, SO$_2$R$^6$, SO$_2$N(R$^6$)$_2$, N(R)T$_n$CO$_2$R$^6$, N(R)T$_n$CON(R$^6$)$_2$, N(R)T$_n$N(R$^6$)$_2$, N(R)T$_n$NRCO$_2$R$^6$, N(R)T$_n$NRCON(R$^6$)$_2$, N(R)T$_n$COR$^6$, N(R)T$_n$NRCOR$^6$, N(R)T$_n$SO$_2$N(R$^6$)$_2$, N(R)T$_n$SO$_2$R$^6$, T$_n$PO(OR$^7$)$_2$, T$_n$OP(OR$^7$)$_2$, T$_n$SP(OR$^7$)$_2$, T$_n$PO(OR$^7$)$_2$, or T$_n$NPO(OR$^7$)$_2$;

each Q is an independently selected C$_1$–C$_3$ branched or straight alkyl;

T is selected from —Q— or —Q$_m$—CH(Q$_m$—R$^2$)—;

each m and n are independently selected from zero or one; and R$^{10}$ is selected from R$^7$ or Ar.

The term "biological sample", as used herein, includes cell cultures or extracts thereof; biopsied material obtained from a mammal or extracts thereof; and blood, saliva, urine, feces, semen, tears, or other body fluids or extracts thereof. The term "biological sample" also includes living organisms, in which case "contacting a compound of this invention with a biological sample" is synonymous with the term "administrating said compound (or composition comprising said compound) to a mammal."

A preferred embodiment comprises contacting said biological sample with a compound of formula Ia, Ib, IIa, IIb, IIIa, IIIb, or a compound listed in either of Tables 1 and 2.

Pharmaceutical compositions useful for such methods are described below.

The compounds of this invention are potent inhibitors of gyrase as determined by enzymatic assay. These compounds have also been shown to have antimicrobial activity in an antimicrobial susceptibility assay. The details of the conditions used for both the enzymatic and the antimicrobial susceptibility assays are set forth in the Examples below.

The gyrase inhibitors of this invention, or pharmaceutical salts thereof, may be formulated into pharmaceutical compositions for administration to animals or humans. These pharmaceutical compositions effective to treat or prevent a bacterial infection which comprise the gyrase inhibitor in an amount sufficient to measurably decrease bacterial quantity and a pharmaceutically acceptable carrier, are another embodiment of the present invention. The term "measurably decrease bacterial quantity", as used herein means a measurable change in the number of bacteria between a sample containing said inhibitor and a sample containing only bacteria.

Agents which increase the susceptibility of bacterial organisms to antibiotics are known. For example, U.S. Pat. No. 5,523,288, U.S. Pat. No. 5,783,561 and U.S. Pat. No. 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in *Microbiological Reviews* (1992) pp. 395–411, and the sensitization of gram-negative bacteria has been described by Tsubery, H., et al, in *J. Med. Chem.* (2000) pp. 3085–3092.

Another preferred embodiment of this invention relates to a method, as described above, of treating a bacterial infection in a mammal in need thereof, but further comprising the step of administering to said mammal an agent which increases the susceptibility of bacterial organisms to antibiotics.

According to another preferred embodiment, the invention provides a method, as described above, of decreasing bacterial quantity in a biological sample, but further comprising the step of contacting said biological sample with an agent which increases the susceptibility of bacterial organisms to antibiotics.

The pharmaceutical compositions and methods of this invention will be useful generally for controlling bacterial infections in vivo. Examples of bacterial organisms that may be controlled by the compositions and methods of this invention include, but are not limited to the following organisms: *Streptococcus pneumoniae, Streptococcus pyrogenes, Enterococcus fecalis, Enterococcus faecium, Klebsiella pneumoniae*, Enterobacter sps. Proteus sps. *Pseudomonas aeruginosa, E. coli, Serratia marcesens, Staphylococcus aureus*, Coag. Neg. Staph, *Haemophilus infuenzae, Bacillus anthracis, Mycoplasma pneumoniae*, and *Staphylococcus epidermitidis*. The compositions and methods will therefore be useful for controlling, treating or reducing the advancement, severity or effects of nosocomial or non-nosocomial infections. Examples of nosocomial uses include, but are not limited to, urinary tract infections, pneumonia, surgical wound infections, and bacteremia. Examples of non-nosocomial uses include but are not limited to urinary tract infections, pneumonia, prostatitis, skin and soft tissue infections, intra-abdominal infections, and therapy for febrile neutropenic patients.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\ alkyl)_4$ salts. This invention also envisions the quaternization of any basic nitrogen-containing groups of the compounds disclosed herein. Water or oil-soluble or dispersible products may be obtained by such quaternization.

Pharmaceutical compositions of this invention comprise a compound of formula I or a pharmaceutically acceptable salt thereof and a pharmaceutically acceptable carrier. Such compositions may optionally comprise an additional therapeutic agent. Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as α-tocopherol, polyethyleneglycol 1000 succinate, or other similar polymeric delivery matrices.

The term "pharmaceutically effective amount"refers to an amount effective in treating or ameliorating a bacterial infection in a patient. The term "prophylactically effective amount" refers to an amount effective in preventing or substantially lessening a bacterial infection in a patient.

Depending upon the particular condition, or disease state, to be treated or prevented, additional therapeutic agents, which are normally administered to treat or prevent that condition, may be administered together with the inhibitors of this invention. Such therapeutic agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The compounds of this invention may be employed in a conventional manner for controlling bacterial infections levels in vivo and for treating diseases or reducing the advancement or severity of effects which are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

The compounds of formula I may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula I and another therapeutic or prophylactic agent.

The additional therapeutic agents described above may be administered separately, as part of a multiple dosage regimen, from the inhibitor-containing composition. Alternatively, these agents may be part of a single dosage form, mixed together with the inhibitor in a single composition.

The pharmaceutical compositions of this invention may be administered orally, parenterally, by inhalation spray, topically, rectally, nasally, buccally, vaginally or via an implanted reservoir. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical, compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections caused by bacteria such as *Streptococcus pneumoniae, Streptococcus pyogenes, Enterococcus fecalis, Enterococcus faecium, Klebsiella pneumoniae*, Enterobacter sps. Proteus sps. *Pseudomonas aeruginosa, E. coli, Serratia marcesens, S. aureus*, and Coag. Neg. Staph.

Typically, the pharmaceutical compositions of this invention will be administered from about 1 to 5 times per day or alternatively, as a continuous infusion. Or, alternatively, the compositions of the present invention may be administered in a pulsatile formulaion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

According to another embodiment, the invention provides methods for treating or preventing a bacterial infection, or disease state, comprising the step of administering to a patient any compound, pharmaceutical composition, or combination described herein. The term "patient", as used herein, means an animal, preferably a mammal, and most preferably a human.

The compounds of this invention are also useful as commercial reagents which effectively bind to the gyrase B enzyme. As commercial reagents, the compounds of this invention, and their derivatives, may be used to block gyrase B activity in biochemical or cellular assays for bacterial gyrase B or its homologs or may be derivatized to bind to a stable resin as a tethered substrate for affinity chromatography applications. These and other uses which characterize commercial gyrase B inhibitors will be evident to those of ordinary skill in the art.

In order that this invention be more fully understood, the following examples are set forth. These examples are for the purpose of illustration only and are not to be construed as limiting the scope of the invention in any way.

EXAMPLES

Example 1

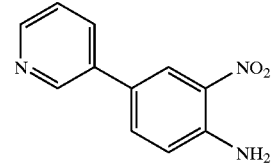

4-(Pyridin-3-yl)-2-nitroaniline (2): To a solution of 4-bromo-2-nitroaniline (217 mg, 1 mmol) in DMF (6 mL) was added 3-pyridine boronic acid (148 mg, 1.2 mmol), potassium phosphate (276 mg, 1.3 mmol), and dichloro-(diphenylphosphinoferrocene)palladium (75 mg, 0.1 mmol).

The resulting mixture was heated at 95° C. for 18 hours then cooled to room temperature and diluted with ethyl acetate (80 mL). The resulting solution was washed successively with saturated aqueous sodium bicarbonate, water, and brine, dried over magnesium sulfate then concentrated in vacuo. The concentrate was purified by chromatography [Silica Gel, ethyl acetate: hexanes (1:3)→(1:2)] to afford compound 2 (117 mg, 54%). $^{1}$H NMR (CDCl$_3$) δ 8.8 (d, 1H), 8.55 (m, 1H), 8.35 (d, 1H), 7.85 (dd, 1H), 7.65 (dd, 1H), 7.35 (m, 1H), 6.95 (d, 1H), 6.25 (br s, 2H).

Example 2

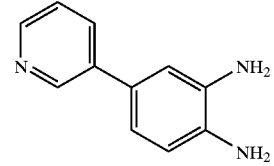

4-Pyridin-3-yl-benzene-1,2-diamine (3): To a solution of compound 2 (117 mg, 0.54 mmol) in ethyl acetate (13 mL) was added 10% palladium on carbon (51 mg). The resulting suspension was placed in a Parr hydrogenation apparatus under 40 psi hydrogen gas while shaking at ambient temperature for 2 hours. The catalyst was removed by filtration and the filtrate concentrated in vacuo to afford compound 2 (115 mg, quantitative yield). ¹H NMR (CDCl₃) δ 8.8 (m, 1H), 8.45 (m, 1H), 7.75 (m, 1H), 7.25 (m, 1H), 6.95 (m, 2H), 6.80 (m, 1H), 3.25 (br s, 4H).

Example 3

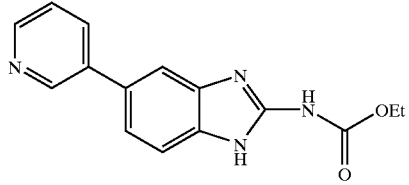

(5-Pyridin-3-yl-1H-benzoimidazol-2-yl)-carbamic acid ethyl ester (Ia-11): To a solution of 2-methyl-2-thiopseudourea (151 mg, 0.54 mmol) and ethylchloroformate (0.103 mL, 1.08 mmol) in water (2 mL) at 0° C. was added 25% aqueous sodium hydroxide in a dropwise fashion over 1 hour until the pH stabilized at 8. Enough acetic acid was then added to achieve pH 5 then sodium acetate trihydrate (74 mg, 0.54 mmol) and a solution of 2 (0.54 mmol) in ethanol (3 mL) were added. A catalytic amount of p-toluenesulfonic acid was added and the resulting mixture was heated at reflux for 1 hour. The reaction mixture was then cooled to ambient temperature and diluted with ethyl acetate (50 mL). The organic solution was washed with aqueous NaOH, water, and brine then dried over magnesium sulfate and concentrated in vacuo. The crude product was purified by preparative HPLC to afford compound Ia-11. ¹H NMR (CDCl₃) δ 9.1 (s, 1H), 8,75 (d, 1H), 8.5 (d, 1H), 7.9 (s, 1H), 7.8 (m, 1H), 7.65 (m, 2H), 4.3 (q, 2H), 1.3 (t, 3H). (M+1)₂₈₃.

Example 4

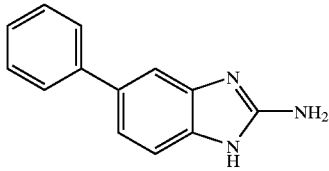

5-Phenyl-1H-benzoimidazol-2-ylamine (7): To a solution of biphenyl-3,4-diamine (0.99 mmol) in THF:MeOH:water (5 mL:10 mL:10 mL) was added cyanogen bromide (5M solution in acetonitrile, 1.06 mmol). The resulting mixture was stirred at room temperature overnight. The reaction was partitioned between EtOAc and aqueous sodium hydroxide and the aqueous layer re-extracted with EtOAc.

The combined EtOAc extracts were washed with water, brine, dried over MgSO₂, then concentrated in vacuo to afford 7 (147 mg, 71%) as an off-white solid.

Example 5

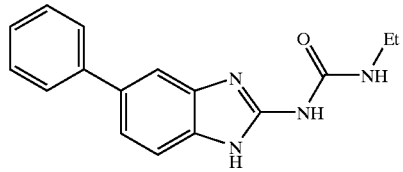

1-Ethyl-3-(5-phenyl-1H-benzoimidazol-2-yl)-urea (Ia-84): To a solution of 7 (40 mg, 0.19 mmol) in THF (1 mL) was added ethyl isocyanate (27 μL, 0.34 mmol) as a solution in THF (0.5 mL). The reaction was heated to reflux overnight then concentrated in vacuo. The crude product was purified by preparative HPLC to afford Ia-84.

Example 6

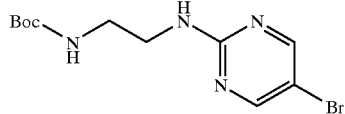

[2-(5-Bromo-pyrimidin-2-ylamino)-ethyl]-carbamic acid tert-butyl ester (10): A mixture of 5-bromo-2-chloropyrimidine (500 mg), N-Boc-ethylenediamine (496 mg), and triethylamine (1 mL) in ethanol (10 mL) was heated at 80° C. for 4 hours. The reaction was then concentrated in vacuo and the residue purified by preparative HPLC (hexanes:EtOAc; 60:40) to afford compound 10 (700 mg) as a white solid.

Example 7

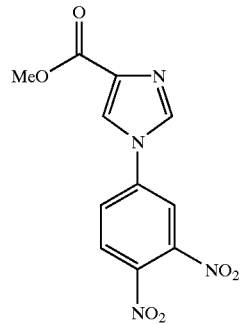

1-(3,4-Dinitro-phenyl)-1H-imidazole-4-carboxylic acid methyl ester (19): To a stirred, 0° C. solution of 1,2-dinitro-4-fluorobenzene (325 mg, 1.74 mmole) and methyl-4-imidazolecarboxylate (200 mg, 1.59 mmole) in THF (5 mL) was added NaH (70 mg, 1.74 mmole) in one portion. The resulting mixture was stirred at 0° C. for 3 hours, then diluted with toluene and acidified with 6N HCl. The phases were separated and the aqueous phase washed with toluene, cooled to 0° C., and basified with conc. NH₄OH. Ethyl acetate was added and the resulting mixture stirred until all solids dissolved. Phases separated, organic phase washed with brine, dried over Na₂SO₄, filtered, concentrated in vacuo. The mixture of regioisomers were separated and purified via flash chromatography (silica gel, 5%→>20% ethanol/ethyl acetate gradient) to fford the desired adduct 19 (225 mg, 48%) as an off-white solid. 1H NMR (500 MHz, dmso d6): 8.41 (1H, d); 8.13 (1H, d); 7.5 (1H, broad s); 7.28 (1H, s); 7.02 (1H, d); 3.80 (3H, s)

Example 8

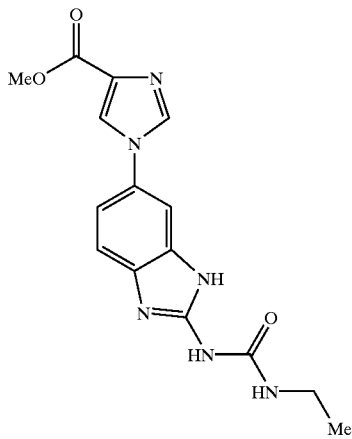

1-[2-(3-Ethyl-ureido)-3H-benzoimidazol-5-yl]-1H-imiazole-4-carboxylic acid methyl ester (Ia-156): A mixture of 19 (225 mg, 0.770 mmole) and 10% Pd-C. (catalytic amount) in MeOH (10 mL) was placed under 45 psi of $H_2$ (Parr Shaker) overnight. The mixture was filtered, concentrated in vacuo, re-diluted with MeCN and MeOH (5 mL/5 mL), and treated with cyanogen bromide (168 mg, 1.54 mmole) at room temperature. The resulting mixture was stirred for 4 hours (precipitate formed), then quenched by the addition of 7N $NH_3$-MeOH. The crude reaction was concentrated in vacuo and directly flash chromatographed (silica gel, 10%→>35% 7N NH3-MeOH/CH2Cl2 gradient) to give the pure aminobenzimidazole as a white solid.

The purified aminobenzimidazole was diluted in DMSO (1 mL), treated with excess ethyl-isocyanate (0.5 mL) and heated to 80° C. for 3 hours. The reaction was cooled to room temperature, excess ethyl isocyanate removed in vacuo, azeotroped with MeOH (thrice), diluted with MeOH (5 mL), treated with NH4OH (2 mL), and heated to 80° C. for 3 hours. The mixture was cooled to room temperature, concentrated in vacuo, diluted with 1/1 water/brine, and extracted twice with 4/1 ethyl acetate/ethanol. The combined organic extracts were dried over Na2SO4, filtered, concentrated in vacuo, and flash chromatographed (silica gel, 5%→>30% 2N $NH_3$-EtOH/$CH_2Cl_2$ gradient) to give the desired product Ia-156 contaminated with ethyl urea. The solid was triturated with water and filtered to give pure Ia-156 (115 mg, 41% over four steps) as a white solid. 1H NMR (500 MHz, dmso-d6): 11.81 (1H, br s); 9.94 (1H, br d); 8.32 (1H, br d); 8.26 (1H, br d); 7.58 (1H, br d); 7.48 (1H, m); 7.28 (1H, d); 7.12 (1H, br d); 3.78 (3H, s); 3.20 (2H, dq); 1.12 (3H, t).

Example 9

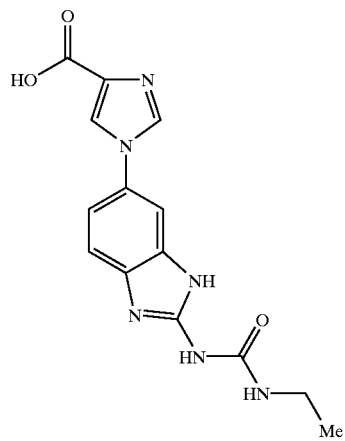

1-[2-(3-Ethyl-ureido)-3H-benzoimidazol-5-yl]-1H-imidazole-4-carboxylic acid 1-[2-(Ethyl-ureido)-3H-benzoimidazol-5-yl]-1H-imizaole-4-carboxylic acid (Ia-157): A solution of Ia-156 (95 mg, 0.289 mmole) in 6N HCl (2 mL) was refluxed for 6 hours. The solution was then cooled to room temperature, concentrated in vacuo, and azeotroped sequentially with MeOH (twice) and acetone (twice). The resulting solids were suspended in acetone, filtered, and washed with acetone followed by hexanes to give Ia-157 (115 mg, 100%) as a white solid. 1H NMR (500 MHz, dmso-d6): 8.77 (1H, m); 8.52 (1H, m); 7.79 (1H, s); 7.72 (1H, m); 7.65 (2H, m); 5.6–4.0 (2H, br s); 3.20 (2H, dt); 1.11 (3H, t).

Example 10

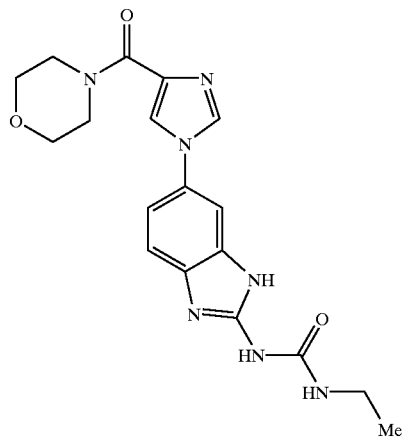

A solution of Ia-157 (20 mg, 0.051 mmole) and morpholine (0.050 mL, excess) in DMF (1 mL) was treated with PyBrop (20 mg, excess) at room temperature. The resulting mixture was stirred overnight, then diluted with 4:1 ethyl acetate:ethanol, washed with 1:1 brine:water (five times), dried over Na2SO4, filtered, and flash chromatographed (silica gel, 5%→>20% 2N $NH_3$-EtOH/$CH_2Cl_2$ gradient) to give Ia-170 (13 mg, 72%) as a white solid. LRMS: 384.5 (M+H)

Example 11

We have prepared other compounds of formula I by methods substantially similar to those described in the above Examples 1–6 and those illustrated in Schemes I–VI. The characterization data for these compounds is summarized in Table 3 below and includes mass spectral (as M+1) and $^1$H NMR data.

$^1$H NMR data is summarized in Table 3 below wherein "Y" designates $^1$H NMR data is available and was found to be consistant with structure. Compound numbers correspond to the compound numbers listed in Table 1.

TABLE 3

Characterization Data for Selected Compounds

| No.Ia- | M + 1 | $^1$H NMR |
|---|---|---|
| 1 | 282 | Y |
| 2 | 288 | Y |
| 3 | 283 | Y |
| 4 | 283 | Y |
| 6 | 210 | Y |
| 7 | 268 | Y |
| 8 | 292 | — |
| 9 | 350 | Y |
| 10 | 296 | Y |
| 11 | 283 | Y |
| 12 | 325 | Y |
| 13 | 324 | Y |
| 14 | 336 | Y |
| 15 | 326 | Y |
| 16 | 344 | Y |
| 17 | 361 | Y |
| 18 | 313 | Y |
| 19 | 360 | Y |
| 20 | 399 | Y |
| 21 | 284 | Y |
| 22 | 314 | Y |
| 23 | 312 | Y |
| 24 | 326 | Y |
| 26 | 342 | Y |
| 33 | 249 | Y |
| 34 | 298 | Y |
| 35 | 356 | Y |
| 36 | 283 | Y |
| 37 | 428 | Y |
| 38 | 294 | Y |
| 39 | 272 | Y |
| 40 | 498 | Y |
| 41 | 452 | Y |
| 42 | 312 | Y |
| 43 | 295.1 | Y |
| 44 | 338 | — |
| 45 | 386 | Y |
| 46 | 320 | Y |
| 47 | 382 | — |
| 48 | 389 | — |
| 49 | 418 | — |
| 50 | 311 | Y |
| 51 | 299 | Y |
| 52 | 343 | Y |
| 53 | 368 | Y |
| 54 | 298 | Y |
| 55 | 395 | Y |
| 56 | 406 | — |
| 57 | 366 | Y |
| 58 | 296 | Y |
| 59 | 354 | Y |
| 60 | 326 | Y |
| 61 | 440 | Y |
| 62 | 300 | Y |
| 63 | 403 | — |
| 64 | 381 | — |
| 65 | 352 | — |
| 66 | 326 | — |
| 67 | 409 | Y |
| 69 | 468 | Y |
| 70 | 368 | Y |
| 71 | 299 | Y |
| 72 | 299 | Y |
| 73 | 267 | — |
| 74 | 253 | — |
| 75 | 297 | — |
| 76 | 413 | Y |
| 77 | 371 | — |
| 78 | 282 | Y |
| 79 | 296 | Y |
| 80 | 357 | Y |
| 81 | 340 | Y |
| 82 | 280 | Y |
| 84 | 281 | Y |
| 85 | 321 | — |
| 86 | 442 | Y |
| 87 | 370 | Y |
| 88 | 342 | — |
| 89 | 359 | Y |
| 90 | 298 | Y |
| 91 | 446 | Y |
| 92 | 329 | — |
| 93 | 499 | Y |
| 94 | 387 | Y |
| 97 | 294 | Y |
| 98 | 389 | — |
| 100 | 370 | — |
| 101 | 280 | — |
| 102 | 370 | — |
| 103 | 312 | Y |
| 106 | 409 | — |
| 108 | 300 | Y |
| 109 | 394 | — |
| 110 | 467 | Y |
| 111 | 367 | Y |
| 112 | 343 | Y |
| 113 | 409 | — |
| 115 | 298 | Y |
| 116 | 343 | — |
| 117 | 369 | — |
| 116 | 282 | Y |
| 119 | 296 | Y |
| 120 | 296 | Y |
| 121 | 322 | Y |
| 122 | 340 | Y |
| 124 | 445 | — |
| 125 | 382 | — |
| 126 | 328 | Y |
| 127 | 394 | — |
| 128 | 432 | — |
| 129 | 368 | — |
| 130 | 396 | Y |
| 131 | 316 | Y |
| 132 | 312 | Y |
| 133 | 296 | Y |
| 134 | 316 | Y |
| 135 | 410 | Y |
| 136 | 300 | Y |
| 137 | 310 | Y |
| 138 | 388 | — |
| 139 | 352 | Y |
| 140 | 401 | Y |
| 141 | 384 | Y |
| 142 | 310 | Y |
| 143 | 511 | Y |
| 144 | 311 | Y |
| 145 | 353 | — |
| 146 | 400 | Y |
| 147 | 326 | Y |
| 148 | 411 | Y |
| 149 | 370 | Y |
| 150 | — | — |
| 151 | — | — |
| 152 | 317 | Y |
| 153 | 362 | Y |
| 154 | 389 | Y |
| 155 | 299 | — |
| 156 | — | — |
| 157 | — | — |

TABLE 3-continued

Characterization Data for Selected Compounds

| No.Ia- | M + 1 | $^1$H NMR |
|---|---|---|
| 158 | — | — |
| 159 | 328 | — |
| 160 | — | — |
| 161 | — | — |
| 162 | — | — |
| 163 | 326 | Y |
| 164 | 367 | Y |
| 165 | 297 | Y |
| 166 | 367 | Y |
| 167 | 350 | — |
| 168 | 298 | Y |
| 169 | — | Y |
| 170 | — | — |
| 171 | — | — |
| 172 | — | — |
| 173 | — | — |
| 174 | — | — |
| 175 | 365 | Y |
| 176 | — | Y |
| 177 | — | — |
| 178 | — | Y |
| 179 | 367 | Y |
| 180 | — | Y |
| 181 | 315 | Y |
| 182 | 366 | Y |
| 183 | 330 | Y |
| 184 | — | — |
| 185 | — | — |
| 186 | — | — |
| 187 | — | — |
| 188 | — | — |

Example 12

Gyrase ATPase Assay

The ATP hydrolysis activity of DNA gyrase was measure by coupling the production of ADP through pyruvate kinase/lactate dehydrogenase to the oxidation of NADH. This method has been described previously (Tamura and Gellert, 1990, *J. Biol. Chem.*, 265, 21342).

ATPase assays are carried out at 30° C. in buffered solutions containing 100 mM TRIS pH 7.6, 1.5 mM MgCl$_2$, 50 mM KCl. The coupling system contains (final concentrations) 2.5 mM phosphoenol pyruvate, 200 μM nicotinamide adenine dinucleotide (NADH), 1 mM DTT, 30 ug pyruvate kinase, and 10 ug/ml lactate dehydrogenase. 40 nanomolar enzyme (374 kDa Gyr A2B2 subunit from *Staphylococcus aureus*) and a DMSO solution of the inhibitor to a final concentration of 4% are added and the reaction mixture is allowed to incubate for 10 minutes at 30° C. The reaction is then started by the addition of ATP to a final concentration of 0.9 mM and the rate of NADH disappearance at 340 nanometers is measured over the course of 10 minutes. The percent inhibition values are determined from rate versus concentration profiles and are reported as the average of duplicate values.

Table 4 shows the results of the percent inhibition activity of selected compounds of this invention in the Gyrase inhibition assay at 10 μM concentration. The compound numbers correspond to the compound numbers in Table 1. Compounds having an activity designated as "A" provided a percent inhibition value below 50 percent; compounds having an activity designated as "B" provided a percent inhibition value between 50 and 75 percent; and compounds having an activity designated as "C" provided a percent inhibition value greater than 75 percent.

TABLE 4

Gyrase Inhibitory Activity of Selected Compounds

| No. Ia- | Activity |
|---|---|
| 1 | B |
| 2 | B |
| 3 | B |
| 4 | C |
| 6 | A |
| 7 | A |
| 8 | A |
| 9 | A |
| 10 | A |
| 11 | C |
| 12 | B |
| 13 | A |
| 14 | B |
| 15 | B |
| 16 | C |
| 17 | C |
| 18 | C |
| 19 | C |
| 20 | A |
| 21 | C |
| 22 | C |
| 23 | C |
| 24 | C |
| 26 | B |
| 33 | A |
| 34 | C |
| 35 | C |
| 36 | A |
| 37 | C |
| 38 | B |
| 39 | C |
| 40 | C |
| 41 | A |
| 42 | C |
| 43 | C |
| 44 | C |
| 45 | C |
| 46 | A |
| 47 | C |
| 48 | C |
| 49 | C |
| 50 | B |
| 52 | C |
| 53 | C |
| 54 | C |
| 55 | C |
| 56 | C |
| 57 | C |
| 58 | C |
| 59 | C |
| 60 | C |
| 61 | C |
| 62 | C |
| 63 | C |
| 64 | C |
| 65 | C |
| 66 | C |
| 67 | C |
| 69 | B |
| 70 | C |
| 71 | A |
| 72 | C |
| 73 | A |
| 74 | A |
| 75 | A |
| 76 | C |
| 77 | C |
| 78 | A |
| 79 | A |
| 80 | C |
| 81 | B |
| 82 | A |
| 84 | C |
| 85 | A |
| 86 | C |

TABLE 4-continued

Gyrase Inhibitory Activity of Selected Compounds

| No. Ia- | Activity |
| --- | --- |
| 87 | C |
| 88 | C |
| 89 | C |
| 90 | C |
| 91 | A |
| 92 | C |
| 93 | C |
| 94 | C |
| 97 | A |
| 98 | C |
| 100 | C |
| 101 | A |
| 102 | C |
| 103 | C |
| 106 | C |
| 108 | C |
| 109 | C |
| 110 | C |
| 111 | C |
| 112 | C |
| 113 | C |
| 115 | A |
| 116 | B |
| 117 | A |
| 118 | C |
| 119 | C |
| 120 | B |
| 121 | A |
| 122 | C |
| 124 | B |
| 125 | C |
| 126 | C |
| 127 | C |
| 128 | C |
| 129 | C |
| 130 | C |
| 131 | C |
| 132 | C |
| 133 | C |
| 134 | C |
| 135 | C |
| 136 | C |
| 137 | C |
| 138 | C |
| 139 | C |
| 140 | C |
| 141 | C |
| 142 | C |
| 143 | C |
| 144 | C |
| 145 | C |
| 146 | C |
| 147 | B |
| 148 | C |
| 149 | C |
| 150 | B |
| 151 | C |
| 152 | C |
| 153 | B |
| 154 | C |
| 155 | A |
| 156 | C |
| 157 | C |
| 158 | C |
| 159 | A |
| 160 | C |
| 161 | A |
| 162 | C |
| 163 | C |
| 164 | C |
| 165 | C |
| 166 | C |
| 167 | C |
| 168 | C |
| 169 | C |
| 170 | C |
| 171 | C |
| 172 | C |
| 173 | C |
| 174 | C |
| 175 | C |
| 176 | A |
| 177 | C |
| 178 | C |
| 179 | C |
| 180 | C |
| 181 | B |
| 182 | C |
| 183 | B |
| 184 | B |
| 185 | C |
| 186 | C |
| 187 | C |
| 188 | C |
| — | — |

Example 13

Susceptibility Testing in Liquid Media

Compounds of this invention were also tested for antimicrobial activity by susceptibility testing in liquid media. Such assays were performed within the guidelines of the latest NCCLS document governing such practices: "M7-A5 Methods for dilution Antimicrobial Susceptibility Tests for Bacteria that Grow Aerobically; Approved Standard—Fifth Edition (2000)". Other publications such as "Antibiotics in Laboratory Medicine" (Edited by V. Lorian, Publishers Williams and Wilkins, 1996) provide essential practical techniques in laboratory antibiotic testing. Essentially, several discrete bacterial colonies (3 to 7) from a freshly streaked plate were transferred to an appropriate rich broth medium such as MHB, supplemented where appropriate for the more fastidious organisms. This was grown overnight to high density followed by a 1 or 2-thousand-fold dilution to give an inoculation density of between $5 \times 10^5$ and $5 \times 10^6$ CFU per mL. Alternatively, the freshly picked colonies can be incubated at 37° C. for about 4 to 8 hrs until the culture equals or exceeds a turbidity of a 0.5 McFarland standard (approximately $1.5 \times 10^8$ cells per mL) and diluted to give the same CFU per mL as above. In a more convenient method, the inoculum was prepared using a commercially available mechanical device (the BBL PROMPT System) that involves touching five colonies directly with a wand, containing crosshatch grooves at its bottom, followed by suspension of the bacteria in an appropriate volume of saline. Dilution to the appropriate inoculum cell density was made from this cell suspension. The broth used for testing consists of MHB supplemented with 50 mg per L of $Ca^{2+}$ and 25 mg per L of $Mg^{2+}$. Standard dilution panels of control antibiotics were made and stored as in the NCCLS standard M7-A5, the dilution range typically being in the 128 µg per mL to 0.015 µg per mL (by 2-fold serial dilution). The test compounds were dissolved and diluted fresh for experimentation on the same day; the same or similar ranges of concentration as above being used. The test compounds and controls were dispensed into a multiwell plate and test bacteria added such that the final inoculation was approximately $5 \times 10^4$ CFU per well and the final volume was 100 µL. The plates were incubated at 35° C. overnight (16 to 20 hr) and checked by eye for turbidity or quantitated with a multiwell plate reader.

The endpoint minimal inhibitory concentration (MIC) is the lowest concentration of drug at which the microorganism tested does not grow. Such determinations were also compared to the appropriate tables contained in the above two publications to ensure that the range of antibacterial activity is within the acceptable range for this standardized assay.

Table 5 shows the results of the MIC assay for selected compounds of this invention. The compound numbers correspond to the compound numbers in Table 1. Compounds having an activity level designated as "A" provided an MIC of less than 10 μg/mL; compounds having an activity level designated as "B" provided an MIC of between 10 and 40 μg/mL; compounds having an activity level designated as "C" provided an MIC of greater than 40 μg/mL.

TABLE 5

MIC Values of Selected Compounds

| No. Ia- | Activity |
|---|---|
| 42 | B |
| 58 | A |
| 90 | A |
| 92 | A |
| 98 | B |
| 112 | A |
| 116 | C |
| 117 | C |
| 118 | A |
| 119 | C |
| 120 | C |
| 121 | C |
| 122 | C |
| 133 | A |
| 137 | C |
| 138 | C |
| 139 | C |
| 140 | A |
| 141 | A |
| 142 | A |
| 144 | B |
| 145 | B |
| 146 | A |
| 147 | C |
| 148 | B |
| 149 | C |
| 150 | C |
| 151 | C |
| 152 | B |
| 153 | C |
| 154 | C |
| 156 | B |
| 157 | C |
| 158 | C |
| 159 | C |
| 160 | C |
| 161 | C |
| 162 | C |
| 163 | A |
| 164 | C |
| 165 | B |
| 166 | C |
| 167 | C |
| 168 | A |
| 169 | B |
| 170 | C |
| 171 | B |
| 173 | B |
| 174 | C |
| 175 | C |
| 177 | C |
| 178 | A |
| 179 | C |
| 180 | B |
| 181 | C |
| 182 | C |
| 183 | C |

TABLE 5-continued

MIC Values of Selected Compounds

| No. Ia- | Activity |
|---|---|
| 184 | C |
| 185 | C |
| 186 | A |
| 187 | B |
| 188 | A |
| 196 | B |
| 197 | B |
| 198 | B |
| — | — |

While we have described a number of embodiments of this invention, it is apparent that our basic constructions may be altered to provide other embodiments which utilize the products and processes of this invention.

We claim:

1. A compound of formula IIa or IIb:

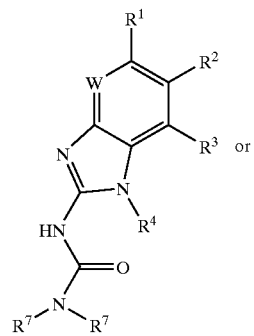

IIa

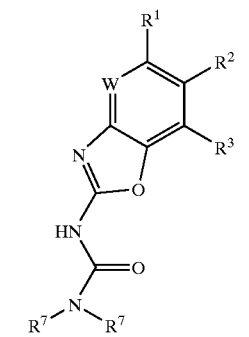

IIb or a pharmaceutically acceptable salt thereof, wherein:

W is nitrogen or $CR^a$;

$R^a$ is selected from hydrogen, halogen, —$CF_3$, $R^7$, —$OR^7$, or —$N(R^7)_2$;

$R^1$ is an aryl or heteroaryl ring, wherein said ring is optionally substituted by up to four $R^9$; wherein an $R^9$ substituent in the ortho-position of $R^1$ taken together with $R^2$ may form a fused, unsaturated or partially unsaturated, optionally substituted 5–8 membered ring having 0–2 ring heteroatoms selected from nitrogen, oxygen, or sulfur;

$R^2$ and $R^3$ are each independently selected from $R^6$, halogen, CN, $SR^6$, $OR^6$, $N(R^6)_2$, $NRCO_2R^6$, $NRCON(R^6)_2$, $CON(R^6)_2$, $NRCOR^6$, $NRN(R^6)_2$, $COR^6$, $CO_2R^6$, $COCOR^6$, $SO_2R^6$, $SO_2N(R^6)_2$, or $NRSO_2R^6$; or $R^2$ and $R^3$ are taken together to form a fused, unsaturated or partially unsaturated, optionally substituted 5–8 membered ring containing 0–2 ring heteroatoms selected from nitrogen, oxygen, or sulfur;

$R^4$ is selected from $R^6$, $CON(R^6)$, $COR^6$, $CO_2R^6$, $COCOR^6$, $SO_2R^6$, $SO_2N(R^6)_2$, or $(CH_2)_yR^2$;

y is 1–6;

Ar is a five membered heteroaryl, heterocyclyl, or carbocyclyl ring, wherein said ring is optionally substituted by up to three substituents selected from oxo, halogen, CN, $NO_2$, $R^8$, $OR^8$, $NHR^8$, $NHCOR^8$, $NHCONHR^8$, $COR^8$, $CONHR^8$, $SO_2R^8$, $NHSO_2NHR^8$ or $SO_2NHR^8$;

each $R^6$ is independently selected from $R^7$ or an optionally substituted group selected from alkoxy, hydroxyalkyl, heterocyclyl, heterocyclcylalkyl, aryl, aralkyl, aralkoxy, aryloxyalkyl, heteroaryl, heteroaralkyl, heteroaralkoxy, or heteroarayloxyalkyl;

each $R^7$ is independently selected from hydrogen or an optionally substituted aliphatic group having one to six carbons, or two $R^7$ on the same nitrogen taken together with the nitrogen optionally form a four to six member, saturated or unsaturated heterocyclic ring having one to three heteroatoms;

$R^8$ is a $C_1$–$C_4$ aliphatic group, wherein two $R^8$ on adjacent positions of Ar, or an aryl or heteroaryl ring, may be taken together with their intervening atoms to form a three to six membered fused ring;

each $R^9$ is independently selected from oxo, halogen, CN, $NO_2$, $T_n$(haloalkyl), $R^6$, $SR^6$, $OR^6$, $OR^8$, $N(R^6)_2$, $CON(R^6)_2$, $CON(R)COR^6$, $COR^6$, $CO_2R^6$, $CO_2N(R^6)_2$, $COCOR^6$, $SO_2R^6$, $SO_2N(R^6)_2$, $N(R)T_nCO_2R^6$, $N(R)T_nCON(R^6)_2$, $N(R)T_nN(R^6)_2$, $N(R)T_nNRCO_2R^6$, $N(R)T_nNRCON(R^6)_2$, $N(R)T_nCOR^6$, $N(R)T_NRCOR^6$, $N(R)T_nSO_2N(R^6)_2$, $N(R)T_nSO_2R^6$, $T_nPO(OR^7)_2$, $T_nOPO(OR^7)_2$, $T_nSP(OR^7)_2$, $T_nPO(OR^7)_2$, or $T_nNPO(OR^7)_2$;

each Q is an independently selected $C_1$–$C_3$ branched or straight alkyl;

T is selected from —Q— or —$Q_m$—$CH(Q_m$—$R^2)$—; and each m and n are independently selected from zero or one.

2. The compound according to claim 1, wherein said compound has one or more features selected from the group consisting of:

(a) $R^1$ is an optionally substituted aryl or heteroaryl ring;

(b) $R^2$ and $R^3$ are each independently selected from halogen, CN, $CO_2R^6$, $OR^6$, or $R^6$; and (c) $R^9$ is halogen, CN, oxo, $R^6$, $SR^6$, $OR^6$, $N(R^6)_2$, $CON(R^6)_2$, $CO_2R^6$, $CON(R)COR^6$, $N(R)T_nCO_2R^6$, $N(R)T_nNRCO_2R^6$, $N(R)T_nN(R^6)_2$, $NO_2$, $T_n$(haloalkyl), $CO_2N(R^6)_2$, $COR^6$, $SO_2R^6$, or $SO_2N(R^6)_2$.

3. The compound according to claim 2, wherein:

(a) $R^1$ is an optionally substituted aryl or heteroaryl ring;

(b) $R^2$ and $R^3$ are each independently selected from halogen, CN, $CO_2R^6$, $OR^6$, or $R^6$; and (c) $R^9$ is halogen, CN, oxo, $R^6$, $SR^6$, $OR^6$, $N(R^6)_2$, $CON(R^6)_2$, $CO_2R^6$, $CON(R)COR^6$, $N(R)T_nCO_2R^6$, $N(R)T_nNRCO_2R^6$, $N(R)T_nN(R^6)_2$, $NO_2$, $T_n$(haloalkyl), $CO_2N(R^6)_2$, $COR^6$, $SO_2R^6$, or $SO_2N(R^6)_2$.

4. The compound according to claim 2, wherein said compound has one or more features selected from the group consisting of:

(a) $R^1$ is an optionally substituted ring selected from phenyl, 2-pyridyl, 3-pyridyl, 4-pyridyl, thienyl, pyrimidyl, imidazol-1-yl, imidazol-2-yl, pyrazol-1-yl, amino-pyrimidinyl, quinolinyl, aminobenzimidazole, or indolyl;

(b) $R^2$ is hydrogen, alkoxy, aminoalkyl, or halogen;

(c) $R^3$ is hydrogen, alkoxy, aralkoxy, or halogen;

(d) $R^4$ is hydrogen or $(CH_2)_yR^2$; and (e) $R^9$ is halogen, CN, oxo, $R^6$, $SR^6$, $OR^6$, $N(R^6)_2$, $CON(R^6)_2$, $CO_2R^6$, $CON(R)COR^6$, or $N(R)T_nCO_2R^6$.

5. The compound according to claim 4, wherein:

(a) $R^1$ is an optionally substituted ring selected from phenyl, 2-pyridyl, 3-pyridyl, 4-pyridyl, thienyl, pyrimidyl, imidazol-1-yl, imidazol-2-yl, pyrazol-1-yl, amino-pyrimidinyl, quinolinyl, aminobenzimidazole, or indolyl;

(b) $R^2$ is hydrogen, alkoxy, aminoalkyl, or halogen;

(c) $R^3$ is hydrogen, alkoxy, aralkoxy, or halogen;

(d) $R^4$ is hydrogen or $(CH_2)_yR^2$; and (e) $R^9$ is halogen, CN, oxo, $R^6$, $SR^6$, $OR^6$, $N(R^6)_2$, $CON(R^6)_2$, $CO_2R^6$, $CON(R)COR^6$, or $N(R)T_nCO_2R^6$.

6. A compound of formula IIIa or IIIb:

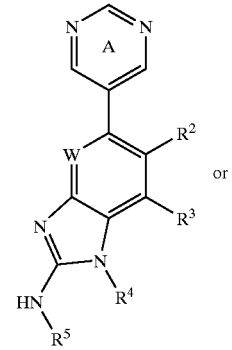

IIIa

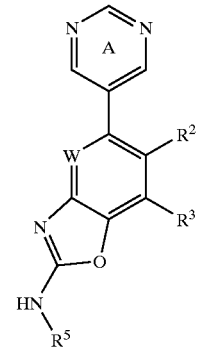

IIIb or a pharmaceutically acceptable salt thereof, wherein:

W is nitrogen or $CR^a$;

$R^a$ is selected from hydrogen, halogen, —$CF_3$, $R^7$, —$OR^7$, or —$N(R^7)_2$;

Ring A is optionally substituted with up to three $R^9$; wherein when an $R^9$ substituent is in the ortho-position of Ring A, said $R^9$ substituent may be taken together with $R^2$ to form an optionally substituted 5–7 membered ring containing 0–2 ring heteroatoms selected from nitrogen, oxygen, or sulfur;

$R^2$ and $R^3$ are each independently selected from $R^6$, halogen, CN, $SR^6$, $OR^6$, $N(R^6)_2$, $NRCO_2R^6$, $NRCON(R^6)_2$, $CON(R^6)_2$, $NRCOR^6$, $NRN(R^6)_2$, $COR^6$, $CO_2R^6$, $SO_2R^6$, $SO_2N(R^6)_2$, or $NRSO_2R^6$; or $R^2$ and $R^3$ are taken together to form a fused, unsaturated or partially unsaturated, optionally substituted 5–8 membered ring containing 0–2 ring heteroatoms selected from nitrogen, oxygen, or sulfur;

R$^4$ is selected from R$^6$, CON(R$^6$), COR$^6$, CO$_2$R$^6$, COCOR$^6$, SO$_2$R$^6$, SO$_2$N(R$^6$)$_2$, or(CH$_2$)$_y$R$^2$;

y is 1–6;

R$^5$ is selected from R$^7$, Ar, COAr, CON(R$^7$)Ar, (CH$_2$)$_y$CO$_2$R, (CH$_2$)$_y$N(R$^7$)$_2$, C(=NR$^{10}$)—N(R$^7$)$_2$, C(=NR$^{10}$)—NRCOR, C(=S)—N(R$^7$)$_2$, CON(R$^7$)$_2$, COR, SO$_2$R, or SO$_2$N(R$^7$)$_2$;

Ar is a five membered heteroaryl, heterocyclyl, or carbocyclyl ring, wherein said ring is optionally substituted by up to three substituents selected from oxo, halogen, CN, NO$_2$, R$^8$, OR$^8$, NHR$^8$, NHCOR$^8$, NHCONHR$^8$, COR$^8$, CONHR$^8$, SO$_2$R$^8$, NHSO$_2$NHR$^8$ or SO$_2$NHR$^8$;

each R$^6$ is independently selected from R$^7$ or an optionally substituted group selected from alkoxy, hydroxyalkyl, heterocyclyl, heterocyclcylalkyl, aryl, aralkyl, aralkoxy, aryloxyalkyl, heteroaryl, heteroaralkyl, heteroaralkoxy, or heteroarayloxyalkyl;

each R$^7$ is independently selected from hydrogen or an optionally substituted aliphatic group having one to six carbons, or two R$^7$ on the same nitrogen taken together with the nitrogen optionally form a four to six member, saturated or unsaturated heterocyclic ring having one to three heteroatoms;

R$^8$ is a C$_1$–C$_4$ aliphatic group, wherein two R$^8$ on adjacent positions of Ar, or an aryl or heteroaryl ring, may be taken together with their intervening atoms to form a three to six membered fused ring;

each R$^9$ is independently selected from oxo, halogen, CN, NO$_2$, T$_n$(haloalkyl), R$^6$, SR$^6$, OR$^6$, OR$^8$, N(R$^6$)$_2$, CON(R$^6$)$_2$, CON(R)COR$^6$, COR$^6$, CO$_2$R$^6$, CO$_2$N(R$^6$)$_2$, COCOR$^6$, SO$_2$R$^6$, SO$_2$N(R$^6$)$_2$, N(R)T$_n$CO$_2$R$^6$, N(R)T$_n$CON(R$^6$)$_2$, N(R)T$_n$N(R$^6$)$_2$, N(R)T$_n$NRCO$_2$R$^6$, N(R)T$_n$NRCON(R$^6$)$_2$, N(R)T$_n$COR$^6$, N(R)T$_n$NRCOR$^6$, N(R)T$_n$SO$_2$N(R$^6$)$_2$, N(R)T$_n$SO$_2$R$^6$, T$_n$PO(OR$^7$)$_2$, T$_n$OPO(OR$^7$)$_2$, T$_{nSP(OR}$$^7$)$_2$, T$_n$PO(OR$^7$)$_2$, or T$_n$NPO(OR$^7$)$_2$;

each Q is an independently selected C$_1$–C$_3$ branched or straight alkyl;

T is selected from —Q— or —Q$_m$—CH(Q$_m$—R$^2$)—;

each m and n are independently selected from zero or one; and R$^{10}$ is selected from R$^7$ or Ar.

7. The compound according to claim 6, wherein said compound has one or more features selected from the group consisting of:

(a) R$^2$ and R$^3$ are each independently selected from halogen, CN, CO$_2$R$^6$, OR$^6$, or R$^6$;

(b) R$^5$ is CO$_2$R, COAr, COR, CON(R$^7$)$_2$, Ar, (CH$_2$)$_y$CO$_2$R, or (CH$_2$)$_y$N(R$^7$)$_2$; and (c) R$^9$ is halogen, CN, oxo, R$^6$, SR$^6$, OR$^6$, N(R$^6$)$_2$, CON(R$^6$)$_2$, CO$_2$R$^6$, CON(R)COR$^6$, N(R)T$_n$CO$_2$R$^6$, N(R)T$_n$NRCO$_2$R$^6$, N(R)T$_n$N(R$^6$)$_2$, NO$_2$, T$_n$(haloalkyl), CO$_2$N(R$^6$)$_2$, COR$^6$, SO$_2$R$^6$, or SO$_2$N(R$^6$)$_2$.

8. The compound according to claim 7, wherein:

(a) R$^2$ and R$^3$ are each independently selected from halogen, CN, CO$_2$R$^6$, OR$^6$, or R$^6$;

(b) R$^5$ is CO$_2$R, COAr, COR, CON(R$^7$)$_2$, Ar, (CH$_2$)$_{CO2}$R, or (CH$_2$)$_y$N(R$^7$)$_2$; and (c) R$^9$ is halogen, CN, oxo, R$^6$, SR$^6$, OR$^6$, N(R$^6$)$_2$, CON(R$^6$)$_2$, CO$_2$R$^6$, CON(R)COR$^6$, N(R)T$_n$CO$_2$R$^6$, N(R)T$_n$NRCO$_2$R$^6$, N(R)T$_n$N(R$^6$)$_2$, NO$_2$, T$_n$(haloalkyl), CO$_2$N(R$^6$)$_2$, COR$^6$, SO$_2$R$^6$, or SO$_2$N(R$^6$)$_2$.

9. The compound according to claim 7, wherein said compound has one or more features selected from the group consisting of:

(a) R$^2$ is hydrogen, alkoxy, aminoalkyl, or halogen;

(b) R$^3$ is hydrogen, alkoxy, aralkoxy, or halogen;

(c) R$^4$ is hydrogen or (CH$_2$)$_y$R$^2$;

(d) R$^5$ is CON(R$^7$)$_2$, Ar, (CH$_2$)$_y$CO$_2$R, or (CH$_2$)$_y$N(R$^7$)$_2$; and (e) R$^9$ is halogen, CN, oxo, R$^6$, SR$^6$, OR$^6$, N(R$^6$)$_2$, CON(R$^6$)$_2$, CO$_2$R$^6$, CON (R)COR$^6$, or N(R)T$_n$CO$_2$R$^6$.

10. The compound according to claim 9, wherein:

(a) R$^2$ is hydrogen, alkoxy, aminoalkyl, or halogen;

(b) R$^3$ is hydrogen, alkoxy, aralkoxy, or halogen;

(c) R$^4$ is hydrogen or (CH$_2$)$_y$R$^2$;

(d) R$^5$ is CON(R$^7$)$_2$, Ar, (CH$_2$)$_y$CO$_2$R, or (CH$_2$)$_y$N(R$^7$)$_2$; and (e) R$^9$ is halogen, CN, oxo, R$^6$, SR$^6$, OR$^6$, N(R$^6$)$_2$, CON(R$^6$)$_2$, CO$_2$R$^6$, CON(R)COR$^6$, or N(R)T$_n$CO$_2$R$^6$.

11. A compound selected from the group consisting of:

No. Ia- Structure

20

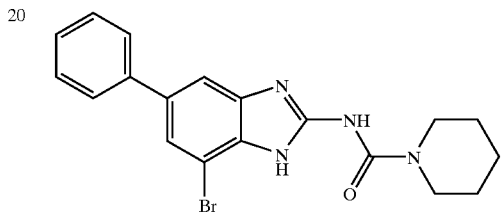

-continued
| No. Ia- | Structure |
|---|---|
| 25 | 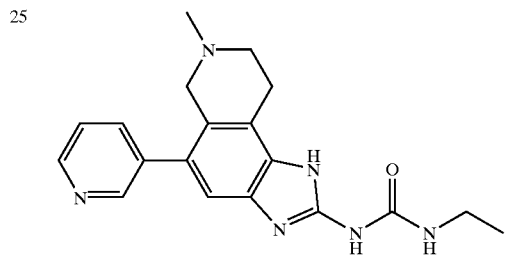 |
| 28 | 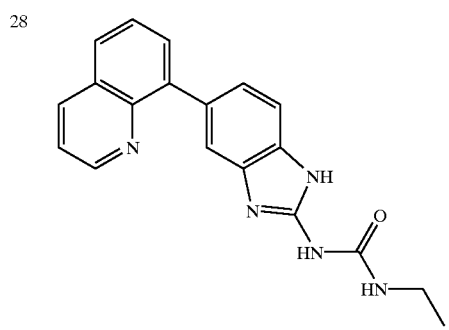 |
| 29 | 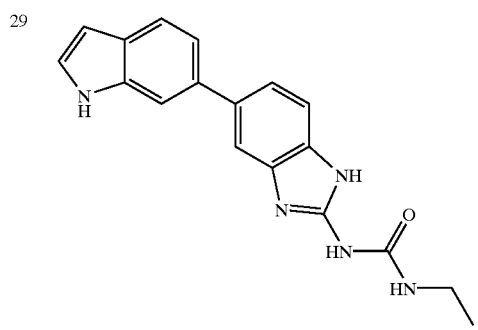 |
| 33 | 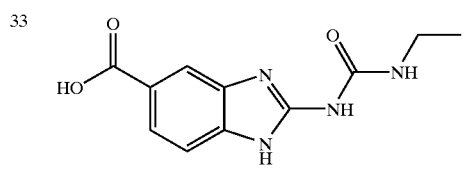 |
| 35 | 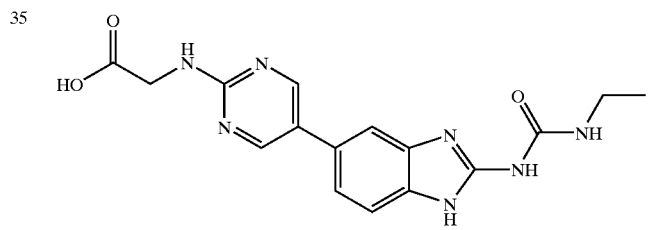 |
| 38 | 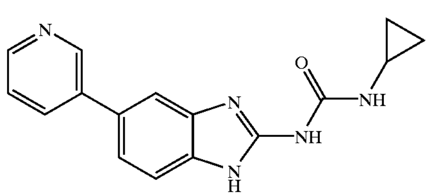 |

-continued
| No. Ia- | Structure |
|---|---|
| 40 | 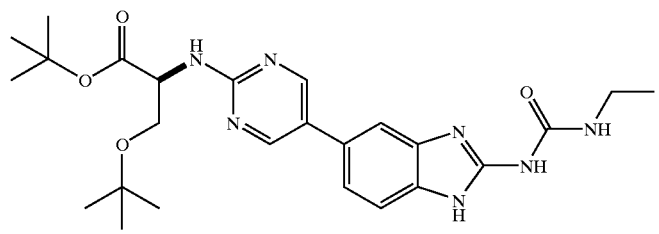 |
| 42 | 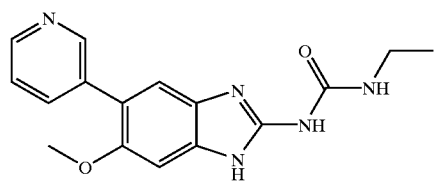 |
| 43 | 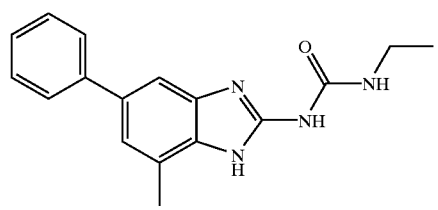 |
| 44 | 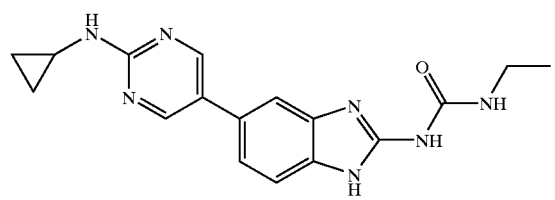 |
| 45 | 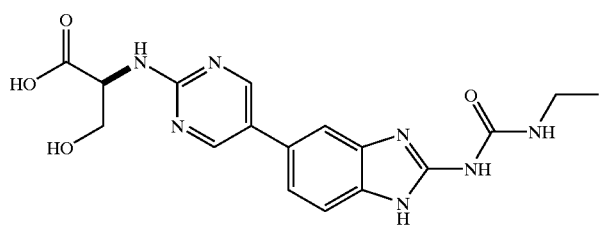 |
| 46 | 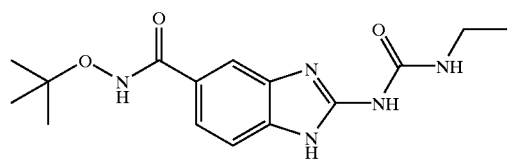 |
| 47 | 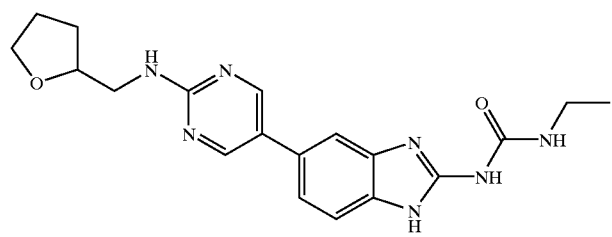 |

-continued
| No. Ia- | Structure |
|---|---|
| 48 | 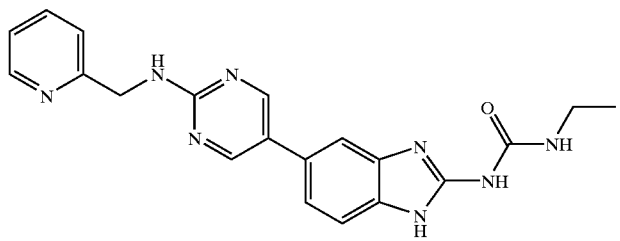 |
| 49 | 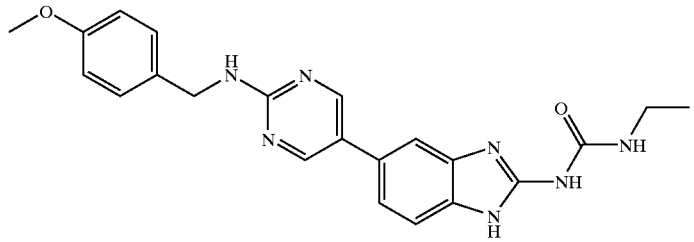 |
| 50 | 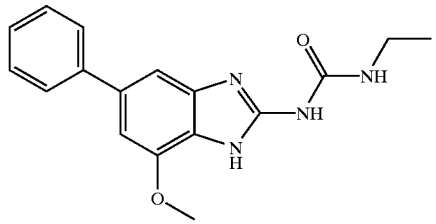 |
| 51 | 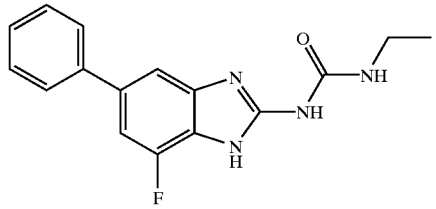 |
| 52 | 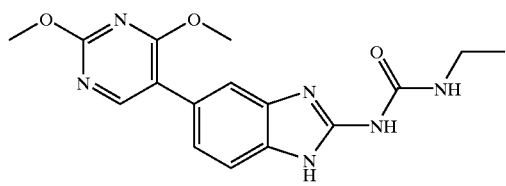 |
| 53 | 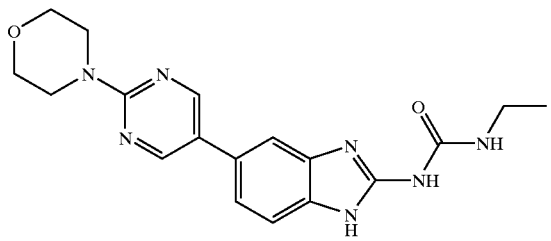 |
| 54 | 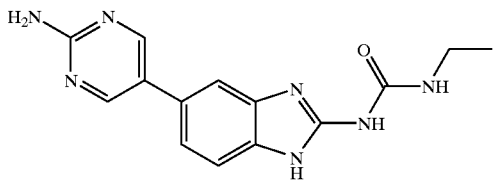 |

-continued
| No. Ia- | Structure |
|---|---|
| 55 | 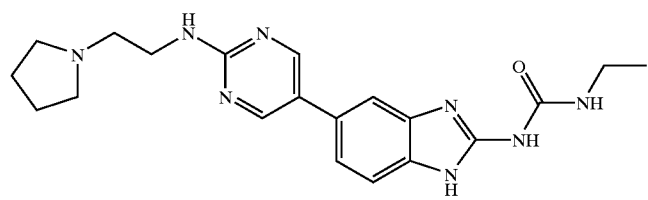 |
| 56 | 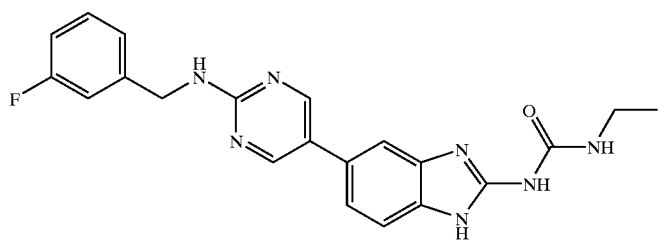 |
| 57 | 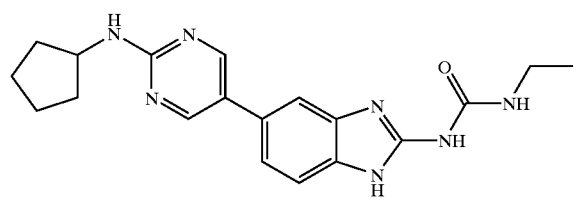 |
| 58 | 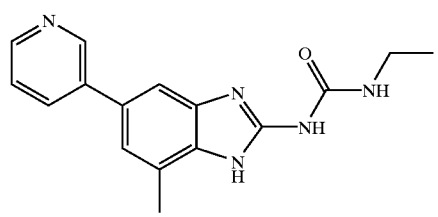 |
| 59 | 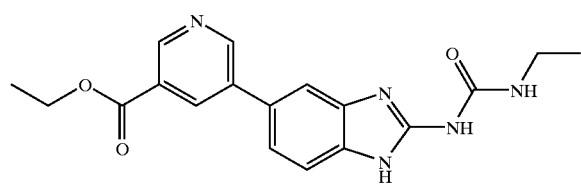 |
| 60 | 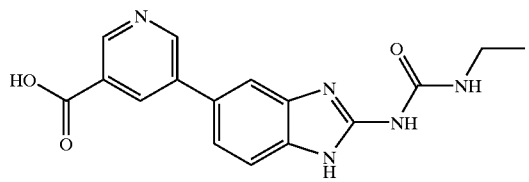 |
| 61 | 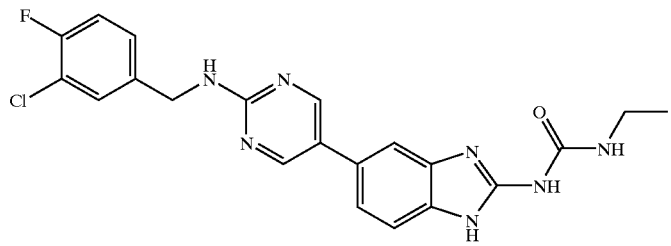 |

-continued
| No. Ia- | Structure |
|---|---|
| 62 | 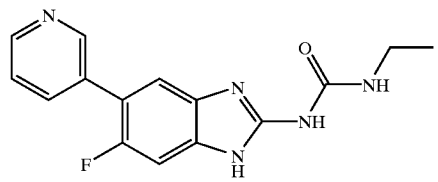 |
| 63 | 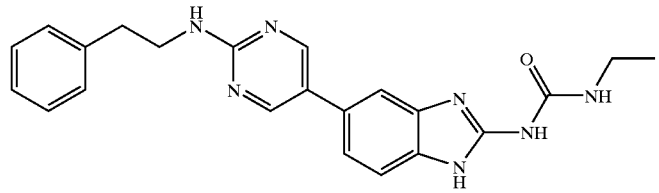 |
| 64 | 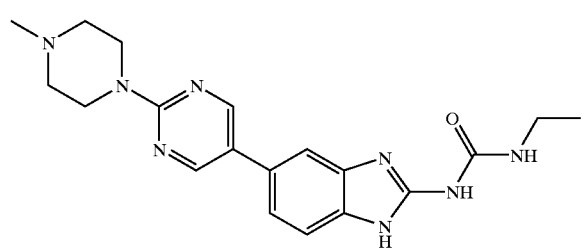 |
| 65 | 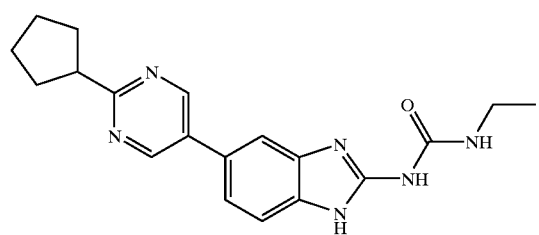 |
| 66 | 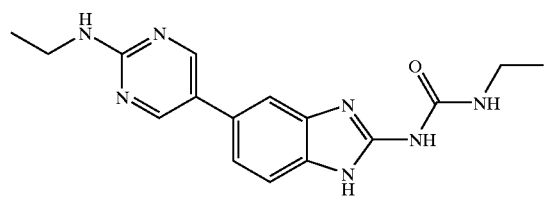 |
| 68 | 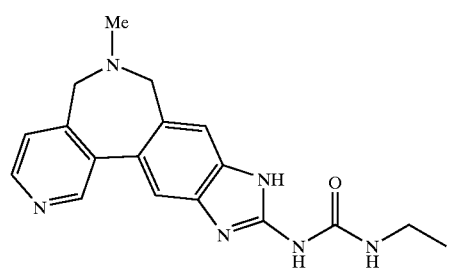 |

| No. Ia- | Structure |
|---|---|
| 83 | 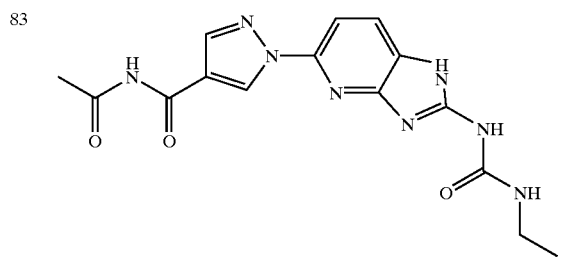 |
| 84 | 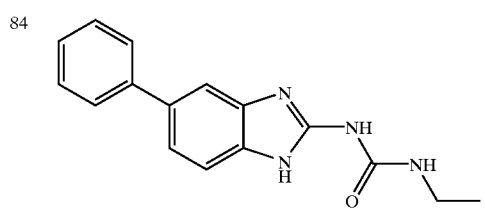 |
| 89 | 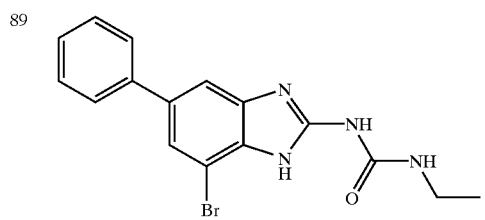 |
| 92 | 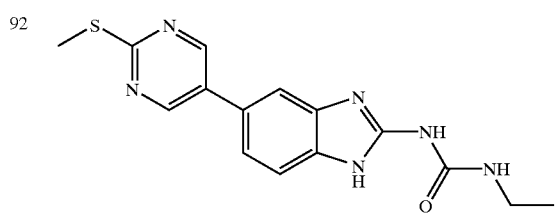 |
| 98 | 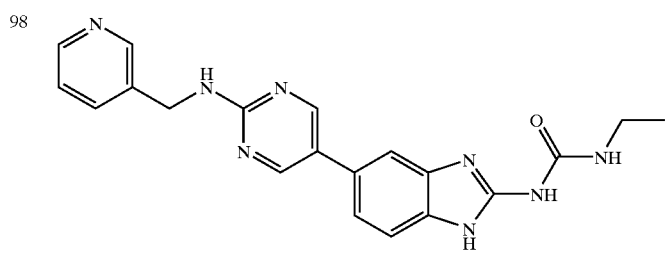 |
| 99 | 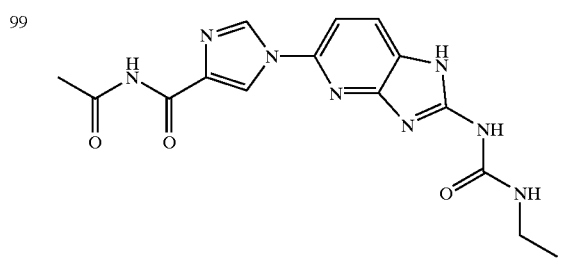 |

-continued
| No. Ia- | Structure |
|---|---|
| 100 | 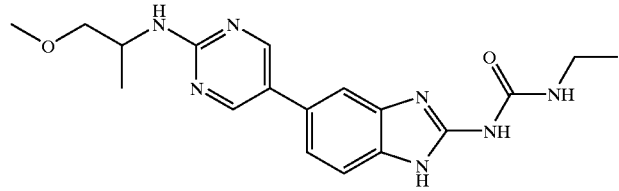 |
| 102 | 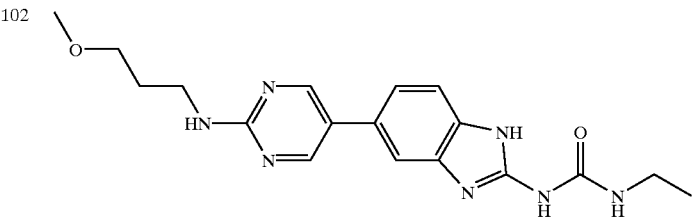 |
| 103 | 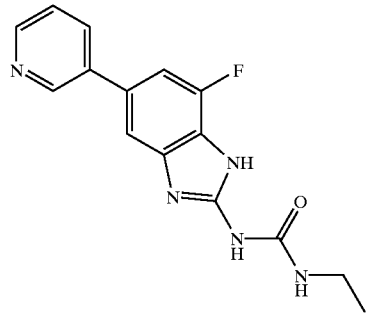 |
| 104 | 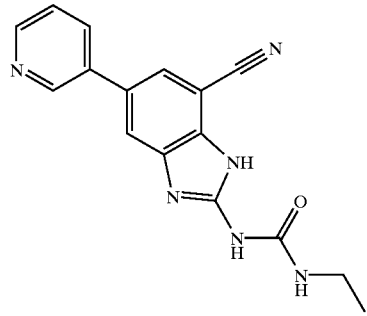 |
| 105 | 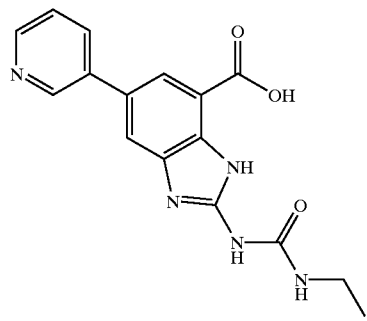 |

-continued
| No. Ia- | Structure |
|---|---|
| 106 | 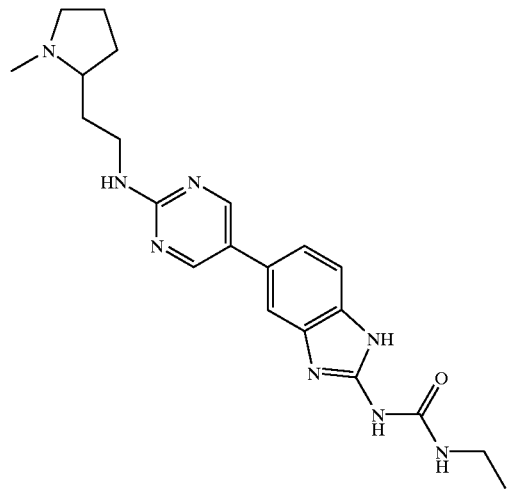 |
| 107 | 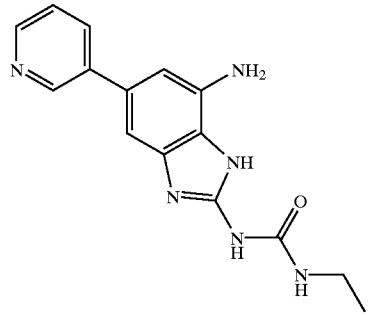 |
| 108 | 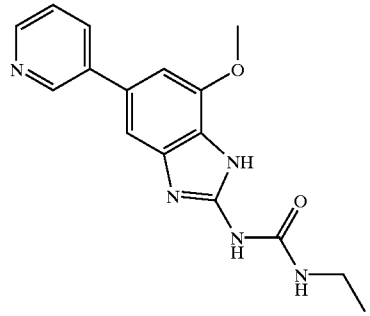 |
| 109 | 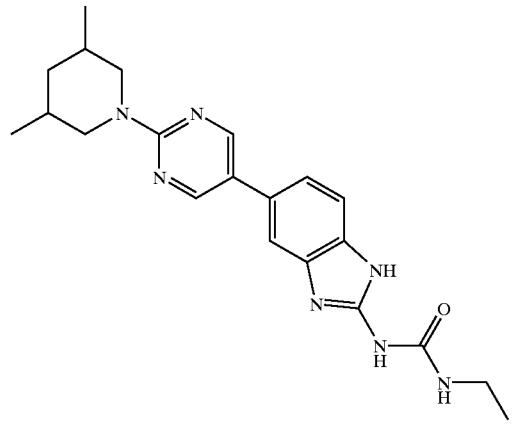 |

-continued
| No. Ia- | Structure |
|---|---|
| 110 | 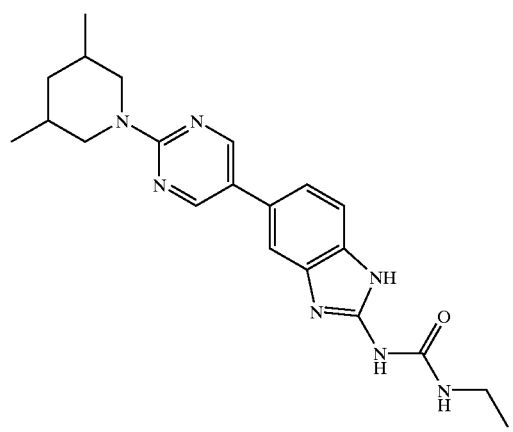 |
| 111 | 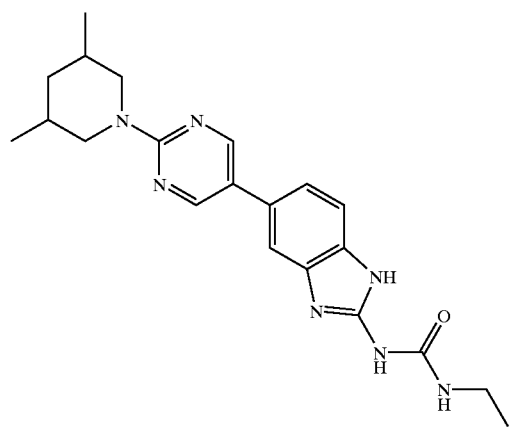 |
| 112 | 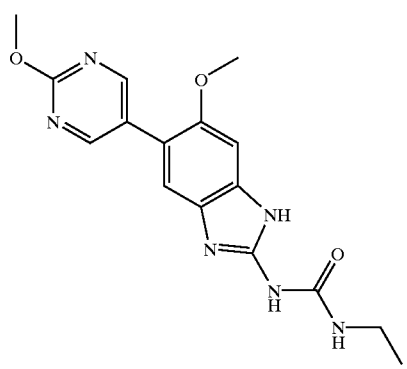 |
| 113 | 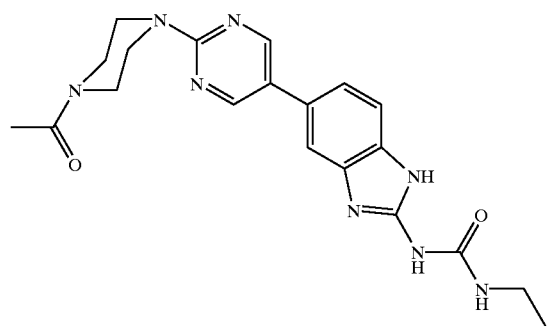 |

-continued
| No. Ia- | Structure |
|---|---|
| 116 | 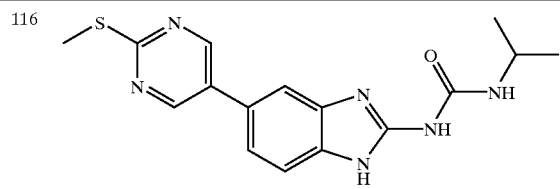 |
| 117 | 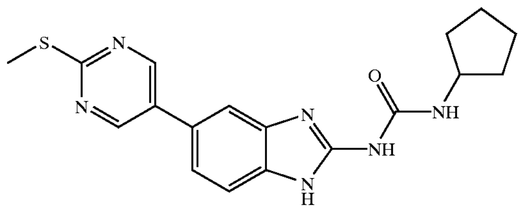 |
| 118 | 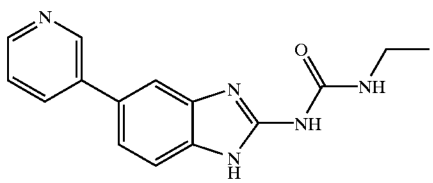 |
| 119 | 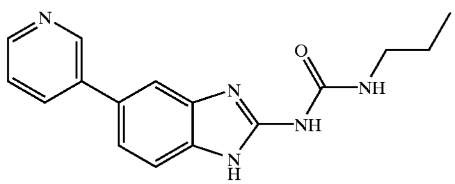 |
| 120 | 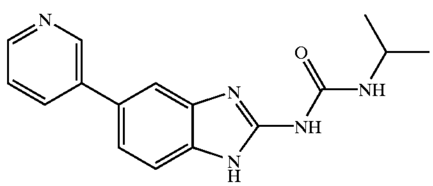 |
| 121 | 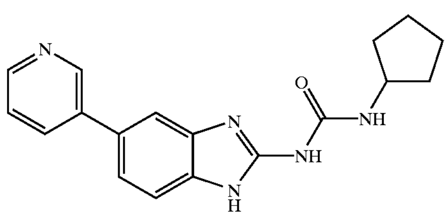 |
| — | — |
| 123 | 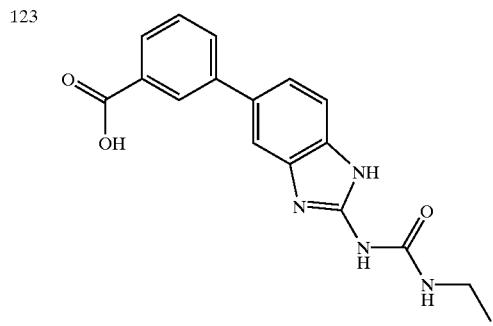 |

-continued
| No. Ia- | Structure |
|---|---|
| 124 | 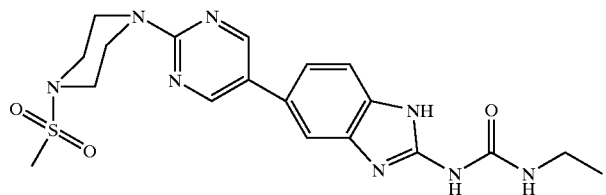 |
| 125 | 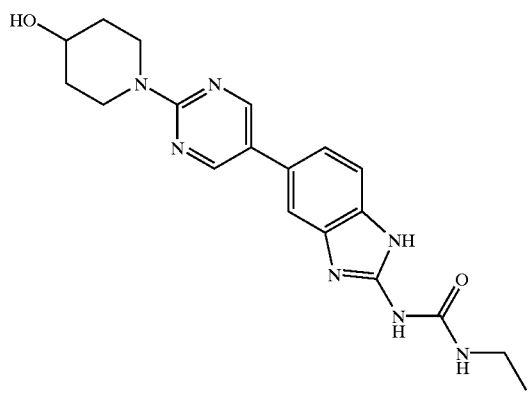 |
| 126 | 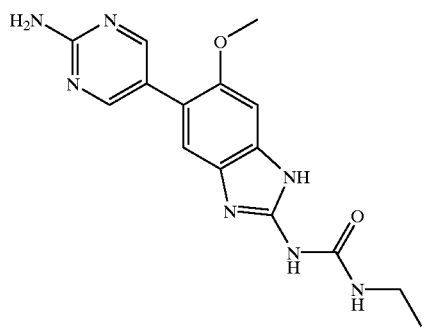 |
| 127 | 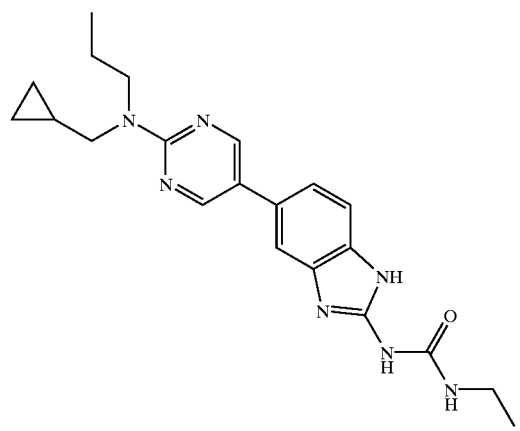 |

-continued
| No. Ia- | Structure |
|---|---|
| 128 | 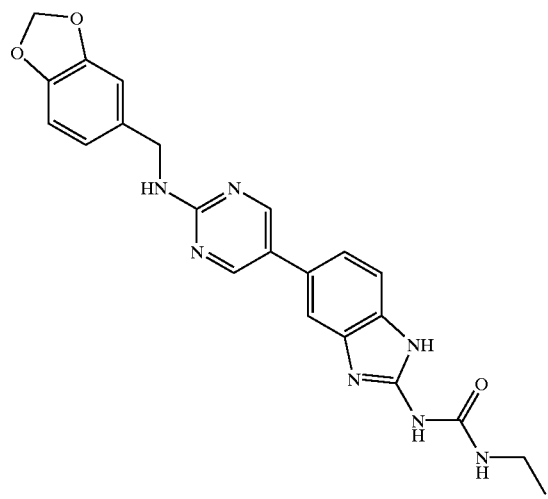 |
| 129 | 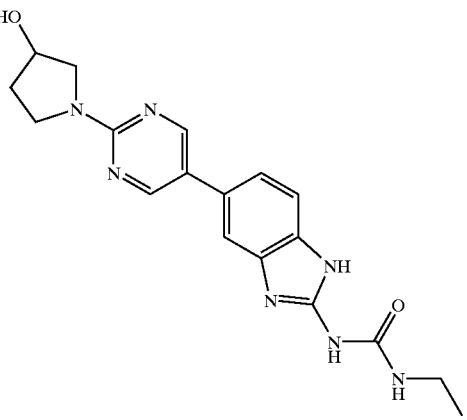 |
| 130 | 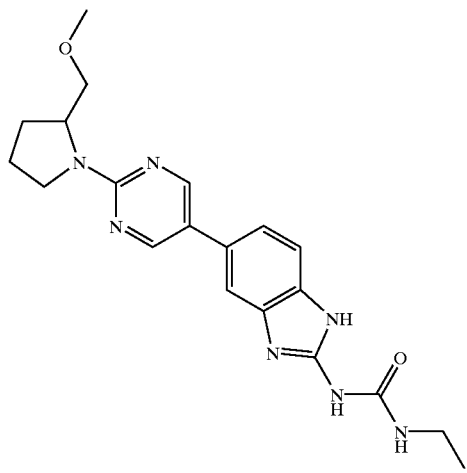 |
| 131 | 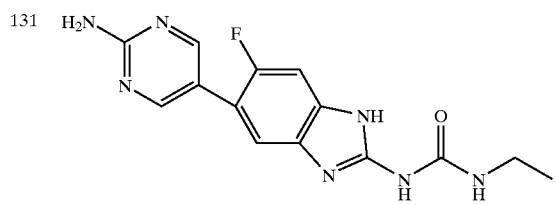 |

-continued
| No. Ia- | Structure |
|---|---|
| 132 | 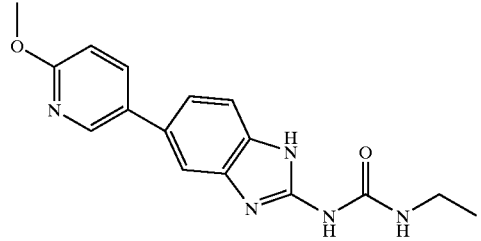 |
| 133 | 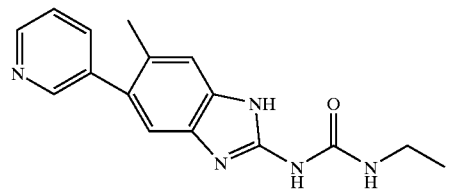 |
| 134 | 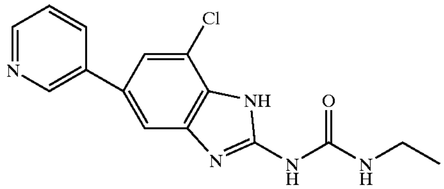 |
| 135 | 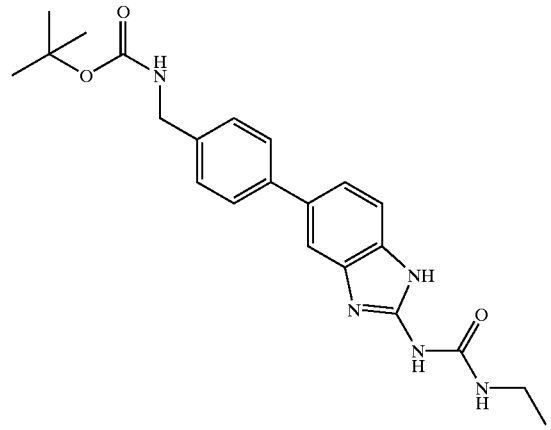 |
| 136 | 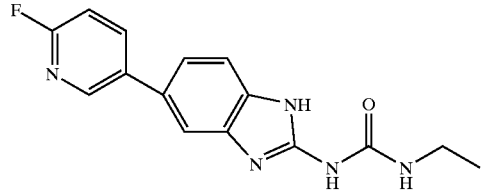 |

-continued
| No. Ia- | Structure |
|---|---|
| 137 | 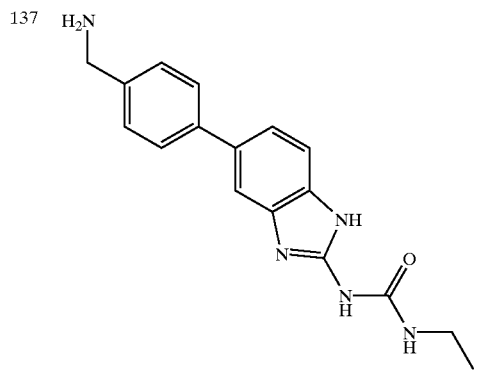 |
| 138 | 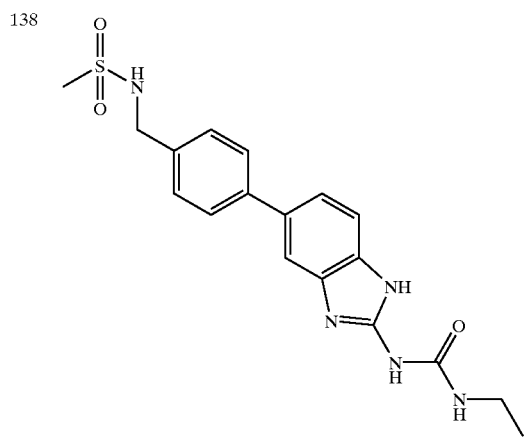 |
| 139 | 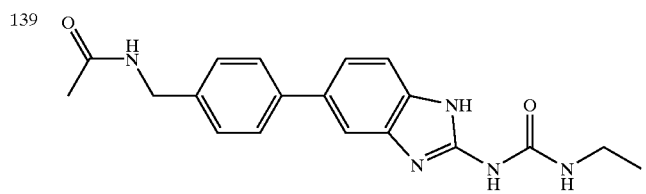 |
| 140 | 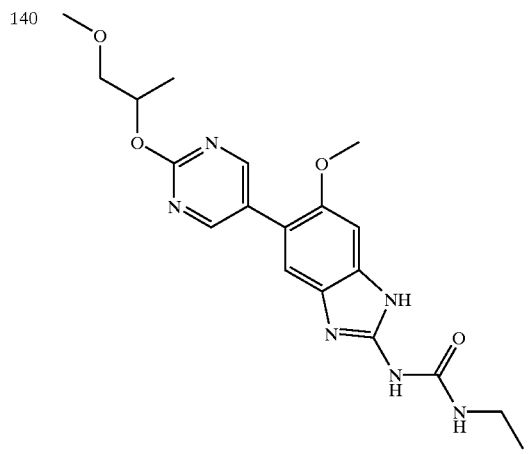 |

-continued
| No. Ia- | Structure |
|---|---|
| 141 | 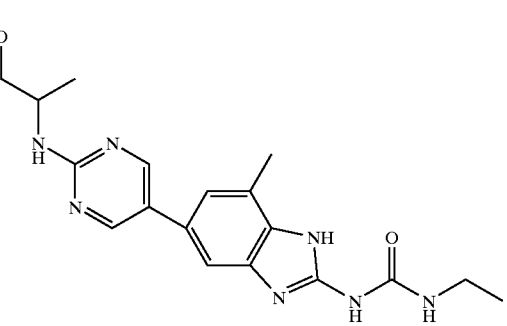 |
| 142 | 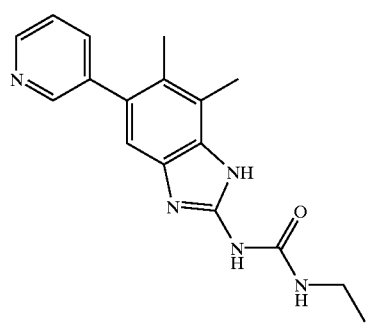 |
| 143 | 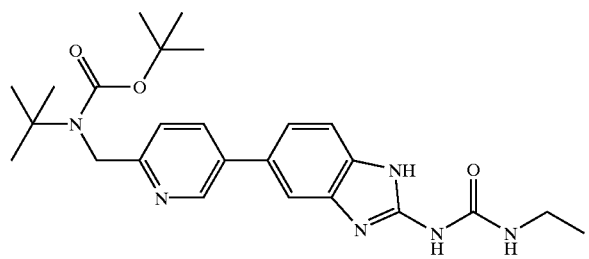 |
| 144 | 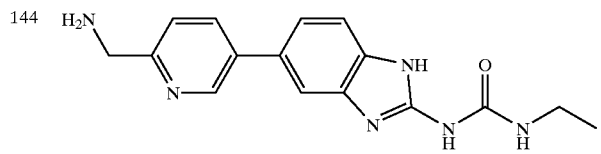 |
| 145 | 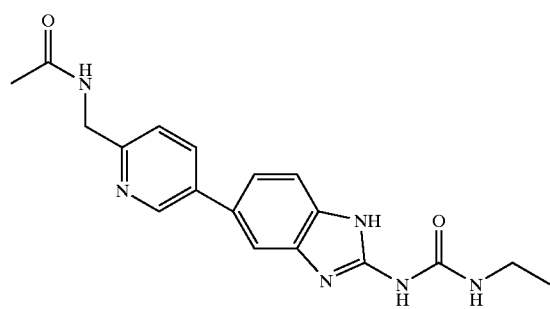 |

-continued
| No. Ia- | Structure |
|---|---|
| 146 | 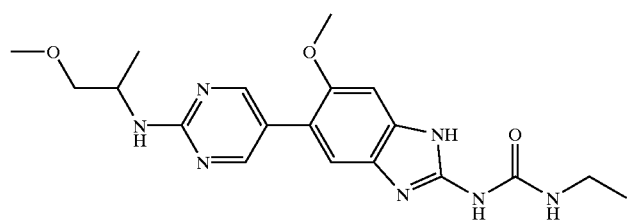 |
| 147 | 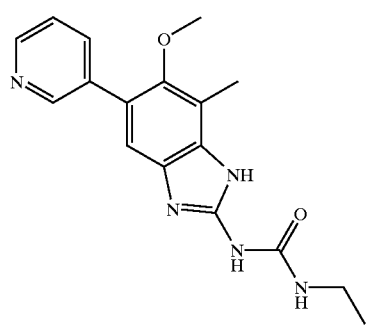 |
| 148 | 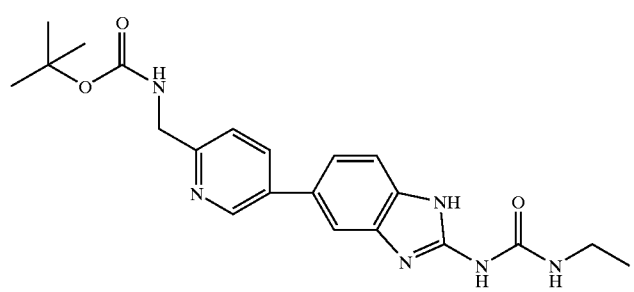 |
| 149 | 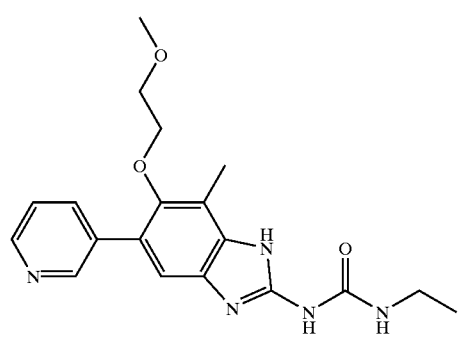 |
| 150 | 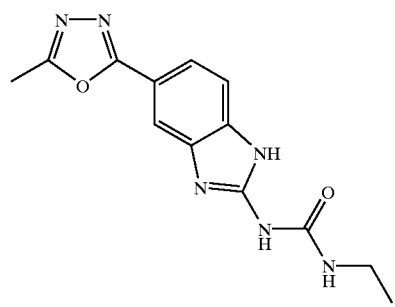 |

-continued
| No. Ia- | Structure |
|---|---|
| 151 | 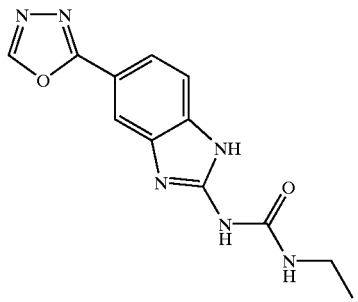 |
| 152 | 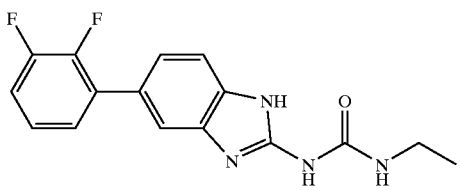 |
| 153 | 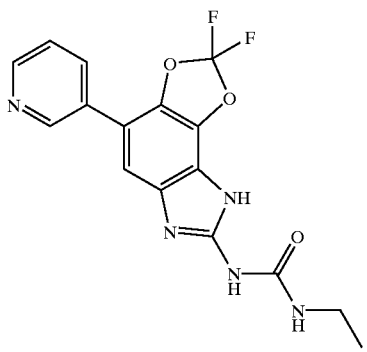 |
| 154 | 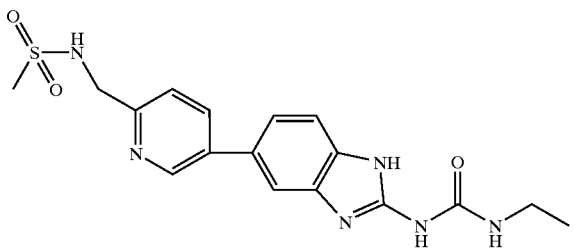 |
| 155 | 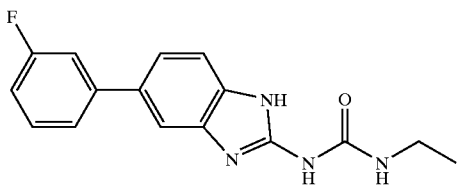 |

-continued
| No. Ia- | Structure |
|---|---|
| 156 | 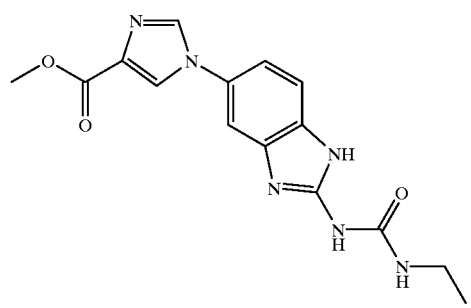 |
| 157 | 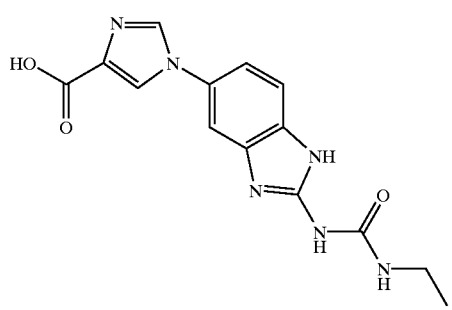 |
| 158 | 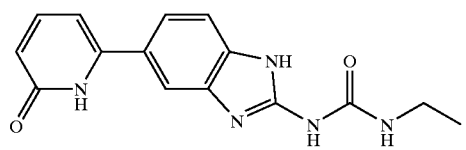 |
| 159 | 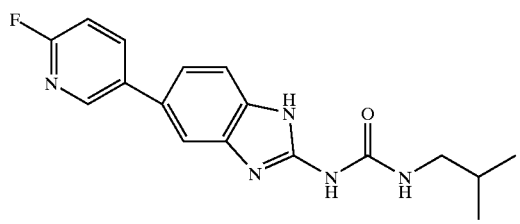 |
| 160 | 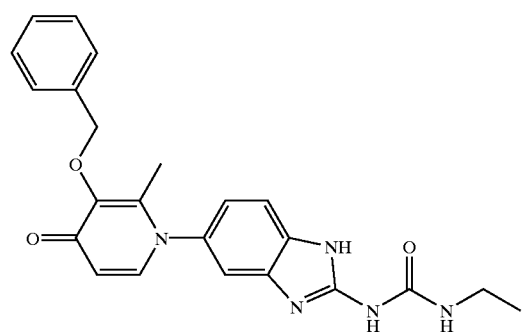 |
| 161 | 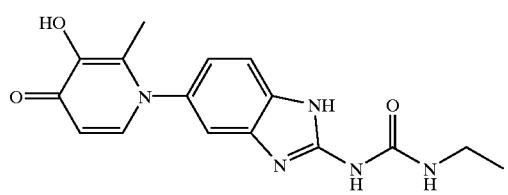 |

-continued
| No. Ia- | Structure |
|---|---|
| 162 | 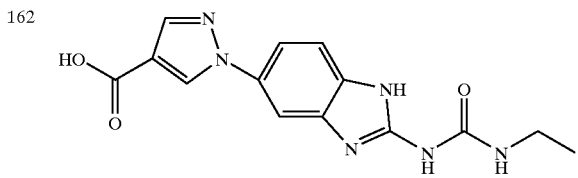 |
| 163 | 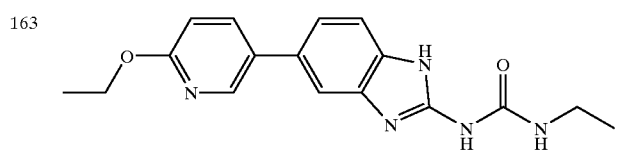 |
| 164 | 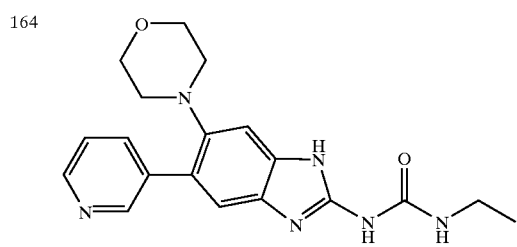 |
| 165 | 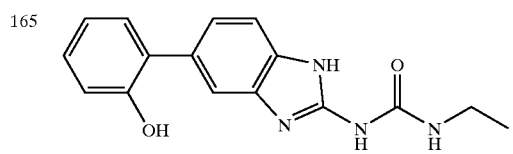 |
| 166 | 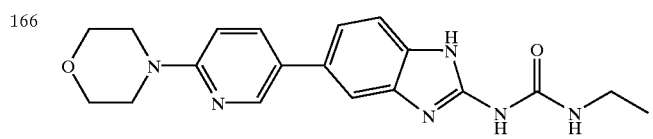 |
| 167 | 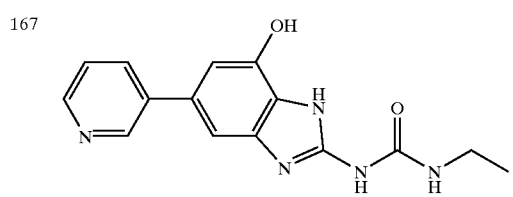 |
| 168 | 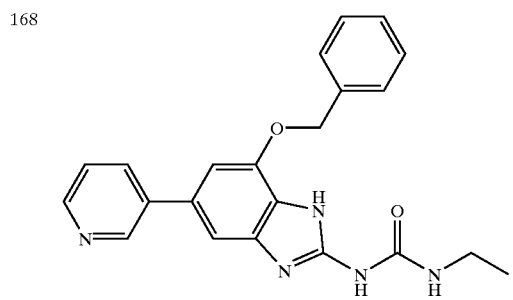 |
| 169 | 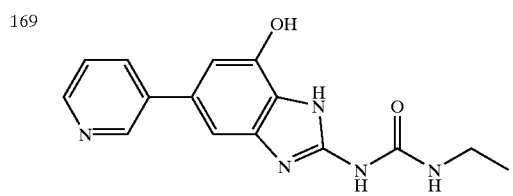 |

-continued
| No. Ia- | Structure |
|---|---|
| 170 | 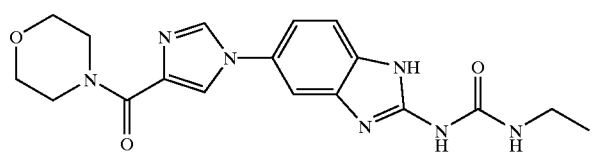 |
| 171 | 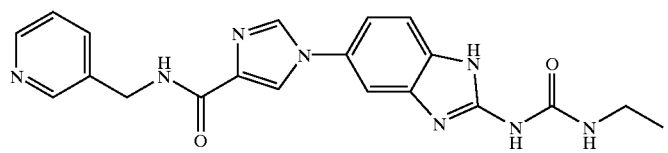 |
| 172 | 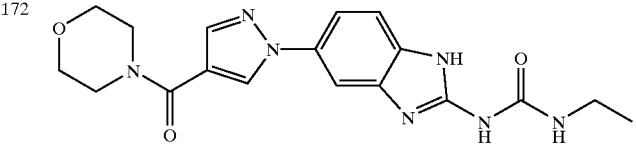 |
| 173 | 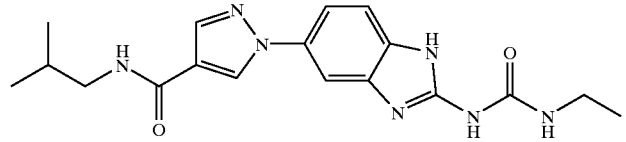 |
| 174 | 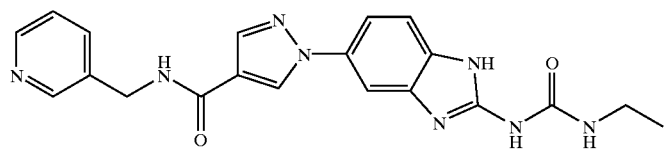 |
| 175 | 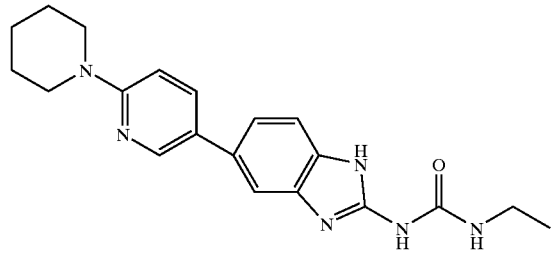 |
| 176 | 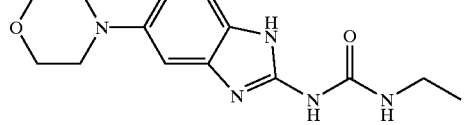 |
| 177 | 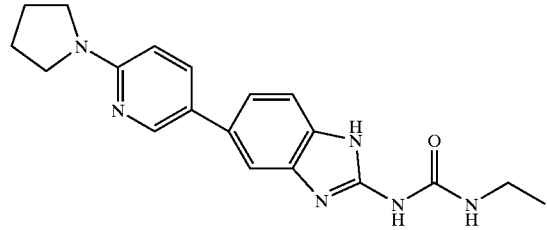 |

-continued
| No. Ia- | Structure |
|---|---|
| 178 | 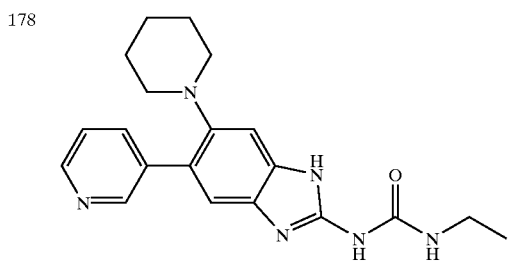 |
| 179 | 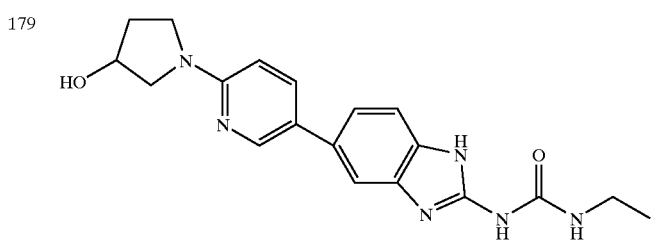 |
| 180 | 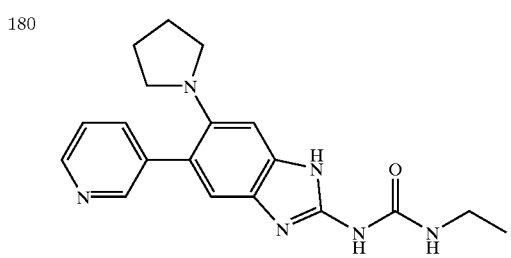 |
| 181 | 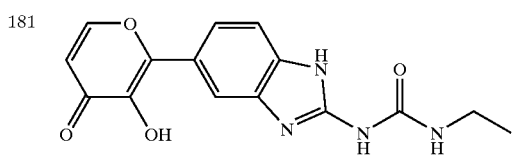 |
| 182 | 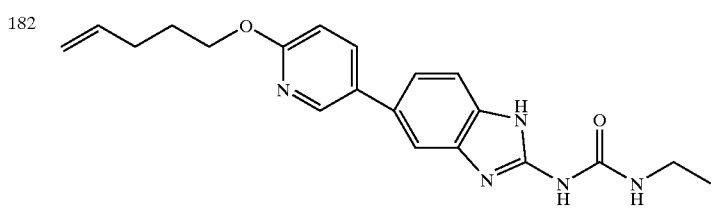 |
| 183 | 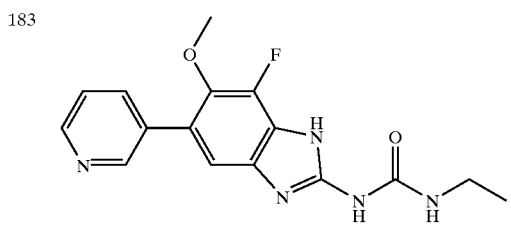 |

-continued
| No. Ia- | Structure |
|---|---|
| 184 | 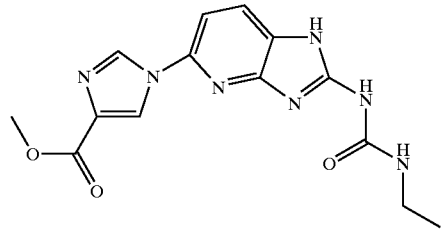 |
| 185 | 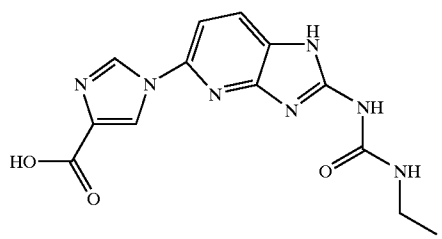 |
| 186 | 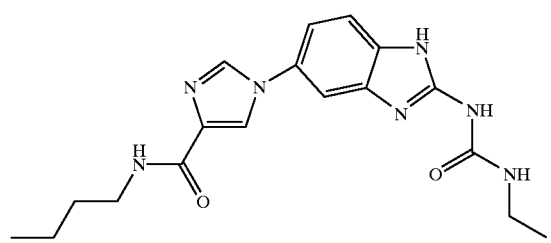 |
| 187 | 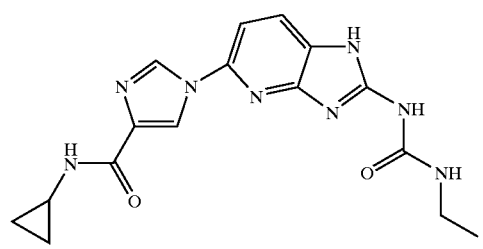 |
| 188 | 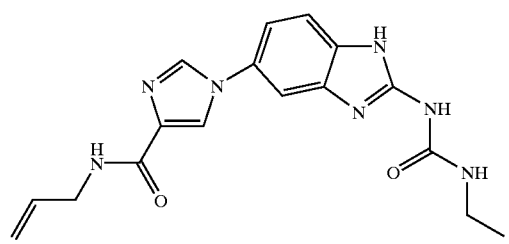 |
| 189 | 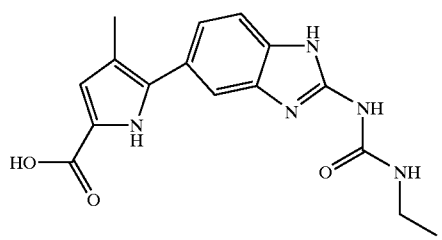 |

| No. Ia- | Structure |
|---|---|
| 190 | 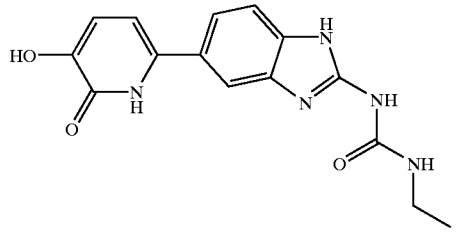 |
| 191 | 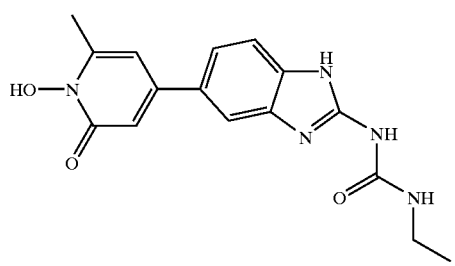 |
| 192 | 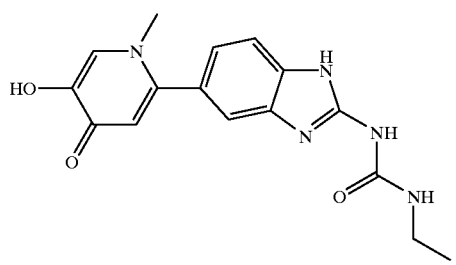 |
| 193 | 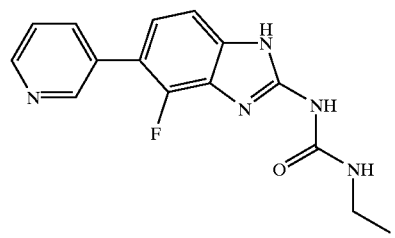 |
| 194 | 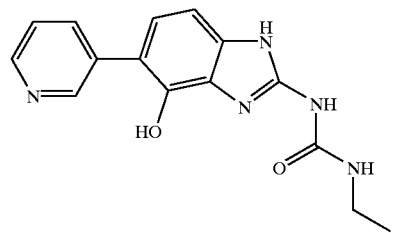 |

-continued
| No. Ia- | Structure |
|---|---|
| 195 | 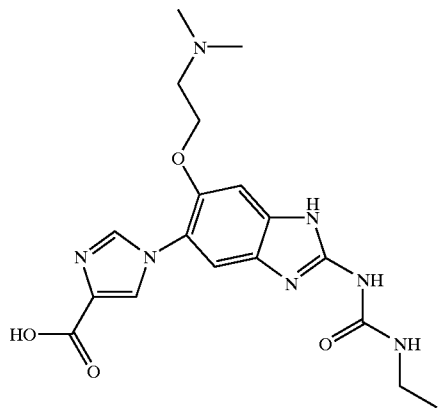 |
| 196 | 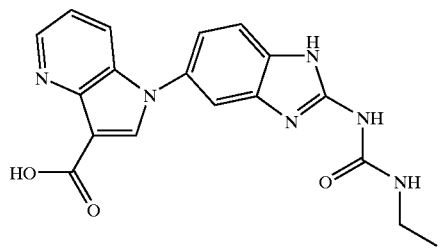 |
| 197 | 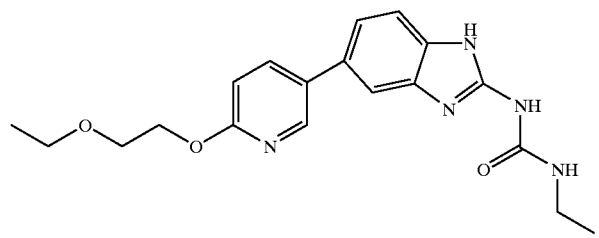 |
| 198 | 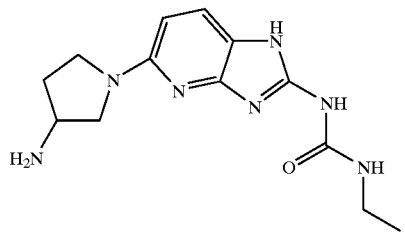 |
| 199 | 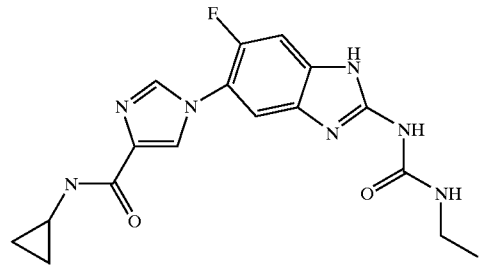 |

-continued
| No. Ia- | Structure |
|---|---|
| and200 | 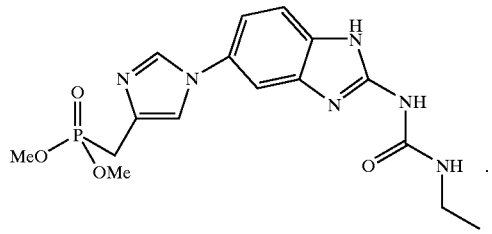 |
12. A compound selected from the group consisting of:
| No. Ib- | Structure |
|---|---|
| 3 | 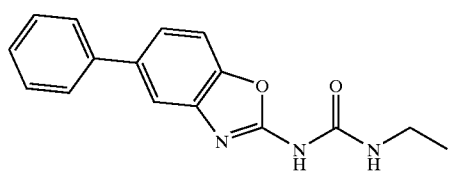 |
| 4 | 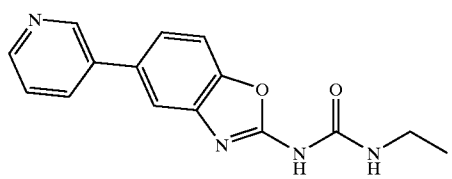 |
| 5 | 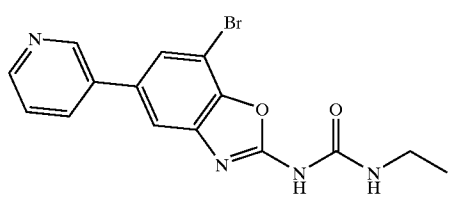 |
| 6 | 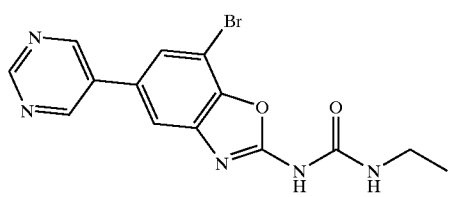 |
| 7 | 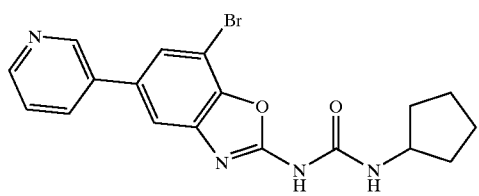 |

-continued

| No. Ib- | Structure |
|---|---|
| 8 | (2-aminopyrimidin-5-yl, 7-methylbenzoxazole, N-ethylurea) |
| 9 | (2-cyclopropylaminopyrimidin-5-yl, 7-methylbenzoxazole, N-ethylurea) |
| 10 | (2-benzylaminopyrimidin-5-yl, benzoxazole, N-ethylurea) |
| 11 | (imidazol-1-yl, 7-methylbenzoxazole, N-ethylurea) |
| 12 | (pyrazol-1-yl, 7-methylbenzoxazole, N-ethylurea) |
| 13 | (2-ethylaminopyrimidin-5-yl, 7-methylbenzoxazole, N-ethylurea) |
| 14 | (6-oxo-1,6-dihydropyridin-3-yl, 7-methylbenzoxazole, N-ethylurea) |

-continued
| No. Ib- | Structure |
|---|---|
| 15 | 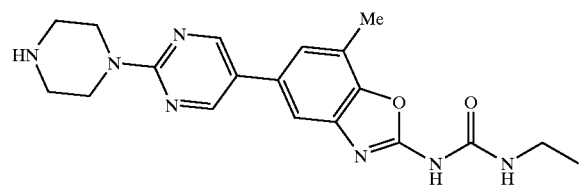 |
| 16 | 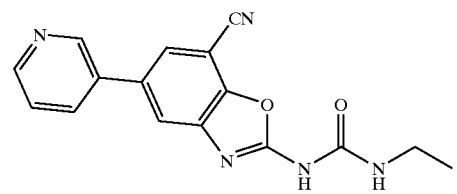 |
| 17 | 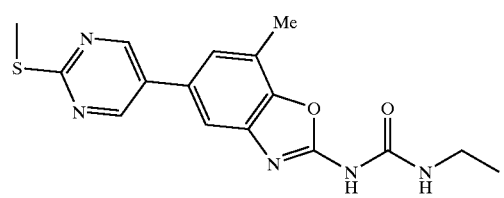 |
| 20 | 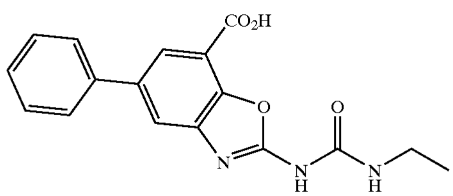 |
| 21 | 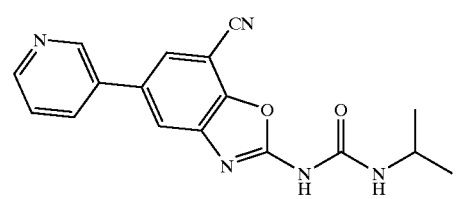 |
| 22 | 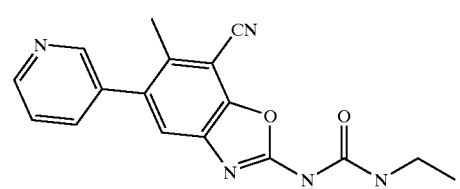 |
| 23 | 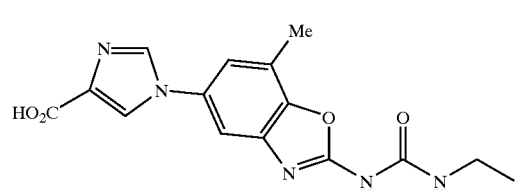 |
| 24 | 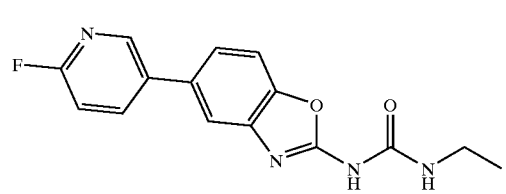 |

-continued

| No. Ib- | Structure |
|---|---|
| 25 | 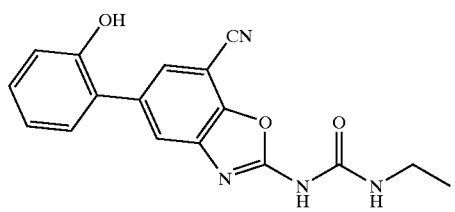 |
| 26 | 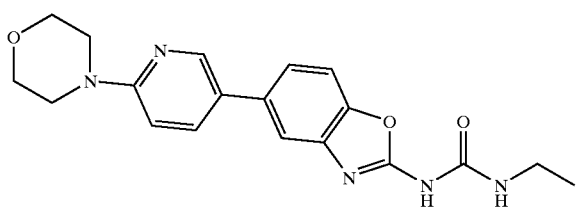 |
| 27 | 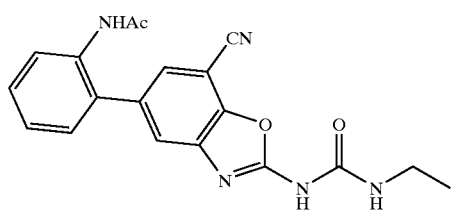 |
| and 28 | 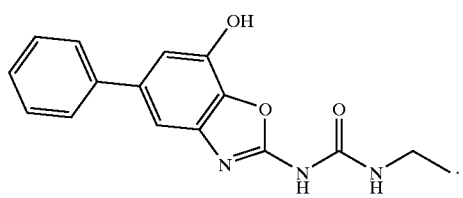 |

13. A composition comprising an effective amount of a compound according to any one of claims 1 to 10, and a pharmaceutically acceptable carrier.

14. The composition according to claim 13, wherein said compound is formulated in a pharmaceutically acceptable manner for administration to a patient.

15. The composition according to claim 13 further comprising an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

16. The composition according to claim 14 further comprising an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

17. The composition according to claim 13 further comprising an agent that increases the susceptibility of bacterial organisms to antibiotics.

18. The composition according to claim 15 further comprising an agent that increases the susceptibility of bacterial organisms to antibiotics.

19. A method of decreasing bacterial quantity in a biological sample comprising the step of contacting said biological sample with a compound according to either of claims 1 or 6.

20. The method according to claim 19 further comprising the step of contacting said biological sample with an agent which increases the susceptibility of bacterial organisms to antibiotics.

21. A method of inhibiting gyrase in a mammal, comprising the step of administering to said mammal a composition according to claim 13.

22. A method of treating a bacterial infection in a mammal in need thereof, comprising the step of administering to said mammal a therapeutically effective amount of a composition according to claim 13.

23. The method according to claim 22, wherein the bacterial infection to be treated is characterized by the presence of one or more of the following: *Streptococcus pneumoniae, Streptococcus pyrogenes, Enterococcus fecalis, Enterococcus faecium, Klebsiella pneumoniae,* Enterobacter sps. Proteus sps. *Pseudomonas aeruginosa, E. coli, Serratia marcesens, S. aureus,* or Coag. Neg. Staph.

24. The method according to claim 22, wherein the bacterial infection to be treated is selected from one or more of the following: urinary tract infections, pneumonia, prostatitis, skin and soft tissue infections, intra-abdominal infections, or infections of febrile neutropenic patients.

25. The method according to claim 22 further comprising the step of administering to said patient an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound, either as part of a multiple dosage form together with said compound or as a separate dosage form.

26. The method according to claim 22 further comprising the step of administering to said patient an agent that increases the susceptibility of bacterial organisms to antibiotics.

* * * * *